US012007593B2

(12) United States Patent
Erickson et al.

(10) Patent No.: US 12,007,593 B2
(45) Date of Patent: Jun. 11, 2024

(54) ORGANIC LIGHT EMITTING DIODE WITH COLOR-CORRECTION FOR MAXIMUM WHITE-POINT COLOR SHIFT

(71) Applicant: 3M INNOVATIVE PROPERTIES COMPANY, St. Paul, MN (US)

(72) Inventors: Nicholas C. Erickson, St. Paul, MN (US); David G. Freier, St. Paul, MN (US); Robert L Brott, Woodbury, MN (US); Bing Hao, Woodbury, MN (US); David A. Rosen, Maplewood, MN (US); Stephen M. Menke, St. Paul, MN (US); Bert T. Chien, St. Paul, MN (US); Seong Taek Lee, Woodbury, MN (US); Encai Hao, Woodbury, MN (US); Zhaohui Yang, North Oaks, MN (US); Albert I. Everaerts, Tuscon, AZ (US); Yongshang Lu, Woodbury, MN (US); William Blake Kolb, Stillwater, MN (US); Keith R. Bruesewitz, River Falls, MN (US); Adam D. Haag, Woodbury, MN (US); Sun-Yong Park, Hwaseong-si (KR); Timothy J. Nevitt, Red Wing, MN (US); Brianna N. Wheeler, Bloomington, MN (US); Jody L. Peterson, Cottage Grove, MN (US); Gilles J. Benoit, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 898 days.

(21) Appl. No.: 17/044,367

(22) PCT Filed: Apr. 9, 2019

(86) PCT No.: PCT/US2019/026491
§ 371 (c)(1),
(2) Date: Oct. 1, 2020

(87) PCT Pub. No.: WO2019/204078
PCT Pub. Date: Oct. 24, 2019

(65) Prior Publication Data
US 2021/0098546 A1    Apr. 1, 2021

Related U.S. Application Data

(60) Provisional application No. 62/659,175, filed on Apr. 18, 2018.

(51) Int. Cl.
*G02B 5/28*    (2006.01)
*H10K 59/35*    (2023.01)
*H10K 59/50*    (2023.01)

(52) U.S. Cl.
CPC ............. *G02B 5/287* (2013.01); *H10K 59/35* (2023.02); *H10K 59/50* (2023.02)

(58) Field of Classification Search
CPC ...................................................... G02B 5/287
(Continued)

(56) References Cited

U.S. PATENT DOCUMENTS

| 4,374,077 A | 2/1983 | Kerfeld |
| 4,576,850 A | 3/1986 | Martens |

(Continued)

FOREIGN PATENT DOCUMENTS

| TW | 200624368 A | 7/2006 |
| WO | WO 2008-128073 | 10/2008 |

(Continued)

OTHER PUBLICATIONS

Burzynski, "Large optical birefringence in poly(p-phenylene vinylene) films measured by optical waveguide techniques", Polymer, Apr. 1990, vol. 31, No. 4, pp. 627-630.

(Continued)

*Primary Examiner* — Long D Pham
(74) *Attorney, Agent, or Firm* — Clifton F. Richardson

(57) ABSTRACT

An OLED display including a display panel and a color-correction component is described. A plurality of comparative display panels otherwise equivalent to the display panel but having one or more different optical thicknesses of (Continued)

Maximum White - Point Color Shift from 0 to 45 degrees

OLED layers have a maximum white-point color shift from 0 to 45 degrees of $WPCS^C_{45}$ and a white-point axial efficiency of $WPAE^C$. The plurality of comparative display panels defines a performance curve along a boundary of performance points. The OLED display and the display panel have respective maximum white-point color shifts from 0 to 45 degrees of $WPCS_{45}$ and $WPCS^O_{45}$ and respective white-point axial efficiencies of WPAE and $WPAE^O$. $WPCS^O_{45}$ and $WPAE^O$ defines a performance point of the display panel to the right of the performance curve and $WPCS_{45}$ and WPAE defines a performance point of the OLED display above or to the left of the performance curve. Methods of making the OLED display are described.

20 Claims, 39 Drawing Sheets

(58) Field of Classification Search
USPC .......................................................... 345/76
See application file for complete search history.

(56) References Cited

U.S. PATENT DOCUMENTS

| | | | |
|---|---|---|---|
| 5,126,394 A | 6/1992 | Revis | |
| 5,175,030 A | 12/1992 | Lu | |
| 5,271,968 A | 12/1993 | Coyle | |
| 5,558,740 A | 9/1996 | Bernard | |
| 5,882,774 A | 3/1999 | Jonza | |
| 5,995,690 A | 11/1999 | Kotz | |
| 6,005,137 A | 12/1999 | Moore | |
| 6,157,490 A | 12/2000 | Wheatley | |
| 6,179,948 B1 | 1/2001 | Merrill | |
| 6,329,058 B1 | 12/2001 | Arney | |
| 6,783,349 B2 | 8/2004 | Neavin | |
| 7,018,713 B2 | 3/2006 | Padiyath | |
| 8,234,998 B2 | 8/2012 | Krogman | |
| 8,313,798 B2 | 11/2012 | Nogueira | |
| 8,343,622 B2 | 1/2013 | Liu | |
| 8,460,568 B2 | 1/2013 | David | |
| 8,557,378 B2 | 10/2013 | Yamanaka | |
| 8,808,811 B2 | 8/2014 | Kolb | |
| 9,276,045 B2 | 3/2016 | Xi | |
| 9,279,921 B2 | 3/2016 | Kivel | |
| 9,541,701 B2 | 1/2017 | Thompson et al. | |
| 9,960,389 B1 | 5/2018 | Hao | |
| 2004/0233125 A1 | 11/2004 | Tanghe | |
| 2005/0179373 A1 | 8/2005 | Kobayashi | |
| 2007/0236134 A1 | 10/2007 | Ho | |
| 2009/0030084 A1 | 1/2009 | Kurosu | |
| 2009/0051276 A1 | 2/2009 | Inoue | |
| 2009/0087629 A1 | 4/2009 | Everaerts | |
| 2009/0296366 A1 | 12/2009 | Shikina | |
| 2010/0028564 A1 | 2/2010 | Cheng | |
| 2010/0040842 A1 | 2/2010 | Everaerts | |
| 2010/0055810 A1 | 3/2010 | Sung | |
| 2010/0193790 A1 | 8/2010 | Yeo | |
| 2011/0064936 A1 | 3/2011 | Hammond-Cunningham | |
| 2011/0126968 A1 | 6/2011 | Determan | |
| 2011/0253301 A1 | 10/2011 | Yamanaka | |
| 2011/0272849 A1 | 11/2011 | Neavin | |
| 2012/0038990 A1 | 2/2012 | Hao | |
| 2012/0056911 A1 | 3/2012 | Safaee-Rad | |
| 2012/0099323 A1 | 4/2012 | Thompson | |
| 2012/0306375 A1* | 12/2012 | van de Ven | ........ H05B 45/3577 315/122 |
| 2014/0175404 A1 | 6/2014 | Shim | |
| 2014/0193612 A1 | 7/2014 | Yu | |
| 2015/0325816 A1 | 11/2015 | Haag | |
| 2017/0353628 A1 | 12/2017 | Kishigami | |

FOREIGN PATENT DOCUMENTS

| | | |
|---|---|---|
| WO | WO 2009-089137 | 7/2009 |
| WO | WO 2010-033558 | 3/2010 |
| WO | WO 2013-116103 | 8/2013 |
| WO | WO 2013-116302 | 8/2013 |
| WO | 2017205174 A1 | 11/2017 |
| WO | WO 2017-205174 | 11/2017 |
| WO | 2018045070 A1 | 3/2018 |
| WO | WO 2018-045070 | 3/2018 |
| WO | WO 2018-080830 | 5/2018 |
| WO | WO 2018-102193 | 6/2018 |
| WO | WO 2018-204648 | 11/2018 |
| WO | WO 2018-204675 | 11/2018 |
| WO | WO 2019-069214 | 4/2019 |

OTHER PUBLICATIONS

Yang, "Group Contribution to Molar Refraction and Refractive Index of Conjugated Polymers", Chemistry of Materials, Jul. 1995, vol. 7, No. 7, pp. 1276-1285.

International Search Report for PCT International Application No. PCT/US2019/026491, mailed on Jul. 26, 2019, 3 pages.

* cited by examiner

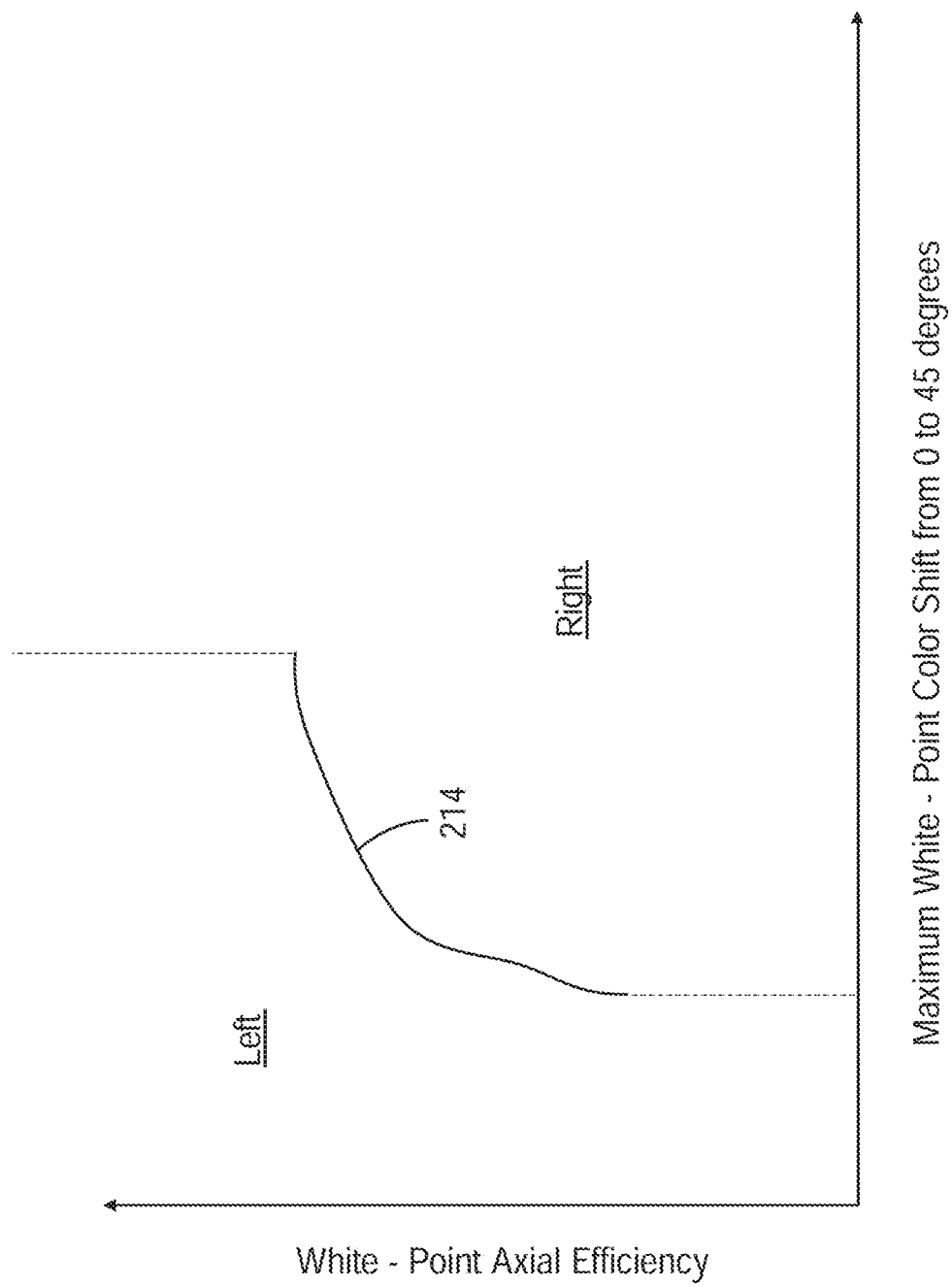

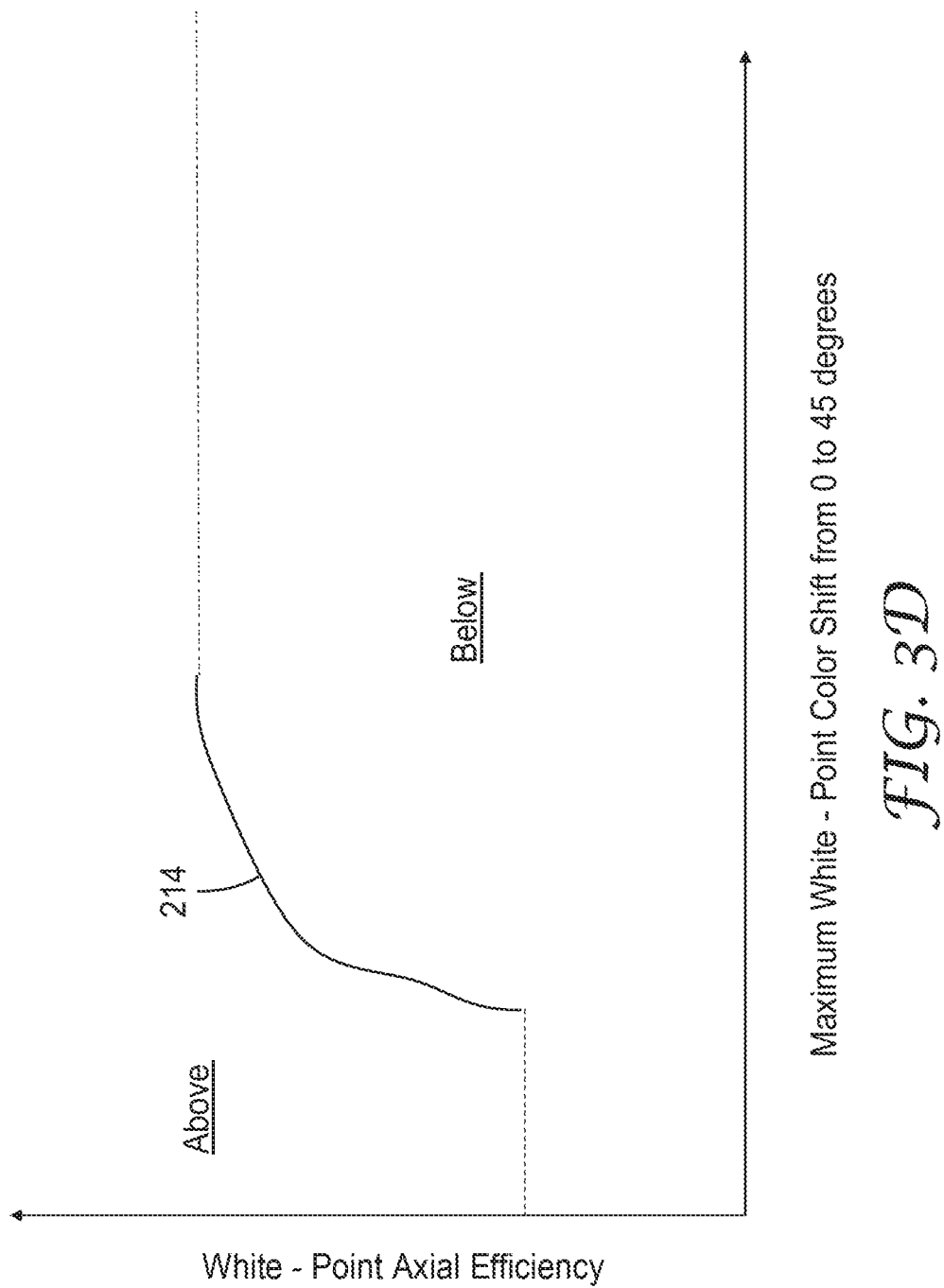

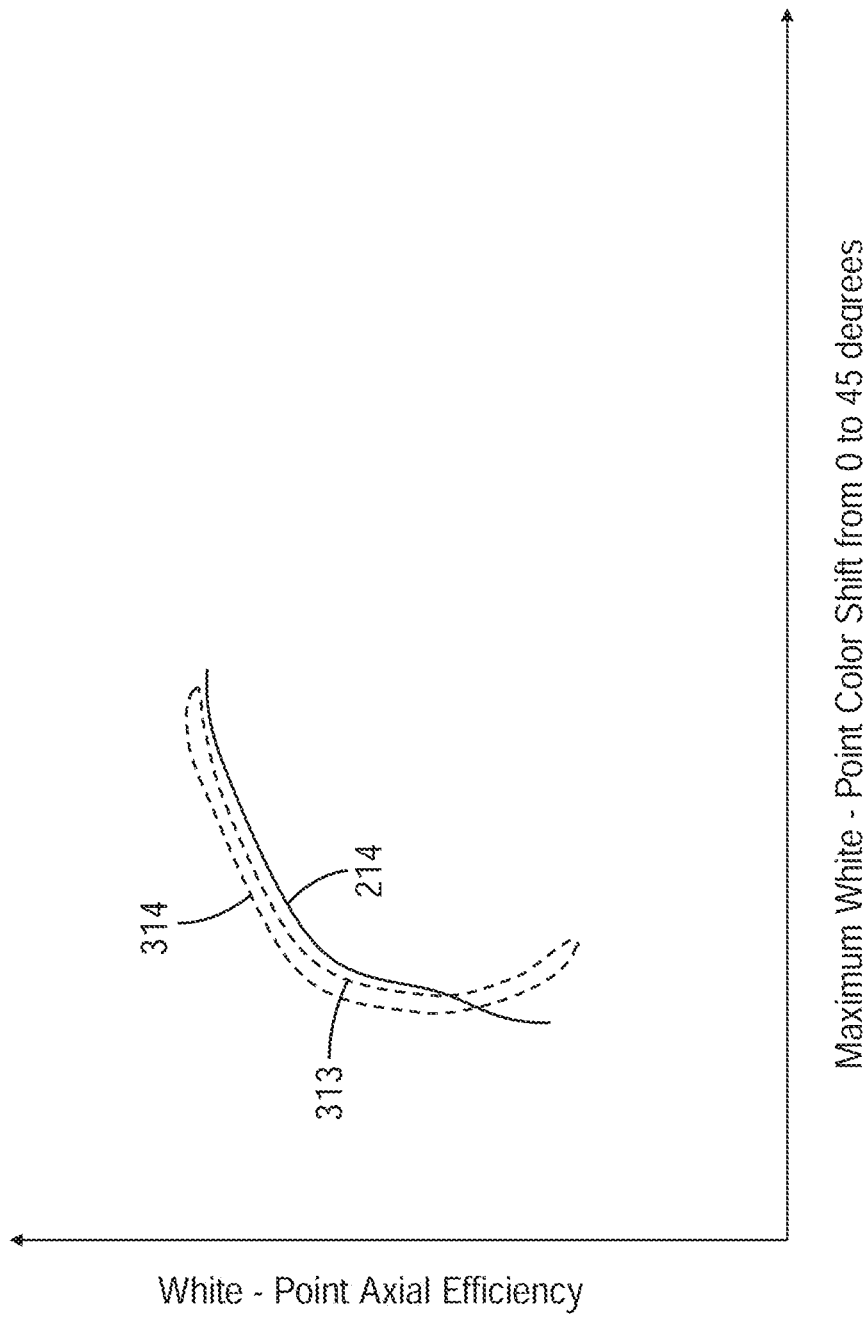

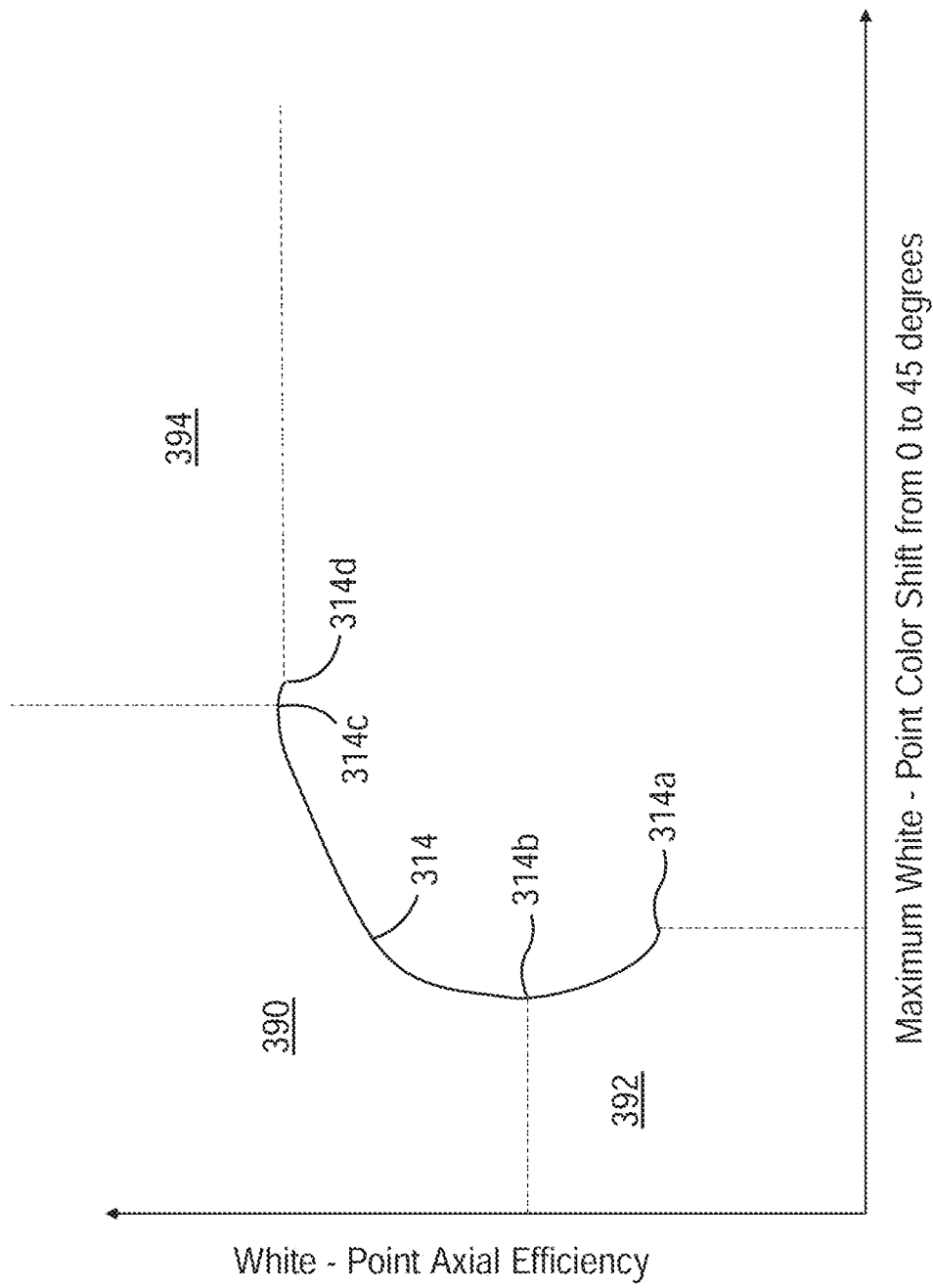

ORGANIC LIGHT EMITTING DIODE WITH COLOR-CORRECTION FOR MAXIMUM WHITE-POINT COLOR SHIFT

CROSS REFERENCE TO RELATED APPLICATIONS

This application is a national stage filing under 35 U.S.C. 371 of PCT/US2019/026491, filed Apr. 9, 2019, which claims the benefit of U.S. Provisional Patent Application No. 62/659,175, filed Apr. 18, 2018, the disclosures of which are incorporated by reference in their entirety herein.

BACKGROUND

Organic light emitting diode (OLED) displays, such as active-matrix organic light-emitting diode (AMOLED) displays, often produce a light output having a color that varies with view direction.

SUMMARY

In some aspects of the present description, a method of making an organic light emitting diode (OLED) display is provided. The method includes providing an OLED display panel such that each comparative display panel in a plurality of comparative display panels otherwise equivalent to the OLED display panel except for one or more values of a plurality of design parameters has a maximum white-point color shift as a view angle varies from 0 to 45 degrees of $WPCS^C_{45}$ and a white-point axial efficiency of WPAE, the plurality of comparative display panels defining a performance curve along a boundary of performance points in $WPCS^C_{45}$–$WPAE^C$ space, the performance curve extending from a first endpoint having a lowest acceptable efficiency to a second endpoint having a largest acceptable white-point color shift $WPCS_{45}^{LA}$. The providing step includes selecting the plurality of design parameters such that the OLED display panel has a maximum white-point color shift as a view angle varies from 0 to 45 degrees of $WPCS^O_{45}$ and a white-point axial efficiency of $WPAE^O$, $WPCS^O_{45}$ and $WPAE^O$ defining a performance point of the display panel being to the right of the performance curve, a distance from the performance point of the display panel to the performance curve along a $WPCS^C_{45}$ axis being at least 0.005. The method further includes disposing a color-correction component on the OLED display panel where the color-correction component is configured such that the display has a maximum white-point color shift as a view angle varies from 0 to 45 degrees of $WPCS_{45}$ and a white-point axial efficiency of WPAE, $WPCS_{45}$ and WPAE defining a performance point of the display being above or to the left of the performance curve.

In some aspects of the present description, a method of making an organic light emitting diode (OLED) display is provided. The method includes providing an OLED display panel such that each comparative display panel in a plurality of comparative display panels otherwise equivalent to the OLED display panel except for one or more values of a plurality of design parameters has a maximum white-point color shift as a view angle varies from 0 to 45 degrees of $WPCS^C_{45}$ and a white-point axial efficiency of $WPAE^C$. The providing step includes selecting the plurality of design parameters such that the OLED display panel has a maximum white-point color shift as a view angle varies from 0 to 45 degrees of $WPCS^O_{45}$ and a white-point axial efficiency of $WPAE^O$. For at least one comparative display panel, $WPCS^C_{45}$ is no more than $WPCS^O_{45}$–0.005 and $WPAE^C$ is no less than $WPAE^O$–1 Cd/A. The method further includes disposing a color-correction component on the OLED display panel where the color-correction component is configured such that the display has a white-point color shift from 0 to 45 degrees of $WPCS_{45}$, $WPCS_{45}$ being less than $WPCS^C_{45}$.

In some aspects of the present description, a method of making an organic light emitting diode (OLED) display is provided. The method includes providing an OLED display panel such that each comparative display panel in a plurality of comparative display panels otherwise equivalent to the OLED display panel except for one or more values of a plurality of design parameters has a maximum white-point color shift as a view angle varies from 0 to 45 degrees of $WPCS^C_{45}$, a white-point axial efficiency of $WPAE^C$, and a blue axial efficiency of $BAE^C$. The providing step includes selecting the plurality of design parameters such that the OLED display panel has a maximum white-point color shift as a view angle varies from 0 to 45 degrees of $WPCS^O_{45}$ and a white-point axial efficiency of $WPAE^O$. For at least one comparative display panel, $WPCS^C_{45}$ is no more than $WPCS^O_{45}$–0.005 and $WPAE^C$ is no less than $WPAE^O$–1 Cd/A. The method further includes disposing a color-correction component on the OLED display panel where the color-correction component is configured such that the display has a maximum white-point color shift from 0 to 45 degrees of $WPCS_{45}$ and a blue axial efficiency of BAE, $WPCS_{45}$ being less than $WPCS^C_{45}$+0.005, BAE being at least 10% greater than $BAE^C$.

In some aspects of the present description, an organic light emitting diode (OLED) display is provided. The display includes a pixelated OLED display panel and a color-correction component disposed on the pixelated OLED display panel. The pixelated OLED display panel has a maximum white-point color shift from 0 to 45 degrees of $WPCS^O_{45}$ and a white-point axial efficiency of $WPAE^O$. The pixelated OLED display panel includes a plurality of pixels, each pixel including a plurality of subpixels, each subpixel including a plurality of OLED layers. The color-correction component is configured such that the display has a maximum white-point color shift from 0 to 45 degrees of $WPCS_{45}$ and a white-point axial efficiency of WPAE. A plurality of comparative display panels otherwise equivalent to the pixelated OLED display panel but having one or more different optical thicknesses of the OLED layers have a maximum white-point color shift from 0 to 45 degrees of $WPCS^C_{45}$ and a white-point axial efficiency of $WPAE^C$. The plurality of comparative display panels defines a first performance curve along a boundary of performance points in $WPCS^C_{45}$–$WPAE^C$ space. A plurality of comparative displays otherwise equivalent to the display but having one or more different optical thicknesses of the OLED layers defines a second performance curve along a boundary of performance points in $WPCS^C_{45}$–WPAE space. The second performance curve is above or to the left of the first performance curve. $WPCS_{45}$ and WPAE define a performance point of the display substantially along the second performance curve. The second performance curve and the plurality of comparative displays defines a third performance curve in $WPCS^C_{45}$–$WPAE^C$ space such that for each comparative display in the plurality of comparative displays having a performance point along the second performance curve, removing the color-correction component from the comparative display results in a comparative display panel having a performance point along the third performance curve. The third performance curve is to the right of the first performance curve. $WPCS^O_{45}$ and $WPAE^O$ defines a performance point of the display panel substantially along the third performance curve.

In some aspects of the present description, an organic light emitting diode (OLED) display is provided. The display includes a pixelated OLED display panel and a color-correction component disposed on the pixelated OLED display panel. The pixelated OLED display panel has a maximum white-point color shift from 0 to 45 degrees of $WPCS^O_{45}$ and a white-point axial efficiency of $WPAE^O$. The pixelated OLED display panel including a plurality of pixels, each pixel including a plurality of subpixels, each subpixel including a plurality of OLED layers. A comparative display panel otherwise equivalent to the pixelated OLED display panel but having one or more different optical thicknesses of the OLED layers has a maximum white-point color shift from 0 to 45 degrees of $WPCS^C_{45}$ and a white-point axial efficiency of $WPAE^C$, $WPCS^C_{45}$ being no more than $WPCS^O_{45}-0.005$. The color-correction component is configured such that the display has a maximum white-point color shift from 0 to 45 degrees of $WPCS_{45}$ and a white-point axial efficiency of WPAE, $WPCS_{45}$ being less than $WPCS^C_{45}$.

In some aspects of the present description, an organic light emitting diode (OLED) display is provided. The display includes a pixelated OLED display panel and a color-correction component disposed on the pixelated OLED display panel. The pixelated OLED display panel has a maximum white-point color shift from 0 to 45 degrees of $WPCS^O_{45}$ and a white-point axial efficiency of $WPAE^O$. The pixelated OLED display panel includes a plurality of pixels, each pixel including a plurality of subpixels, each subpixel including a plurality of OLED layers. The color-correction component is configured such that the display has a maximum white-point color shift from 0 to 45 degrees of $WPCS_{45}$ and a white-point axial efficiency of WPAE. A plurality of comparative display panels otherwise equivalent to the pixelated OLED display panel but having one or more different optical thicknesses of the OLED layers have a maximum white-point color shift from 0 to 45 degrees of $WPCS^C_{45}$ and a white-point axial efficiency of $WPAE^C$. The plurality of comparative display panels defining a performance curve along a boundary of performance points in $WPCS^C_{45}$–$WPAE^C$ space, $WPCS_{45}$ and WPAE defining a performance point of the display. A blue axial efficiency BAE of the display is at least 10% greater than a blue axial efficiency $BAE^C$ of a first comparative display panel in the plurality of comparative display panels having a performance point along the performance curve and having a white-point axial efficiency within 5% of WPAE.

In some aspects of the present description, an organic light emitting diode (OLED) display is provided. The display includes a pixelated OLED display panel and a color-correction component disposed on the pixelated OLED display panel. The pixelated OLED display panel has a maximum white-point color shift from 0 to 45 degrees of $WPCS^O_{45}$ and a white-point axial efficiency of $WPAE^O$. The pixelated OLED display panel includes a plurality of pixels, each pixel including a plurality of subpixels, each subpixel including a plurality of OLED layers. A comparative display panel otherwise equivalent to the pixelated OLED display panel but having one or more different optical thicknesses of the OLED layers has a maximum white-point color shift from 0 to 45 degrees of $WPCS^C_{45}$, a white-point axial efficiency of $WPAE^C$, and a blue axial efficiency of $BAE^C$, $WPCS^C_{45}$ being no more than $WPCS^O_{45}-0.005$. The color-correction component is configured such that the display has a maximum white-point color shift from 0 to 45 degrees of $WPCS_{45}$ and a blue axial efficiency of BAE, $WPCS_{45}$ being less than $WPCS^C_{45}+0.005$, BAE being at least 10% greater than $BAE^C$.

In some aspects of the present description, an organic light emitting diode (OLED) display is provided. The display includes a pixelated OLED display panel and a color-correction component disposed on the pixelated OLED display panel. The pixelated OLED display panel has a ratio of blue-to-red color mixing weights at 30 degrees of $\beta^O_{30}$, and a ratio of blue-to-red color mixing weights at 45 degrees of $\beta^O_{45}$. $\beta^O_{45} > \beta^O_{30} \geq 1.05$ and $1.5 \geq \beta^O_{45} \geq 1.1$. The color-correction component is configured such that a ratio of blue-to-red color mixing weights at 45 degrees of the display is 1345 and a ratio of blue-to-red color mixing weights at 30 degrees of the display is $\beta_{30}$. $\beta^O_{45}-0.1 \geq \beta_{45} \geq 2.1-\beta^O_{45}$ and $\beta^O_{30}-0.05 \geq \beta_{30} \geq 2.05-\beta^O_{30}$.

In some aspects of the present description, an organic light emitting diode (OLED) display is provided. The display includes a pixelated OLED display panel and a color-correction component disposed on the pixelated OLED display panel. The pixelated OLED display panel includes a plurality of pixels, each pixel including a plurality of subpixels, each subpixel including a plurality of OLED layers. The color-correction component is configured such that the display has a maximum blue-point color shift as a view angle varies from 0 to 45 degrees of $BPCS_{45}$ and a blue axial efficiency of BAE. A first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$. $BPCS^{C1}_{45}$ is within 0.0025 of $BPCS_{45}$ and BAE is at least 10% greater than $BAE^{C1}$; or BAE is within 5% of BAE and $BPCS^{C1}_{45}$ is at least 0.005 greater than $BPCS_{45}$.

BRIEF DESCRIPTION OF THE DRAWINGS

FIG. 3C is a schematically illustrates regions to the left and right of the performance curve of FIG. 3B;

FIG. 3D schematically illustrates of regions above and below the performance curve of FIG. 3B;

FIG. 4A schematically illustrates a performance curve and a modified performance curve;

FIG. 4B schematically illustrates the modified performance curve of FIG. 4A;

DETAILED DESCRIPTION

Figure 1:
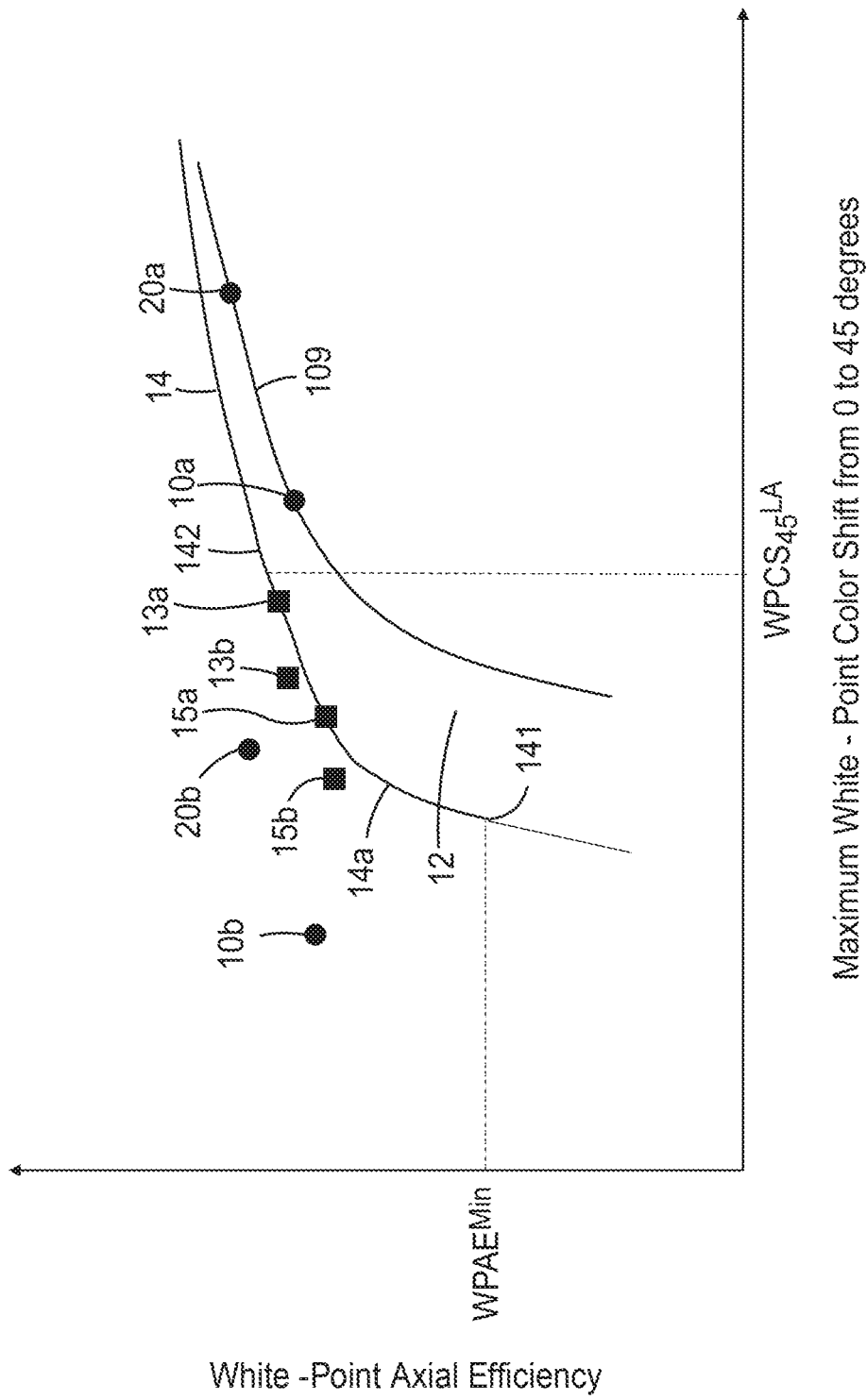
FIG. 1 is a schematic plot of a white-point axial efficiency versus white-point color shift performance space.

In the following description, reference is made to the accompanying drawings that form a part hereof and in which various embodiments are shown by way of illustration. The drawings are not necessarily to scale. It is to be understood that other embodiments are contemplated and may be made without departing from the scope or spirit of the present description. The following detailed description, therefore, is not to be taken in a limiting sense.

Organic light emitting diode (OLED) displays often produce a light output having a color that varies with view direction. This effect is particularly objectionable in strong cavity OLEDs where a cavity between the cathode and anode of the emissive stack of the OLED has an output that depends on wavelength and view angle approximately as the cosine of the view angle in the cavity divided by the wavelength of the light in the cavity. The color shift and an efficiency of the OLED display depends on design parameters of the OLED display. For example, both the color shift and the efficiency depends on the thickness and materials of layers of the OLED display. In conventional OLED displays, the OLED layers are chosen to achieve a desired compromise between color shift and efficiency.

As described in U.S. Prov. Appl. Nos. 62/342,620 (Freier et al.) and 62/414,127 (Erickson et al.), and in PCT Publication No. WO 2017/205174 (Freier et al.), a color-correction component, such as an optical stack including a nanostructured interface, can be placed proximate an emissive layer of an OLED display panel to reduce the variation in color with view direction without substantially changing the on-axis light output of the display. Other useful color-correction components include partial reflectors which, for example, provides a wavelength dependent reflectivity and transmissivity. Useful partial reflectors are described in U.S. Prov. Appl. Nos. 62/566,654 (Haag et al.) and 62/383,058 (Benoit et al.) and 62/427,450 (Benoit), for example. Other useful color-correction components include polymeric films, which function, for example, as moderate optical diffusers. Useful polymeric films are described in U.S. patent application Ser. No. 15/587,929 (Hao et al.) and Ser. No. 15/587,984 (Hao et al.), for example.

The color-correction component can be placed adjacent a top surface of a top emitting OLED or adjacent a bottom surface of a bottom emitting OLED. The OLED may be a strong-cavity OLED or a weak-cavity OLED or a no-cavity OLED. Current OLED markets are dominated by active-matrix organic light-emitting diode (AMOLED) displays, which have a top-emissive architecture and currently do not use any light extraction method except for employing a strong microcavity design. This strong cavity design can have high light efficiency, but the angular color uniformity is much worse than that of liquid crystal displays (LCDs), for example. In some embodiments of the present description, the color-correction component is advantageously used with a strong-cavity OLED, such as an AMOLED, because of the relatively large color shifts typically present in a strong-cavity OLED.

In some embodiments, an OLED display includes an encapsulant disposed on emissive layers and a circular polarizer disposed adjacent the encapsulant. In some embodiments, the color-correction component is disposed between the encapsulant and the circular polarizer.

There are several variables that can be used to quantify the reduction in the variation in color with view direction. For example, a shift in color with view angle from a specified color on axis can be used to characterize the color shift. Different specified on-axis color provides different quantities to characterize the color shift. It has been found that specifying a white axial color provides a useful quantity characterizing the overall color shift performance. In particular, a useful quantity to characterize the color shift is the maximum white-point color shift of the display as the view angle varies from zero to 45 degrees ($WPCS_{45}$). Another quantity that is useful in characterizing the display is maximum blue-point color shift as a view angle varies from 0 to 45 degrees of ($BPCS_{45}$). The view angle refers to the angle relative to a direction normal to the display as determined in air external to the display. The corresponding angles relative to the normal direction in interior layers of the display can be determined by Snell's law. If the display is curved, the normal direction refers to the normal direction at the pixel emitting the light being characterized.

The white-point color shift with view angle can be described in terms of a CIE (Commission Internationale de l'Eclairage) 1976 UCS (Uniform Chromaticity Scale) chromaticity diagram. The white-point color shift at a specified view angle is the chromaticity distance between the light output at the specified view angle and the light output at a zero-degree (normal to the display) view angle when the light output at a zero-degree view angle is white. Chromaticity distance refers to the Euclidean distance between two points in the CIE chromaticity diagram. For example, if a first color has CIE 1976 UCS color coordinates ($u'_1$, $v'_1$) and a different second color has CIE 1976 UCS color coordinates ($u'_2$, $v'_2$), the chromaticity distance between the two colors is given by the positive square root of $(\Delta u'v')^2 = (u'_2 - u'_1)^2 + (v'_2 - v'_1)^2$. The white point at the normal viewing angle can be any suitable white point. For example, the white point can be taken to be the white point of a standard illuminant or can be taken to be the white point produced by the display panel. The white point can be specified in u',v' coordinates. For example, one suitable white point is u'=0.19783 and v'=0.46833. Other example suitable white points are given in the Table 1 which gives the CIE x, y, u' and v' coordinates for standard illuminants and for white light produced from common displays and gives the correlated color temperature (CCT) for standard illuminants.

TABLE 1

| Illuminant | x | y | u' | v' | CCT | Description |
|---|---|---|---|---|---|---|
| A | 0.44757 | 0.40745 | 0.25596 | 0.52429 | 2856 | Incandescent/Tungsten |
| D65 | 0.31271 | 0.32902 | 0.19783 | 0.46833 | 6504 | Noon Daylight |
| E | 0.33333 | 0.33333 | 0.21053 | 0.47368 | 5454 | Equal Energy |
| F2 | 0.37208 | 0.37529 | 0.22019 | 0.49970 | 4230 | Cool White Fluorescent |
| Samsung Galaxy S ® 6 | 0.313 | 0.325 | 0.19955 | 0.46621 | | |
| Apple Watch ® | 0.308 | 0.322 | 0.19718 | 0.46383 | | |
| Apple iPhone ® 6 | 0.307 | 0.322 | 0.19648 | 0.46368 | | |

TABLE 1-continued

The blue-point color shift at a specified view angle is similarly defined as the chromaticity distance between the light output at the specified view angle and the light output at a zero-degree (normal to the display) view angle when the light output is from the blue subpixels of the display.

It is also desired to characterize the brightness and/or the efficiency of the display. A useful quantity to characterize the on-axis brightness is the white-point axial efficiency of the display (WPAE). Another quantity that is useful in characterizing the display is blue axial efficiency (BAE). The BAE is the efficiency of the blue subpixels when the display produces a white light output (e.g., any of the white-points described elsewhere herein). The lifetime of an OLED display is typically limited by the lifetime of the blue subpixels. Increasing the BAE can therefore increase the lifetime of the OLED display. The efficiencies refer to the luminous intensity produced per unit of current supplied and can be expressed in cd/A.

According to the present description, it has been found that simultaneously designing the OLED stack and the color-correcting component, or designing the OLED stack based at least in part on properties of the color-correcting component, can provide performance benefits beyond what can be obtained by first designing the OLED stack to provide a desired compromise between color shift and efficiency and then using a color-correction component to further correct the color shift. For example, it has been found according to some embodiments that when the layers of an OLED stack are selected to deliberately create an imbalance in color mixing weights of the OLED display panel and a color-correction component is used to at least partially correct this imbalance, the resulting display has a performance (e.g., increased efficiency and/or reduced color shift) that cannot be achieved by placing the color-correction component on a conventional display panel. This imbalance in color mixing weights can be selected based, at least in part, on optical properties that can be achieved by a suitable selection of the color-correction component. According to some embodiments, the result of this is to create a brighter display (e.g., higher WPAE) than conventional OLED displays that also provides at least as good a color shift (e.g., $WPCS_{45}$ is not increased) as conventional OLED displays; or to create a display that has an improved color shift (e.g., decreased $WPCS_{45}$ and/or decreased $BPCS_{45}$) compared to conventional displays that also provides at least as good a brightness (e.g., WPAE is not decreased and/or BAE is not decreased); or to create a display that has an improved blue axial efficiency compared to conventional display panels that also provides a similar or improved color shift (e.g., $WPCS_{45}$ is not substantially increased and/or $BPCS_{45}$ is not increased). More generally, according to some embodiments, it has been found that simultaneously designing the OLED stack and the color-correcting component, or designing the OLED stack in view of the properties of the color-correcting component, provides a color-shift/efficiency performance space that cannot be achieved by applying a color-correcting component to a conventional OLED display panel. According to some embodiments, it has been found that simultaneously designing the OLED stack and the color-correction component or designing the OLED stack in view of the color-correction component can result in an increased BAE. In some embodiments, the preferred design may be to allow a modest increase in white-point color shift in favor of increasing a blue axial efficiency.

Denote by $WPCS^O_{45}$ the maximum white-point color shift from 0 to 45 degrees of the display panel without the color-correcting component, $WPCS^C_{45}$ the maximum white-point color shift from 0 to 45 degrees of a comparative display panel, $WPCS_{45}$ the maximum white-point color shift from 0 to 45 degrees of the OLED display including the color-correcting component, $WPAE^O$ the white-point axial efficiency of the display panel without the color-correcting component, $WPAE^C$ the white-point axial efficiency of the comparative display panel, WPAE the white-point axial efficiency of the OLED display including the color-correcting component, $BAE^C$ the blue axial efficiency of the comparative display panel, BAE the blue axial efficiency of the OLED display including the color-correcting component, $BPCS^O_{45}$ the maximum blue-point color shift as a view angle varies from 0 to 45 degrees of the display panel without the color-correcting component, $BPCS^C_{45}$ the maximum white-point color shift from 0 to 45 degrees of a comparative display panel, and $BPCS_{45}$ the maximum white-point color shift from 0 to 45 degrees of the OLED display including the color-correcting component. It has been found, according to some embodiments, that designing an OLED stack to provide a less desirable or even ordinarily unacceptable white-point or blue-point color shift results in a performance improved in at least one way in $WPCS_{45}$–WPAE–$BPCS_{45}$–BAE space (e.g., $WPCS_{45} < WPCS^C_{45}$ and/or $WPAE > WPAE^C$ and/or $BAE > BAE^C$ and/or $BPCS_{45} < BPCS^C_{45}$) when the color-correcting component is included.

Another advantage of the displays of present description is an improved tolerance to manufacturing variations, according to some embodiments. For example, according to some embodiments, it has been found that variations in layer thicknesses due to imperfect thickness control manufacturing, for example, results in variations in the performance in $WPCS_{45}$–WPAE that are significantly smaller than in conventional display panels.

FIG. 1 is a plot schematically illustrating a performance space 12 in WPAE–$WPCS_{45}$ coordinates. The performance space 12 includes points on or below and to the right of the performance curve 14 and represents performance points achievable by varying one or more design parameters of the comparative display panels. Since comparative display panels, the display panels of the present description, and OLED displays including the display panels and color-correcting components of the present description can be illustrated on the same plot, the x- and y-axes of the plot will be referred to interchangeably as $WPCS^C_{45}$–$WPAE^C$ axes, $WPCS^O_{45}$–$WPAE^O$ axes, and $WPCS_{45}$–WPAE axes. For a given OLED display panel, a plurality of comparative display panels can be defined which are otherwise equivalent to the OLED display panel except for one or more values of a plurality of design parameters. The comparative display panel define performance points in the $WPCS^C_{45}$–$WPAE^C$ space and define the performance curve 14 along the boundary of performance points. In particular, the performance curve 14 is the upper left-hand portion of the boundary of performance points. Different points along the performance curve 14 represent different performance results that can be realized by appropriate choices of the design parameters. If a performance point falls on the performance curve 14, there is no choice of the design parameters which results in a lower $WPCS^C_{45}$ without also lowering $WPAE^C$, or which results in a higher $WPAE^C$ without also increasing $WPCS^C_{45}$.

There is typically a largest acceptable maximum white-point color shift for view angles from 0 to 45 degrees of $WPCS_{45}^{LA}$ and a minimum acceptable axial efficiency $WPAE^{Min}$ that may depend on the application (e.g., one or both of these quantities may be different for cell phones than for televisions). In some embodiments, the plurality of comparative display panels has a range of $WPAE^C$ that extends both below and above $WPAE^{Min}$ and a range of $WPCS^C_{45}$ that extends both below and above $WPCS_{45}^{LA}$. In some embodiments, a range of $WPCS^C_{45}$ extends at least from 0.01 to 0.015. In some such embodiments, the range of $WPCS^C_{45}$ extends to at least 0.02, or at least from 0.009 to at 0.015, or at least from 0.008 to 0.02, for example. In some embodiments, the range of $WPAE^C$ extends at least from 30 cd/A to 35 cd/A, or 25 cd/A to 35 cd/A, or 35 cd/A to 40 cd/A, or 40 cd/A to 45 cd/A. In some embodiments, the range of $WPAE^C$ extends over at least 5 cd/A or at least 10 cd/A. If one were to choose a performance point without reference to a color-correcting component, one would choose a point along the performance curve 14 having a white-point axial efficiency greater than $WPAE^{Min}$ and having a maximum white-point color shift for view angles from 0 to 45 degrees less than $WPCS_{45}^{LA}$. For example, one might choose the performance point 15a as a desired compromise between efficiency and color shift. A color correction component can then be added to reduce the color shift to performance point 15b. The portion of the performance curve 14 extending between a first endpoint 141 where the white-point axial efficiency is $WPAE^{Min}$ and a second endpoint 142 where the maximum white-point color shift for view angles from 0 to 45 degrees is $WPCS_{45}^{LA}$ is the performance curve 14a. The performance curve 14a is defined by a plurality of comparative display panels being the subset of the plurality of comparative display panels defining the performance curve 14 having a white-point axial efficiency of at least $WPAE^{Min}$ and a maximum white-point color shift for view angles from 0 to 45 degrees of no more than $WPCS_{45}^{LA}$. The first and second endpoints may alternatively be chosen such that the maximum white-point color shift for view angles from 0 to 45 degrees extends over any of the ranges described elsewhere herein and/or such that the white-point axial efficiency extends over any of the ranges described elsewhere herein.

According to the present description, it has been found that designing the OLED panel to consider the effects of the color-correction component can provide improved results compared to using a color-correction on a conventionally designed OLED panel. Since we are interested in optimizing the results for the display having the color-correction component disposed on the display panel, the optimum choice for the performance point of the display panel may be below and to the right of the performance curve 14, though in some cases it may also be on the performance curve 14. For example, in some embodiments, performance point 10a for a display panel translates to performance point 10b when a color-correction component is included and no other performance points for the display panel results in a lower white-point color shift without also sacrificing another desired performance attribute such as efficiency. Note that performance point 10a is below and to the right of performance curve 14 and that there is a comparative display panel having a performance point 13a which has both an improved white-point axial efficiency and an improved white-point color shift compared to performance point 10a. When a color-correction component is included, the performance point 13a is shifted to performance point 13b, while performance point 10a is shifted to performance points 10b which has a substantially lower white-point color shift than performance point 13b.

As another example, performance point 20a is shifted to performance point 20b when a color-correction component is included. Performance point 20b has a white-point color shift that is roughly comparable to that of performance points 15b and 13b, but has a significantly higher white-point axial efficiency.

In some embodiments, the performance points which result in optimum performance of the resulting display, which includes the display panel and the color correction component, is along a performance curve 109 which is to the right of performance curve 14a.

In some embodiments, the color-correction component shifts the maximum white-point color shift from 0 to 45 degrees of the display panel to the left by at least 0.005, or at least 0.01, or at least 0.015. In other words, in some embodiments, $WPCS_{45}^{o}-WPCS_{45} \geq 0.005$, or $WPCS_{45}^{o}-WPCS_{45} \geq 0.01$, or $WPCS_{45}^{o}-WPCS_{45} \geq 0.015$. In some embodiments, values of the design parameters of the OLED display panel are selected such that $WPCS_{45}^{o}$ is at least 0.012, or at least 0.015, or at least 0.016, or at least 0.017, or at least 0.018, or at least 0.019, or at least 0.02. In some embodiments, $WPCS_{45}$ is no more than 0.014, or no more than 0.012, or no more than 0.01, or no more than 0.008, or no more than 0.006, or no more than 0.005. In some embodiments, $WPCS_{45}^{o}$ is at least 0.017 and $WPCS_{45}$ is no more than 0.01. In some embodiments, $WPCS_{45}^{o}$ is at least 0.020 and $WPCS_{45}$ is no more than 0.014. In some embodiments, $WPCS_{45}$ is no more than $WPCS_{45}^{C}-0.005$, or no more than $WPCS_{45}^{C}-0.01$, or no more than $WPCS_{45}^{C}-0.015$. In some embodiments, $WPCS_{45}^{C}$ is no more than $WPCS_{4}^{o}-0.005$, or no more than $WPCS_{4}^{o}-0.01$, or no more than $WPCS_{4}^{o}-0.015$. In some embodiments, $WPCS_{45}$ is no more than $WPCS_{45}-0.005$ and $WPCS_{45}^{C}$ is no more than $WPCS_{4}^{o}-0.005$. In some embodiments, $WPCS_{45}$ is no more than $WPCS_{45}^{C}-0.01$ and $WPCS_{45}^{C}$ is no more than $WPCS_{4}^{o}-0.01$.

Note that in FIG. 1 the efficiency of each display including the color-correction component is slightly less than the efficiency of the display without the color-correction component. This can occur due to less than perfect transmission (e.g., due to absorption or due to scattering) through the color-correction component at normal incidence. For example, the color-correction components of PCT Publication No. WO 2017/205174 (Freier et al.) have been found to typically drop the WPAE by 1.1 to 1.3 cd/A due primarily to absorption. According to the present description, this small drop in efficiency can be more than compensated by choosing design parameters for the OLED display panel such that it has a performance point with a higher efficiency (e.g., performance point 20a) even if the color-shift of the display panel without the color-correction component would have ordinarily been considered unacceptable (e.g., $WPCS_{45}^{o}>WPCS_{45}^{LA}$). In some embodiments, WPAE is at least 35 cd/A, or at least 40 cd/A, or at least 43 cd/A, or at least 45 cd/A.

In some embodiments, a performance point for a display may be selected to have a higher white-point color shift than a comparative display panel, in favor of another attribute. For example, in some embodiments, performance point 20b may be preferred over performance point 10b due to the higher efficiency, while in other embodiments, performance point 10b may be preferred due it its lower color shift. As another example, a display having a performance point with both a lower WPAE and a higher $WPCS_{45}$ than a comparative display may be preferred over the comparative display if the blue axial efficiency (BAE) of the display is higher than a blue axial efficiency of the comparative display ($BAE^{C}$). In some embodiments, BAE is at least 5%, or at least 10%, or at least 20%, or at least 30%, or at least 40%, or at least 50% greater than $BAE^{C}$.

In some embodiments, the efficiency (WPAE or BAE) of the display is greater than that of a comparative display panel, but the white-point color shift may not be less than the white-point color shift of the comparative display panel. For example, in some embodiments, $WPCS_{45}^{C}$ is no more than $WPCS_{45}^{o}-0.005$, $WPAE^{C}$ is no less than $WPAE^{o}-1$ cd/A, $WPCS_{45}$ is less than $WPCS_{45}^{C}+0.005$, and BAE is at least 10% greater than $BAE^{C}$. In some such embodiments, and in other embodiments, $WPCS_{45}$ is no more than $WPCS_{45}^{C}$, or no more than $WPCS_{45}^{C}-0.005$, or no more than $WPCS_{45}^{C}-0.01$, or no more than $WPCS_{45}^{C}-0.015$.

Figure 2:
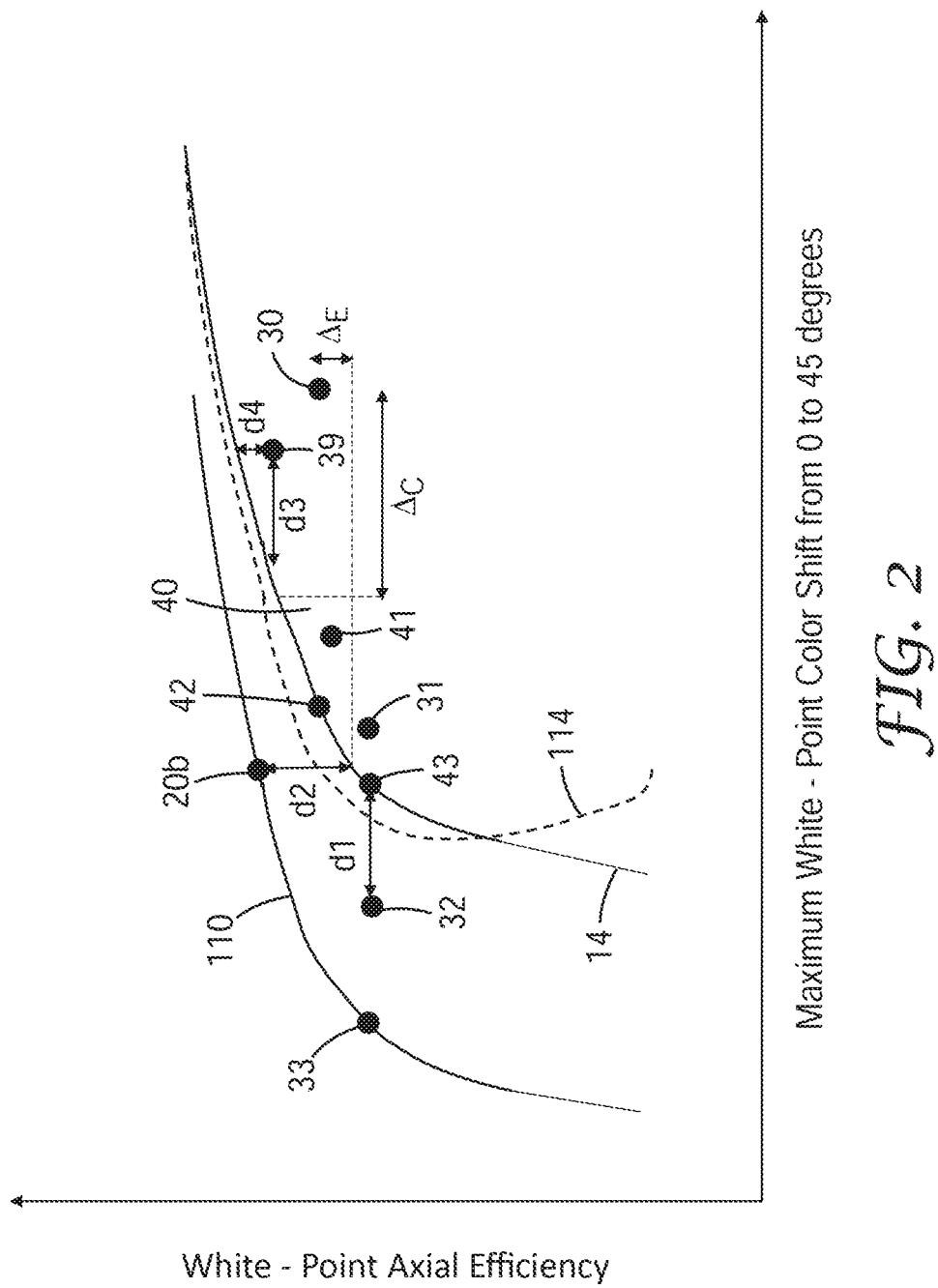
FIG. 2 is a schematic plot of the performance space of FIG. 1 and an extended performance space.

FIG. 2 is a plot schematically illustrating the performance curve 14, a modified performance curve 114, and an improved performance curve 110. The color-correction component and comparative display panels in the plurality of comparative display panels having performance points along the performance curve 14 define the modified performance curve 114, as described further elsewhere herein, since the color-correction component shifts the performance points of the comparative display panels. It has been found that in some embodiments the modified performance curve 114 is above and to the left of the performance curve 14 in some regions but is to the right of the performance curve 14 in other regions as schematically illustrated in FIG. 2. In some embodiments, the color-correction component reduces the white-point color shift for some comparative display panels along the performance curve 14 but increases the white-point color shift for other comparative display panels. The improved performance curve 110 represents a boundary of the set of performance points that can be achieved according to some embodiments of the present description. In some embodiments, the modified performance curve 114 appears differently than that depicted in FIG. 2. For example, in some embodiments, the region where the color-correction component decreases the white-point color shift may not extend to large $WPCS_{45}^{C}$ as illustrated in FIG. 2.

In some embodiments, a plurality of comparative displays otherwise equivalent to the display but having one or more different optical thicknesses of the OLED layers defines a second performance curve (e.g., improved performance curve 110) along a boundary of performance points in $WPCS_{45}^{C}-WPAE^{C}$ space, the second performance curve being above or to the left of the first performance curve (e.g., performance curve 14a). In some embodiments, the second performance curve and the plurality of comparative displays defines a third performance curve (e.g., performance curve 109) in $WPCS_{45}^{C}-WPAE^{C}$ space such that for each comparative display in the plurality of comparative displays having a performance point along the second performance curve, removing the color-correction component from the comparative display results in a comparative display panel having a performance point along the third performance curve. The third performance curve (e.g., performance curve 109) may be to the right of the first performance curve (e.g., performance curve 14a). In some embodiments, $WPCS_{45}$ and WPAE defines a performance point of the display substantially along the second performance curve and $WPCS_{45}^{o}$ and $WPAE^{o}$ defining a performance point of the display panel substantially along the third performance curve. A performance point of a display or display panel being substantially along a performance curve in this context means that there is a point on the performance curve where the maximum white-point color shift from 0 to 45 degrees of the display or display panel, respectively, is within 0.0025 of the color shift of the point and that the white-point axial efficiency of the display or display panel, respectively, is within 5% of the white-point axial efficiency of the point. In some embodiments, when a performance point of a display or display panel is described as substantially along a performance curve, there is a point on the performance curve where the maximum white-point color shift from 0 to 45 degrees of the display or display panel, respectively, is within 0.001 of the color shift of the point and where the white-point axial efficiency of the display or display panel, respectively, is within 2% of the white-point axial efficiency of the point. In some embodiments, when a performance point of a display or display panel is described as substantially along a performance curve, there is a point on the performance curve where the maximum white-point color shift from 0 to 45 degrees of the display or display panel, respectively, is within 0.0005 of the color shift of the point and where the white-point axial efficiency of the display or display panel, respectively, is within 1% of the white-point axial efficiency of the point. For any given display panel of the present description, it may be useful to refer to a comparative display panel in a particular set of comparative design panels. For example, a performance point 30 (having coordinates of $WPCS^O_{45}$ and $WPAE^O$) of a display panel is illustrated in FIG. 2. The set of points 40 are performance points of comparative display panels having a $WPCS^C_{45}$ of no more than $WPCS^O_{45}-\Delta_C$ and a $WPAE^C$ being no less than $WPAE^O-\Delta_E$. Useful values for $\Delta_C$ include 0.005 or 0.01. Useful values for $\Delta_E$ include 1 cd/A or 0.5 cd/A or in a range of about 1 to about 2 cd/A. Performance points 41 and 42 of comparative display panels are illustrated. The particular comparative display panel chosen for comparison with the display panel may be referred to as the first comparative display panel. In some embodiments, there is at least one comparative display panel in the plurality of comparative display panels having a performance point 42 along the performance curve having coordinates ($WPCS^C_{45}$, $WPAE^C$), where $WPCS^C_{45}$ is no more than $WPCS^O_{45}-\Delta_C$, $WPAE^C$ is no less than $WPAE^O-\Delta_E$, and $WPCS_{45}$ is less than $WPCS^C_{45}$. In some embodiments, $\Delta_C$=0.005 and $\Delta_E$=1 cd/A. An upper limit in efficiency can also be specified. For example, $WPAE^C$ may be specified to be in a range of $WPAE^O-\Delta_E$ to $WPAE^O+\Delta_E$. Instead of specifying 4E as an absolute number, it may also be specified as a percent of any one of $WPCS^C_{45}$, $WPCS^C_{45}$, or $WPCS^C_{45}$. For example, in some embodiments, the range of $WPCS^C_{45}$ is specified to be within 5%, or 2%, or 1% of WPAE. In some embodiments, the comparative display panel chosen (the first comparative display panel) has a white-point axial efficiency equal to WPAE.

Some possible performance points ($WPCS_{45}$, WPAE) of the display are illustrated as performance points 31, 32, 33 and 43. Performance points 31 and 43 in $WPCS_{45}$-WPAE space can be achieved using a conventional OLED display panel without using a color-correction component. However, the display of the present description having performance point 31 or 43 has another performance attribute (e.g., blue axial efficiency) that is improved over that of the conventional OLED display having the same or similar $WPCS_{45}$-WPAE coordinates. For example, in some embodiments, a display panel (e.g., having performance point 31) has a blue axial efficiency at least 5%, or at least 10%, or at least 20%, or at least 30%, or at least 40%, or at least 50% greater than a blue axial efficiency $BAE^C$ of a first comparative display panel in the plurality of comparative display panels having a performance point along the performance curve and having a white-point axial efficiency within 5% of WPAE. In some embodiments, the first comparative display panel has $WPCS^C_{45}$-$WPAE^C$ coordinates given by performance point 43 and the OLED display having the color-correction component has $WPCS_{45}$-WPAE coordinates given by performance point 31, or by performance point 43, but the display has a blue axial efficiency at least 10% greater than that of the first comparative display panel.

Performance points 32 and 33 represent performance that cannot be achieved by placing the color-correcting component on display panels having performance points along the performance curve 14. Performance point 33 has a lower white-point color shift than performance point 32 and so would typically be preferred over performance point 32 in embodiments where a low white-point color shift is a primary concern. However, in some embodiments, a display having the performance point 32 may have a higher blue axal efficiency and so may be preferred in embodiments where a high blue axial efficiency is a primary concern.

In some embodiments, $WPCS^O_{45}$ and $WPAE^O$ define a performance point ($WPCS^O_{45}$, $WPAE^O$) of the display panel which is below and to the right of the performance curve 14. In some embodiments, $WPCS_{45}$ and WPAE define a performance point ($WPCS_{45}$, WPAE) of the display being above or to the left of the modified performance curve 114. In some embodiments, ($WPCS_{45}$, WPAE) is above and to the left of the performance curve 14. In some embodiments, ($WPCS_{45}$, WPAE) is above and to the left of the performance curve 14 and is above or to the left of the modified performance curve 114. In some embodiments, a distance from $WPCS_{45}$ to the performance curve 14 or to the modified performance curve 114 along a $WPCS^C_{45}$ axis of the plot of $WPAE^C$ versus $WPCS^C_{45}$ is at least 0.002 or 0.005. For example, the distance d1 between the performance point 32 and the performance curve 14 may be at least 0.002, or at least 0.0025, or at least 0.005, or at least 0.0075, or at least 0.01. In some embodiments, a smallest distance from WPAE to the performance curve 14 or to the modified performance curve 114 along a $WPAE^C$ axis of the plot of $WPAE^C$ versus $WPCS^C_{45}$ is at least 0.5 cd/A or at least 1.0 cd/A. For example, a distance d2 from performance point 20b to the performance curve 14 may be at least 0.5 cd/A or at least 1.0 cd/A. The distance from the performance point 20b to the performance curve 14 or to the modified performance curve 114 along the $WPCS^C_{45}$ axis of the plot of $WPAE^C$ versus $WPCS^C_{45}$ may be at least 0.002, or 0.0025, or 0.005, or 0.0075, or 0.01. In some embodiments, a distance from $WPCS^O_{45}$ to the performance curve 14 along the $WPCS^C_{45}$ axis of the plot of $WPAE^C$ versus $WPCS^C_{45}$ is at least 0.002 or at least 0.005. In some embodiments, a distance from $WPAE^O$ to the performance curve 14 along the $WPAE^C$ axis of the plot of $WPAE^C$ versus $WPCS^C_{45}$ is at least 0.5 cd/A or at least 1.0 cd/A. For example, a distance d3 from performance point 39 to the performance curve 14 may be at least 0.002 or at least 0.005 and a distance d4 from performance point 39 to the performance curve 14 may be at least 0.5 cd/A or at least 1 CD/A.

Figure 33:
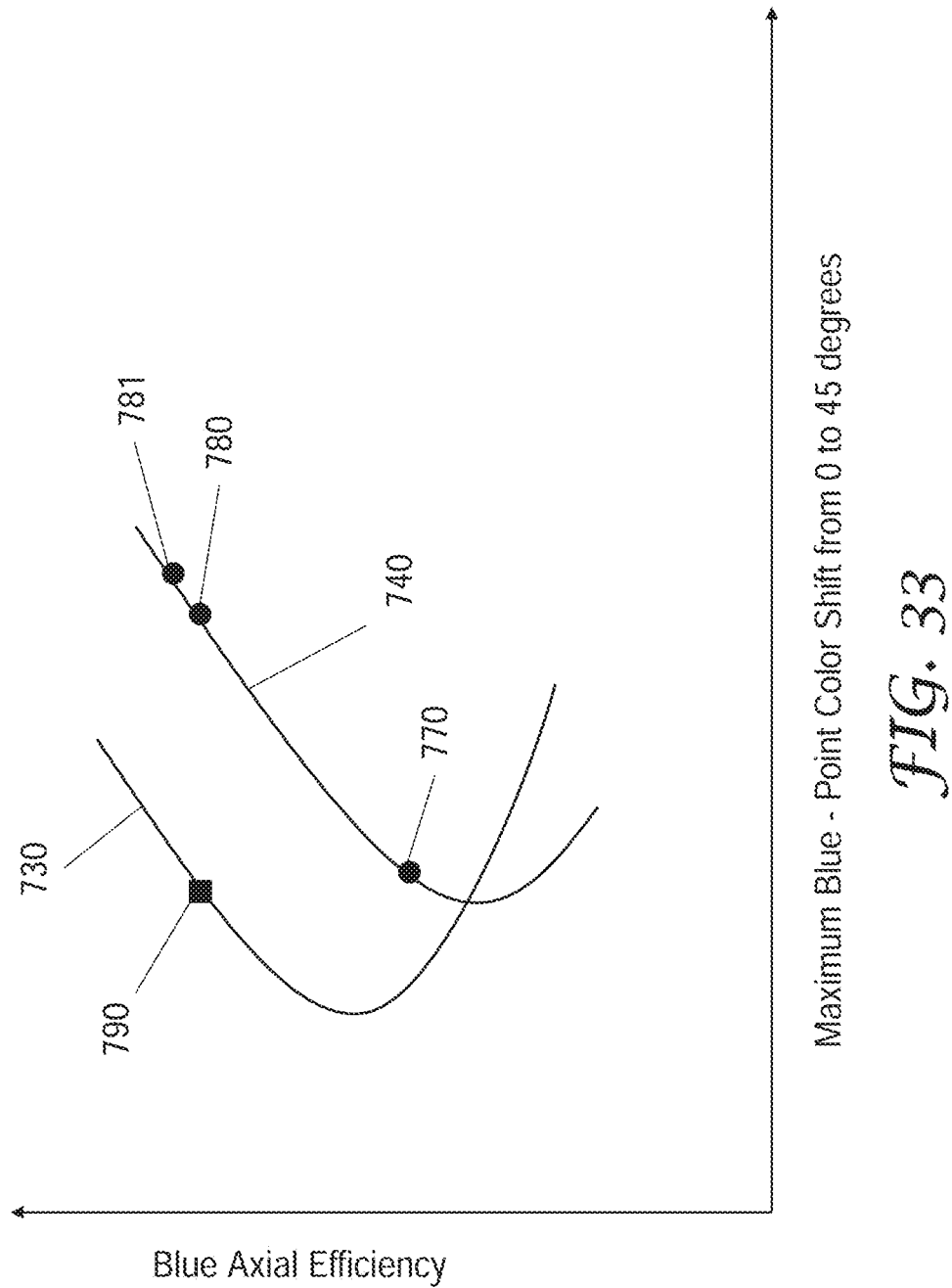
FIG. 33 is a schematic plot of blue axial efficiency versus maximum blue-point color shift.

In some embodiments, it is convenient to characterize the performance of the display and display panel in terms a plot of the blue axial efficiency versus the maximum blue-point color shift instead of or in addition to a plot of the white-point axial efficiency versus the maximum white-point color shift. FIG. 33 is a schematic plot of the blue axial efficiency versus the maximum blue-point color shift as a view angle varies from 0 to 45 degrees for displays (along curve 730) including a color correction component and for display panels (along curve 740) not including the color correction component. A performance point 790 of a display and performance points of comparative display panels 770 and 780 are illustrated. In some embodiments, an OLED display includes a pixelated OLED display panel including a plurality of pixels, each pixel including a plurality of subpixels, each subpixel including a plurality of OLED layers; and a color-correction component disposed on the pixelated OLED display panel, the color-correction component configured such that the display has a maximum blue-point color shift as a view angle varies from 0 to 45 degrees of $BPCS_{45}$ and a blue axial efficiency of BAE. In some embodiments, a first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$, where $BPCS^{C1}_{45}$ is within 0.0025 of $BPCS_{45}$ and BAE is at least 10% greater than $BAE^{C1}$. For example, the first comparative display panel may have a performance point 770 which has $BPCS^{C1}_{45}$ approximately equal to the $BPCS_{45}$ of the display having performance point 790 and where BAE of the display having the performance point 790 is substantially greater than the $BAE^{C1}$ of the first comparative display panel having performance point 770. In some embodiments, $BPCS^{C1}_{45}$ is within 0.001 of $BPCS_{45}$ and BAE is at least 15%, or at least 20%, or at least 25% greater than $BAE^{C1}$. In some embodiments, a first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$, where $BAE^{C1}$ is within 5% of BAE and $BPCS^{C1}_{45}$ is at least 0.005 greater than $BPCS_{45}$. For example, the first comparative display panel may have a performance point 780 which has $BAE^{C1}$ approximately equal to the BAE of the display having performance point 780 and where $BPCS_{45}$ of the display having the performance point 790 is substantially less than the $BPCS^{C1}_{45}$ of the first comparative display panel having performance point 780. In some embodiments, BAE is within 2% of BAE and $BPCS^{C1}_{45}$ is at least 0.0075, or at least 0.01, or at least 0.015 greater than $BPCS_{45}$.

In some embodiments, $BPCS^{C1}_{45}$ is within 0.0025 of $BPCS_{45}$ and BAE is at least 10% greater than $BAE^{C1}$ (e.g., for a first comparative display panel having performance point 770), and a second comparative display panel otherwise equivalent to the pixelated OLED display panel but having one or more different optical thicknesses of the OLED layers has a maximum blue-point color shift as a view angle varies from 0 to 45 degrees of $BPCS^{C2}_{45}$ and a blue axial efficiency of $BAE^{C2}$ (e.g., for a second comparative display panel having performance point 780), $BAE^{C2}$ being within 5% of BAE and $BPCS^{C2}_{45}$ being at least 0.005 greater than $BPCS_{45}$. In some embodiments, $BPCS^{C1}_{45}$ is within 0.001 of $BPCS_{45}$ and BAE is at least 15% greater than $BAE^{C1}$, and a second comparative display panel otherwise equivalent to the pixelated OLED display panel but having one or more different optical thicknesses of the OLED layers has a maximum blue-point color shift as a view angle varies from 0 to 45 degrees of $BPCS^{C2}_{45}$ and a blue axial efficiency of $BAE^{C2}$, $BAE^{C2}$ being within 2% of BAE and $BPCS^{C2}_{45}$ being at least 0.0075 greater than $BPCS_{45}$.

In some embodiments, the pixelated OLED display panel has a maximum blue-point color shift as a view angle varies from 0 to 45 degrees of $BPCS^0_{45}$ and a blue axial efficiency of $BAE^0$. For example, ($BPCS^0_{45}$, $BAE^0$) may be the performance point 781 which results in the performance point 790 when the color correction component is disposed on the display panel.

To generally describe what is meant by above/below or left/right of a performance curve, we consider general possible shapes of extended performance spaces that includes regions of $WPAE^C$–$WPCS^C_{45}$ that would ordinarily not be considered.

Figure 3A:
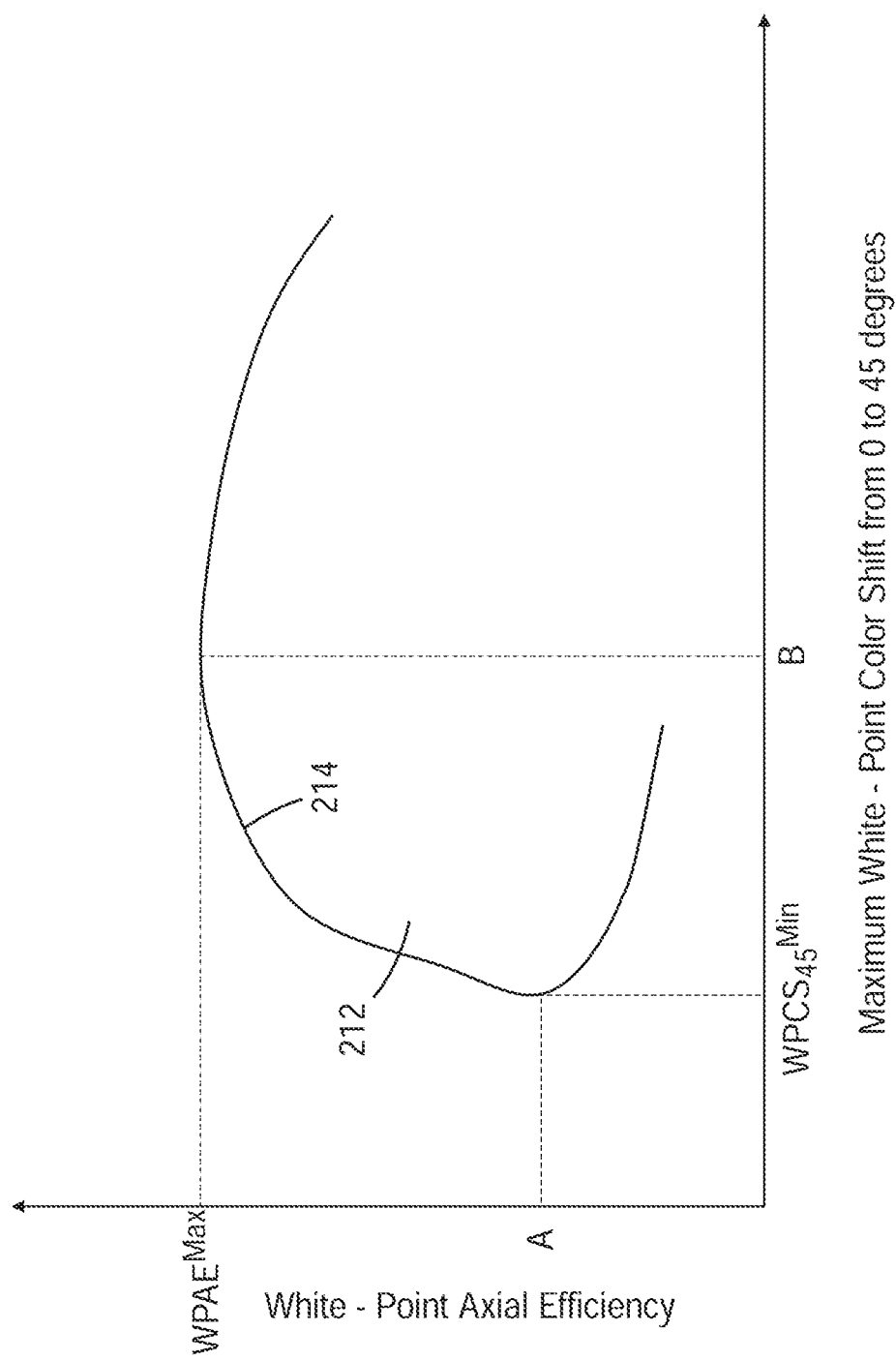
FIG. 3A is a schematic plot illustrating an extended performance space.
Figure 3B:
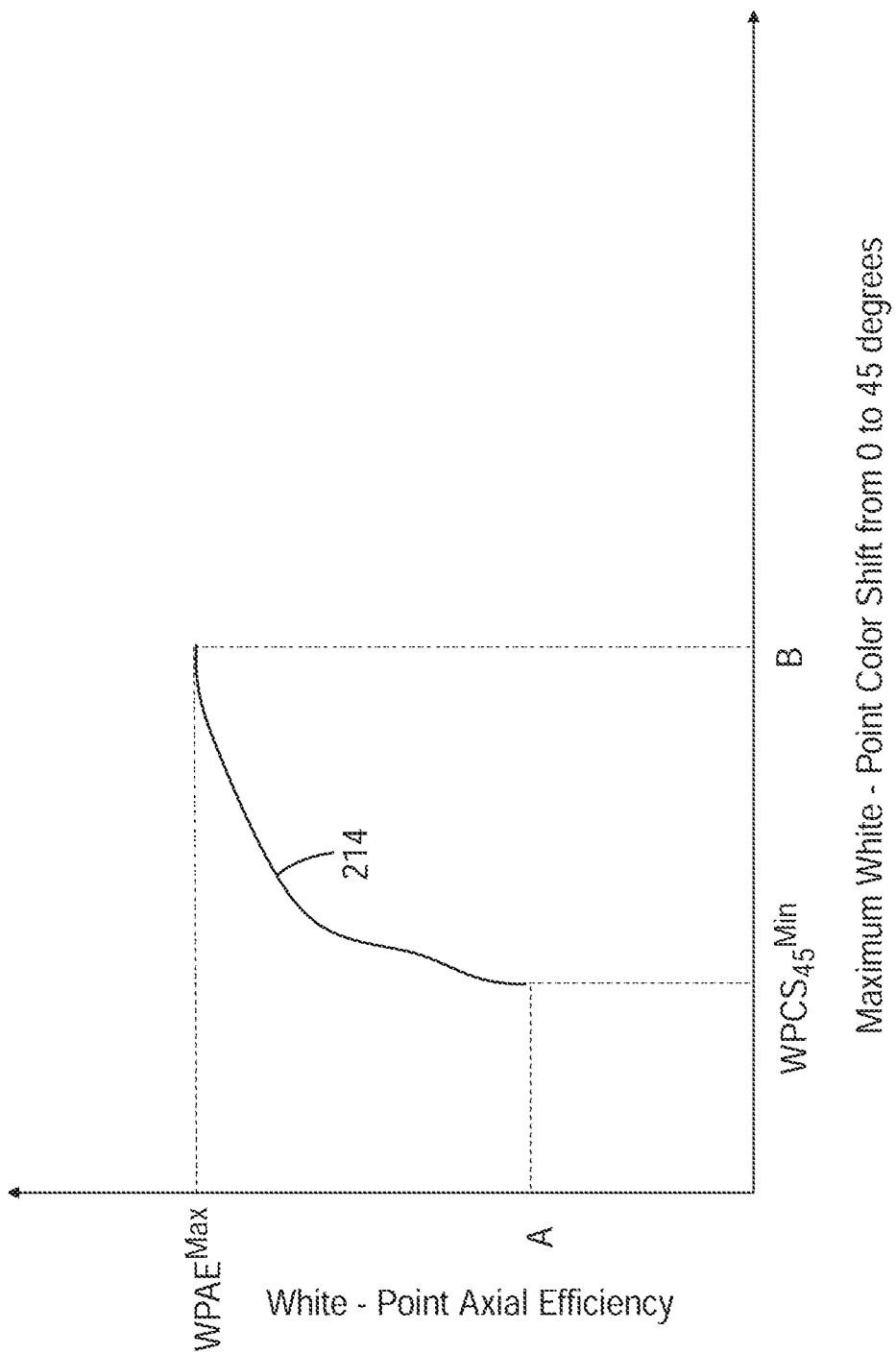
FIG. 3B is a schematic plot of a performance curve defined by the performance space of FIG. 3A.

FIG. 3A schematically illustrates an extended performance space 212 in $WPAE^C$–$WPCS^C_{45}$ coordinates. In the illustrated embodiment, as the efficiency and color-shift drop along the performance curve 214, a minimum of $WPCS^C_{45}$ is reached. This minimum is labeled $WPCS_{45}^{Min}$ and has a corresponding white-point axial efficiency of A. In other embodiments, WPAE approaches $WPCS_{45}^{Min}$ as WPAE approaches zero and there is no change in sign of the slope as illustrated. In this case, A can be taken to be zero. In the illustrated embodiment, as the efficiency and color-shift increase along the performance curve 214, a maximum of WPAE is reached. This maximum is labeled $WPAE^{Max}$ and has a corresponding maximum white-point color shift as a view angle varies from 0 to 45 degrees of B. In other embodiments, WPAE approaches $WPAE^{Max}$ for large $WPCS^C_{45}$ and there is no change in sign of the slope as illustrated. In this case, B can be taken to a largest achievable $WPCS^C_{45}$. The performance curve 214 is the portion of the boundary of the extended performance space 212 extending between the performance points ($WPCS_{45}^{Min}$, A) and (B, $WPAE^{Min}$). FIG. 3B schematically illustrates the performance curve 214 without the remaining portions of the boundary of the performance space 212. In some embodiments, the performance curve 214 may be taken to extend over only a portion of the curve between ($WPCS_{45}^{Min}$, A) and (B, $WPAE^{Min}$). For example, a lower endpoint of the curve may be taken to be a point where the white-point axial efficiency is at a lowest acceptable value, which may be higher than A, and a second endpoint of the curve may be taken to be a point where the maximum white-point color shift as a view angle varies from 0 to 45 degrees is at a largest acceptable value, which may be lower than B.

FIG. 3C illustrates what is meant by to the left or to the right of the performance curve 214. A point is to the right of the performance curve 214 if a horizontal line drawn from the point toward points of lower $WPCS^C_{45}$ intersects the performance curve 214 or intersects a vertical line extending downward from a left endpoint of the performance curve 214 or a vertical line extending upward from a right endpoint of the performance curve 214. Similarly, a point is to the left of the performance curve 214 if a horizontal line drawn from the point toward points of higher $WPCS^C_{45}$ intersects the performance curve 214 or intersects the vertical line extending downward from the left endpoint of the performance curve 214 or the vertical line extending upward from the right endpoint of the performance curve 214.

FIG. 3D illustrates what is meant by above or below the performance curve 214. A point is below of the performance curve 214 if a vertical line drawn from the point toward points of higher $WPAE^C$ intersects the performance curve 214 or intersects a horizontal line extending to the left from a left endpoint of the performance curve 214 or a horizontal line extending to the right from a right endpoint of the performance curve 214. Similarly, a point is above the performance curve 214 if a vertical line drawn from the point toward points of lower $WPAE^C$ intersects the performance curve 214 or intersects the horizontal line extending to the left from the left endpoint of the performance curve 214 or the horizontal line extending to the right from the right endpoint of the performance curve 214.

Placing the color-correction component on a comparative display panel having a performance point defines a modified performance point. The color-correction components and the plurality of comparative display panels having performance points along the performance curve therefore define a plurality of modified performance points. Since the design space may be, and typically is, higher than two dimensional, there may be more than one comparative display panel having a same performance point in the two-dimensional $WPCS^C_{45}$–$WPAE^C$ space. In general, not all of these comparative display panels shift to the same modified performance point. This is schematically illustrated in FIG. 4A. Comparative display panels along a performance curve 214 have a shifted performance in the region 313. In some embodiments, the region 313 appears differently than that illustrated in FIG. 4A. For example, the region 313 is not necessarily a relatively thin region as illustrated. Furthermore, the region 313 may have a significantly different shape than the performance curve 214. In some embodiments, the region 313 includes regions where the white-point color shift is improved for a given white-point axial efficiency and regions where the white-point color shift is worsened for a given white-point axial efficiency.

The modified performance curve 314 is the portion of the boundary of points in the region 313 having the lowest $WPCS^C_{45}$ for a given $WPAE^C$ or having the highest $WPAE^C$ for a given $WPCS^C_{45}$. The modified performance curve 314 can be described as the union of the uppermost and leftmost portions of the boundary of the modified performance points. FIG. 4B is a schematic illustration of the modified performance curve 314 which has a first endpoint 314a, a point 314b of lowest $WPCS^C_{45}$, a point 314c of highest $WPAE^C$, and a second endpoint 314d. In other embodiments, the modified performance curve 314 may appear differently than illustrated in FIG. 4B. For example, first endpoint 314a and point 314b may coincide and/or second endpoint 314d and point 314c may coincide. The uppermost portion of the boundary of the modified performance points is the portion of the modified performance curve 314 between the point 314b and the second endpoint 314d. The leftmost portion of the boundary of the modified performance points is the portion of the modified performance curve 314 between the first endpoint 314a and the point 314c. Since the modified performance curve 314 can include points where the slope changes sign, such as points 314b and 314c, we define points to be above or below the modified performance curve 314 if the points are above or below, respectively, the uppermost portion of the modified performance curve 314 in the sense described above for performance curve 214. Similarly, we define points to be to the left or to the right of the modified performance curve 314 if the points to the left or to the right, respectively, of the left most portion of the modified performance curve 314 in the sense described above for performance curve 214. For example, region 390 is above and to the left of the modified performance curve 314, region 392 is below and to the left of the modified performance curve 314, and region 394 is above and to the right of the modified performance curve 314. In some embodiments, a display of the present description has a performance point above or to the left of the modified performance curve 314 (e.g., in any of the regions 390, 392, or 394). In some embodiments, the display has a performance point above and to the left of the modified performance curve 314 (e.g., in region 390).

An OLED display panel typically includes a plurality of pixels where each pixel includes at least red, green and blue subpixels and each subpixel includes an emissive stack. In conventional approaches, the red, green and blue emissive stacks are designed to minimize the shift of the primary colors and maintain the balance between the color mixing weights so that an acceptably low color shift results (no more than $WPCS_{45}^{LA}$). In the present approach, the emissive stacks are designed according to some embodiments to deliberately create an imbalance in the color mixing weights that will be restored by the color-correction component. For example, in some embodiments, this imbalance can be achieved by strengthening a cavity of the OLED emissive stacks and/or by changing a thickness or optical thickness of the cavity as described further elsewhere herein. The desired imbalance can be determined from the shift in color mixing provided by the color-correction component and can be quantified in term of color mixing weights.

The color mixing weight of color, such as the color produced by a subpixel, refers to the sum of the tristimulus values X, Y, and Z defined by the CIE in 1931 (the CIE 1931 XYZ color space). The tristimulus values are the integrals of the spectral radiance times the corresponding tristimulus response functions (denoted $X(\lambda)$, $Y(\lambda)$, $Z(\lambda)$ or $\bar{x}(\lambda)$, $\bar{y}(\lambda)$, $\bar{z}(\lambda)$). The relative color mixing weight refers to the color mixing weight at a specified view angle divided by the color mixing weight at a zero-view angle. Dividing by the color mixing weight at a zero-view angle provides a convenient normalization so that the relative color mixing weights are unity at zero view angle. The ratio of blue-to-red color mixing weights refers to the relative color mixing weight of blue subpixels divided by the relative color mixing weight of red subpixels. Similarly, the ratio of green-to-red color mixing weights refers to the relative color mixing weight of green subpixels divided by the relative color mixing weight of red subpixels.

For a given color-correction component, the shift in color mixing weights provided by the color-correction component can be determined and this can be used in selecting design parameters (e.g., optical thicknesses) for the emissive stacks such that when the color-correction component is included, the white-point color shift is suitably low. In some embodiments, a color-correction component includes first and second layers and a nanostructured interface therebetween. A nanostructured interface is an interface between two materials that includes nanostructures where nanostructures are structures having a least one length scale in a range of 1 nm to 1000 nm. In some embodiments, the nanostructures have a least one length scale in a range of 10 nm to 500 nm, or in a range of 100 nm to 350 nm. For example, a useful color-correction component, as generally described in PCT Publication No. WO 2017/205174 (Freier et al.), utilizes nanostructures between low and high index layers having a root-mean-square amplitude (also denoted Var) of 125 nm and having a substantially azimuthally symmetric power spectral density (PSD) concentrated in an annulus between wavenumbers 25 $\mu m^{-1}$ and 37 $\mu m^{-1}$. The high index (e.g., n=1.85) layer is typically disposed facing the OLED stack and the low index (e.g., n=1.5) layer is typically disposed facing the viewer. From the PSD of this color-correction component, it can be determined that a display panel having a ratio of blue-to-red color mixing weights $\beta_i$ at a view angle $\theta_i$ and a ratio of green-to-red color mixing weights $\gamma_i$ at $\theta_i$ according to the Table 2 will result in a low white-point color shift when the color-correction component is included.

TABLE 2

| | 0° | 5° | 10° | 15° | 20° | 25° | 30° | 35° | 40° | 45° |
|---|---|---|---|---|---|---|---|---|---|---|
| $\beta_i$ | 1.000 | 1.003 | 1.039 | 1.069 | 1.102 | 1.141 | 1.175 | 1.211 | 1.229 | 1.271 |
| $\gamma_i$ | 1.000 | 1.000 | 1.000 | 1.000 | 1.000 | 1.000 | 1.000 | 1.018 | 1.044 | 1.055 |

In some embodiments, values of a plurality of design parameters (e.g., optical thicknesses of various layers in the OLED emissive stacks) for the OLED display panel are selected to deliberately create an imbalance in color mixing weights of the OLED display panel at one or more oblique viewing angles. In some embodiments, this imbalance is selected based on a characterization of a color correction provided by the color-correction component. For example, the imbalance in color mixing weights may be selected to match or approximate the color mixing weight ratios of Table 2 when the color-correction component is as described above. For other color-correction components, the color mixing weight ratios may differ substantially from that shown in Table 2. However, some general trends exhibited in Table 2 hold for a variety of color-correction components. For example, it is typically preferred that the ratio of blue-to-red color mixing weight be larger than ratio of green-to-red color mixing weight throughout the angular view range of 20 degrees to 45 degrees. In some embodiments, the ratio of blue-to-red color mixing weight is constant or monotonically increasing with view angle from zero to 45 degrees. In some embodiments, the ratio of green-to-red color mixing weight is close to unity (e.g., between 0.99 and 1.01) for view angles between zero and 20 degrees (or 25 degrees or 30 degrees) and is constant or monotonically increasing with view angle from 20 degrees (or 25 degrees or 30 degrees) to 45 degrees.

In some embodiments, an OLED display includes a pixelated OLED display panel and a color-correction component disposed on the pixelated OLED display panel. In some embodiments, the display panel has a ratio of blue-to-red color mixing weights at 30 degrees of $\beta^o_{30}$, and a ratio of blue-to-red color mixing weights at 45 degrees of $\beta^o_{45}$, where $\beta^o_{45} > \beta^o_{30} \geq 1.05$ and $1.5 \geq \beta^o_{45} \geq 1.1$. In some embodiments, the color-correction is configured such that a ratio of blue-to-red color mixing weights at 45 degrees of the display is $\beta_{45}$ and a ratio of blue-to-red color mixing weights at 30 degrees of the display is $\beta_{30}$. In some embodiments, $\beta_{45}$ is closer to unity than is $\beta^o_{45}$ and $\beta_{30}$ is closer to unity than is $\beta^o_{30}$. In some embodiments, $\beta_{45}$ is no more than $\beta^o_{45}-0.15$ or no more than $\beta^o_{45}-0.1$. In some embodiments, $\beta_{30}$ is no more than $\beta^o_{30}-0.1$ or no more than $\beta^o_{30}-0.05$. In some embodiments, $\beta^o_{45}-0.1 \geq \beta_{45} \geq 2.1-\beta^o_{45}$ and $\beta^o_{30}-0.05 \geq \beta_{30} \geq 2.05-\beta^o_{30}$. In some embodiments, $\beta^o_{45}$ is no more than 1.4. In some embodiments, $\beta^o_{45}$ is at least 1.19. In some embodiments, $1.38 \geq \beta^o_{45} \geq 1.15$ or $1.35 \geq \beta^o_{45} \geq 1.19$ or $1.33 \geq \beta^o_{45} \geq 1.21$. In some embodiments, $1.4 \geq \beta^o_{30}$. In some embodiments, $1.25 \geq \beta^o_{30} \geq 1.07$. In some embodiments, $\beta^o_{45}-\beta^o_{30} \geq 0.03$ or $\beta^o_{45}-\beta^o_{30} \geq 0.04$ or $\beta^o_{45}-\beta^o_{30} \geq 0.05$ or $\beta^o_{45}-\beta^o_{30} \geq 0.06$. In some embodiments, $\beta^o_{45}-\beta^o_{30}$ is no more than 0.3, or 0.25, or 0.2, or 0.15. In some embodiments, $1.26 \geq \beta^o_{30} \geq 1.1$ and $1.35 \geq \beta^o_{45} \geq 1.19$. It is preferable that $\beta_{30}$ and $\beta_{45}$ be close to unity. In some embodiments, $1.1 \geq \beta_{45} \geq 0.9$, or $1.08 \geq \beta_{45} \geq 0.92$, or $1.06 \geq \beta_{45} \geq 0.94$, or $1.05 \geq \beta_{45} \geq 0.95$, or $1.04 \geq \beta_{45} \geq 0.96$. In some embodiments, $1.1 \geq \beta_{30} \geq 0.9$, or $1.08 \geq \beta_{30} \geq 0.92$, or $1.06 \geq \beta_{30} \geq 0.94$, or $1.05 \geq \beta_{30} \geq 0.95$, or $1.04 \geq \beta_{30} \geq 0.96$.

In some embodiments, the pixelated OLED display panel has a ratio of green-to-red color mixing weights at 45 degrees of $\gamma^o_{45}$ and the OLED display (including the color-correction component) has a ratio of green-to-red color mixing weights at 45 degrees of the display of $\gamma_{45}$. In some embodiments, $\gamma^o_{45}$ is at least 1.025 or at least 1.03, $\gamma_{45}$ is no more than $\gamma^o_{45}-0.005$ and $1.025 \geq \gamma_{45} \geq 0.975$. In some embodiments, $1.1 \geq \gamma^o_{45} \geq 1.03$, or $1.08 \geq \gamma^o_{45} \geq 1.03$, $1.07 \geq \gamma^o_{45} \geq 1.04$. In some embodiments, $\gamma_{45}$ is no more than $\gamma^o_{45}-0.01$, or no more than $\gamma^o_{45}-0.02$, or no more than $\gamma^o_{45}-0.03$. In some embodiments, $1.02 \geq \gamma_{45} \geq 0.98$, or $1.015 \geq \gamma_{45} \geq 0.985$, or $1.01 \geq \gamma_{45} \geq 0.99$.

In some embodiments, the pixelated OLED display panel has a ratio of green-to-red color mixing weights at 30 degrees of $\gamma^o_{30}$ and the OLED display has a ratio of green-to-red color mixing weights at 30 degrees of $\gamma_{30}$. In some embodiments, $\gamma_{30}$ is at least as close to unity as is $\gamma^o_{30}$. In other embodiments, $\gamma_{30}$ and $\gamma^o_{30}$ are each close to unity (e.g., both in a range of 0.98 to 1.02 or 0.99 to 1.01) and $\gamma_{30}$ may not be as close to unity as is $\gamma^o_{30}$. In some embodiments, $1.03 \geq \gamma^o_{30} \geq 0.97$, or $1.02 \geq \gamma^o_{30} \geq 0.98$, or $1.01 \geq \gamma^o_{30} \geq 0.99$. In some embodiments, $1.03 \geq \gamma_{30} \geq 0.97$, or $1.02 \geq \gamma_{30} \geq 0.98$, or $1.01 \geq \gamma_{30} \geq 0.99$. In some embodiments, $1.03 \geq \gamma^o_{30}$ 0.97 and $1.02 \geq \gamma^o_{30}$ 0.98. In some embodiments, $1.02 \geq \gamma^o_{30} \geq 0.98$ and $1.01 \geq \gamma^o_{30}$ 0.99. In some embodiments, $|\gamma^o_{30}-1| > |\gamma_{30}-1|$.

In some embodiments, a method of making an OLED display includes providing an OLED display panel having a performance point below and to the right of a performance curve in $WPCS^C_{45}$-$WPAE^C$ space and disposing a color-correction component on the OLED display panel configured such that a performance point of the display being above or to the left of a modified performance curve, as described further elsewhere herein. In some embodiments, the method includes determining a largest acceptable maximum white-point color shift from 0 to 45 degrees of the OLED display, $WPCS_{45}^{LA}$, and the providing the display panel step includes selecting the plurality of design parameters such that $WPCS^o_{45}$ is greater than $WPCS_{45}^{LA}$. In some embodiments, the method includes identifying a plurality of design parameters and choosing values for those parameters to deliberately create an imbalance in color mixing weights of the OLED display panel at one or more oblique viewing angles so that $WPCS^o_{45}$ is greater than $WPCS_{45}^{LA}$. In some embodiments, $WPCS_{45}^{LA}$ is determined based on a product performance requirement which may be determined, at least in part, by marketing data, for example. $WPCS_{45}^{LA}$ may differ for cell phones, tablets, computer monitors and television sets and may differ for premium (e.g., high-end cell phone) and budget (e.g., inexpensive cell phone) products. In some embodiments, $WPCS^o_{45}-WPCS_{45}^{LA} \geq 0.005$, or $WPCS^o_{45}-WPCS_{45}^{LA} \geq 0.01$, or $WPCS^o_{45}-WPCS_{45}^{LA} \geq 0.015$. In some embodiments, $WPCS_{45}^{LA}-WPCS_{45} \geq 0.005$, or $WPCS_{45}^{LA}-WPCS_{45} \geq 0.01$, $WPCS_{45}^{LA}-WPCS_{45} \geq 0.015$, or $WPCS_{45}^{LA}-WPCS_{45} \geq 0.02$. In some embodiments, $WPCS_{45}^{LA}$ is at least 0.005, or at least 0.01, or at least 0.015. In some embodiments, $WPCS_{45}^{LA}$ is no more than 0.05, or no more than 0.03, or no more than 0.025, or no more than 0.02, or no more than 0.015, or no more than 0.015, or no more than 0.01.

Figure 5:
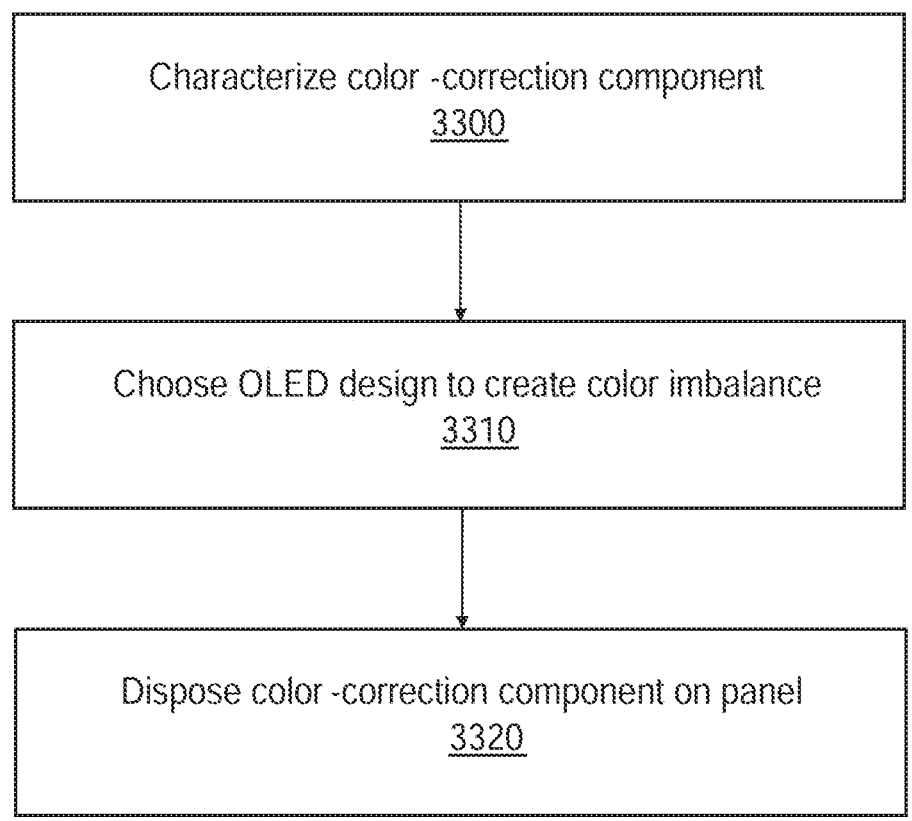
FIG. 5 is a flow diagram outlining a method of making an organic light emitting diode (OLED) display.

FIG. 5 is a flow diagram outlining a method of making an OLED display according to some embodiments of the present description. In step 3300, a color correction provided by a color-correction component is determined. For a given color-correction component (e.g., optical stack including a suitable diffractive nanostructured interface, partial reflector suitable reflectivity and transmittivity, moderate diffuser with suitable optical properties), the degree mixing of different colors provided by the color-correction component as a function of view angle can be determined experimentally or through optical modeling, for example. This results in the shift in color mixing weights provided by the color-correction component. From this, the color imbalance (which can be quantified in terms of the shift in color mixing weights) of the output of a display panel which, when combined with color-correction component, results in a desired or acceptable (e.g., small) white-point color shift with view angle can be determined (see, e.g., Table 2).

In step 3310, an OLED design is chosen to create a color imbalance. In some embodiments, this step includes identifying design parameters (e.g., optical thickness of various layers in the emissive stacks) and choosing values of those parameters to create or approximate the desired color imbalance identified in step 3300. The appropriate values of the design parameters can be chosen by numerically determining the ratio of blue-to-red color mixing weight and the ratio of green-to-red color mixing weight as a function of view angle for various values of the design parameters and then choosing the values to give or approximate the desired ratios. For example, a root-mean-square (rms) error from the desired ratios can be calculated and values of the design parameters which minimize the rms error can be selected. In some embodiments, other considerations or constraints are imposed. For example, the design space may be limited to designs having a color shift for one or more colors to be below specified value(s) and/or having an axial efficiency (WPAE and/or BAE) above specified value(s).

In some embodiments, steps 3320 and 3310 are iterated. For example, step 3310 may be performed for several types of color-correction components and step 3320 may be performed for each of the color-corrections components. Then based on the results of step 3320, addition color-correction components may be considered (e.g., an interpolation or extrapolation of parameters characterizing the tested color-correction components) and step 3320 repeated.

Once the proper values of the design parameters have been identified, an OLED display panel can be made using conventional OLED fabrication processes which may include depositing organic layers by one or more of vacuum deposition, vacuum thermal evaporation, organic vapor phase deposition, and inkjet printing. Useful methods of manufacturing OLED display panels are described in U.S. Pat. Appl. Publ. Nos. 2010/0055810 (Sung et al.), 2007/0236134 (Ho et al.), 2005/0179373 (Kim), and 2010/0193790 (Yeo et al.). In step 3320, the color-correction component is disposed on the display panel.

The design parameters for the OLED display panel may include the thicknesses of the various layers of the emissive OLED emissive stacks and the material choice for the various layers. In some embodiments, the optical thicknesses of various layers are used as the design parameters. The optical thickness of a layer is the physical thickness of the layer times the refractive index of the layer. In the context of a layer in an emissive stack, the refractive index used in determining the optical thickness will be taken to be the refractive index at the peak emission wavelength of the emissive stack. A complex refractive index can be defined for a layer where the imaginary part of the refractive index characterizes the absorption of the layer. Unless indicated differently, the term "refractive index" when no reference is made to a "complex refractive index" refers to a real quantity which can be taken to be the real part of a corresponding complex refractive index.

The design parameters for the OLED display panel can include any layer thickness or layer optical thickness or layer material of any one of the emissive stacks (e.g., blue subpixels), or of any combination of emissive stacks (e.g., blue and green subpixels), or for all emissive stacks. For example, a thickness or optical thickness of a cathode layer, a thickness or optical thickness of a hole transport layer, a thickness or optical thickness of a capping layer, and/or a thickness or optical thickness of an emissive layer of one or more of the emissive stacks are useful design parameters in some embodiments. In some embodiments, the thicknesses of the hole transport layer and emissive layers for the different colored subpixels are considered to be separate design parameters but each of the thicknesses of the other layers of the OLED emissive stacks is taken to be a design parameter common to each of the emissive stacks since common layers are used for the emissive stacks is many conventional manufacturing processes due to manufacturing cost constraints.

Figure 6:
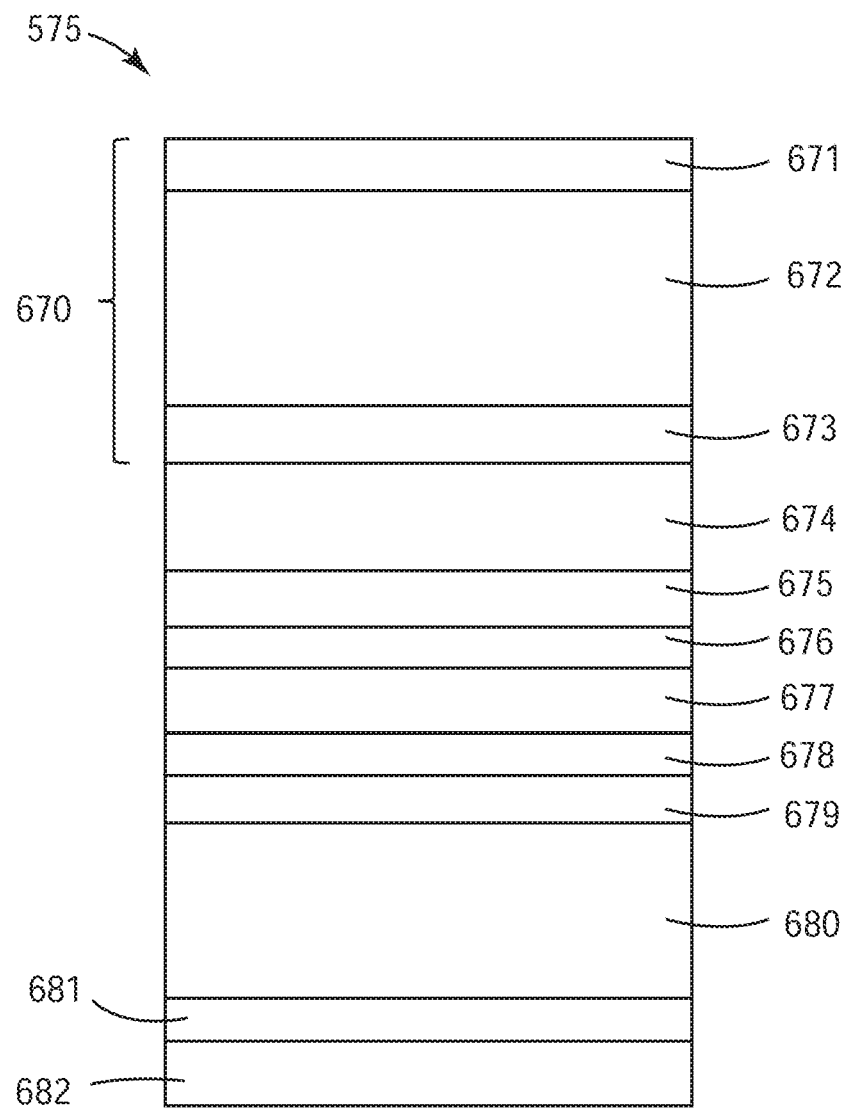
FIG. 6 is a schematic cross-sectional view of an OLED emissive stack.

FIG. 6 is a schematic cross-sectional view of OLED emissive stack 575. The OLED emissive stack 575 includes, in sequence from the top (light emitting side), encapsulant layers 670, optional buffer layer 674, capping layer 675, cathode 676, electron transport layer 677, emissive layer 678, electron blocking layer 679, hole transport layer 680, hole injection layer 681, and anode 682. The encapsulant layers 670, which may be referred to as a thin film encapsulant (TFE), include an organic layer 672 disposed between first and second inorganic layers 671 and 673. The organic layer 672 may have a thickness on the order of micrometers (e.g., about 6 micrometers) and the first and second inorganic layers 671 and 673 may be $Al_2O_3$ layers or silicon nitride layers or other inorganic materials known in the art, for example, having a thickness of about 100 nm or about 50 nm, for example. The optional buffer layer 674 may be a LiF layer and may have a thickness in the range of 80-500 nm, for example. The capping layer 675 may be a TCTA (Tris(4-carbazoyl-9-ylphenyl)amine) layer and may have a thickness in the range of 30-85 nm, for example. The cathode 676 may be a magnesium-silver alloy (e.g., having an Mg:Ag atomic ratio of 9:1) and may have a thickness in a range of 6-16 nm, for example. The electron transport layer 677 may be a Bphen (4,7-diphenyl-1,10-phenanthroline) layer and may have a thickness in the range of 30-65 nm, for example. The emissive layer 678 may include TPBi (2,2', 2"-(1,3,5-Benzinetriyl)-tris(1-phenyl-1-H-benzimidazole) available from Sigma-Aldrich (St. Louis, MO) with a dopant (e.g., at 10 wt. %) and may have a thickness in a range of 15-35 nm, for example. Suitable dopants include Firpic (Bis[2-(4,6-difluorophenyl)pyridinato-C2,N](picolinato) iridium(III)) (blue), Irppy3 (Tris[2-phenylpyridinato-C2,N] iridium(III))(green), and PQIr ((2,4-Pentanedionato)bis[2-(2-quinolinyl)phenyl]iridium(III)) (red). The electron blocking layer 679 may be a 2TNATA (4,4',4"-Tris[2-naphthyl(phenyl)amino]triphenylamine) (available from Sigma-Aldrich) layer and may have a thickness in the range of 8-12 nm, for example. The hole transport layer 680 may be a TCTA (Tris(4-carbazoyl-9-ylphenyl)amine) (available from Sigma-Aldrich) layer and may have a thickness in the range of 90 nm to 230 nm, for example, with thinner layers used for blue subpixels, thicker layers used for red subpixels and intermediate thicknesses used for green subpixels. The hole injection layer 681 may be an indium tin oxide (ITO) layer and may have a thickness in the range of 5-18 nm, for example. The anode 682 may be an aluminum layer and may have a thickness of 100 nm, for example.

Figure 7:
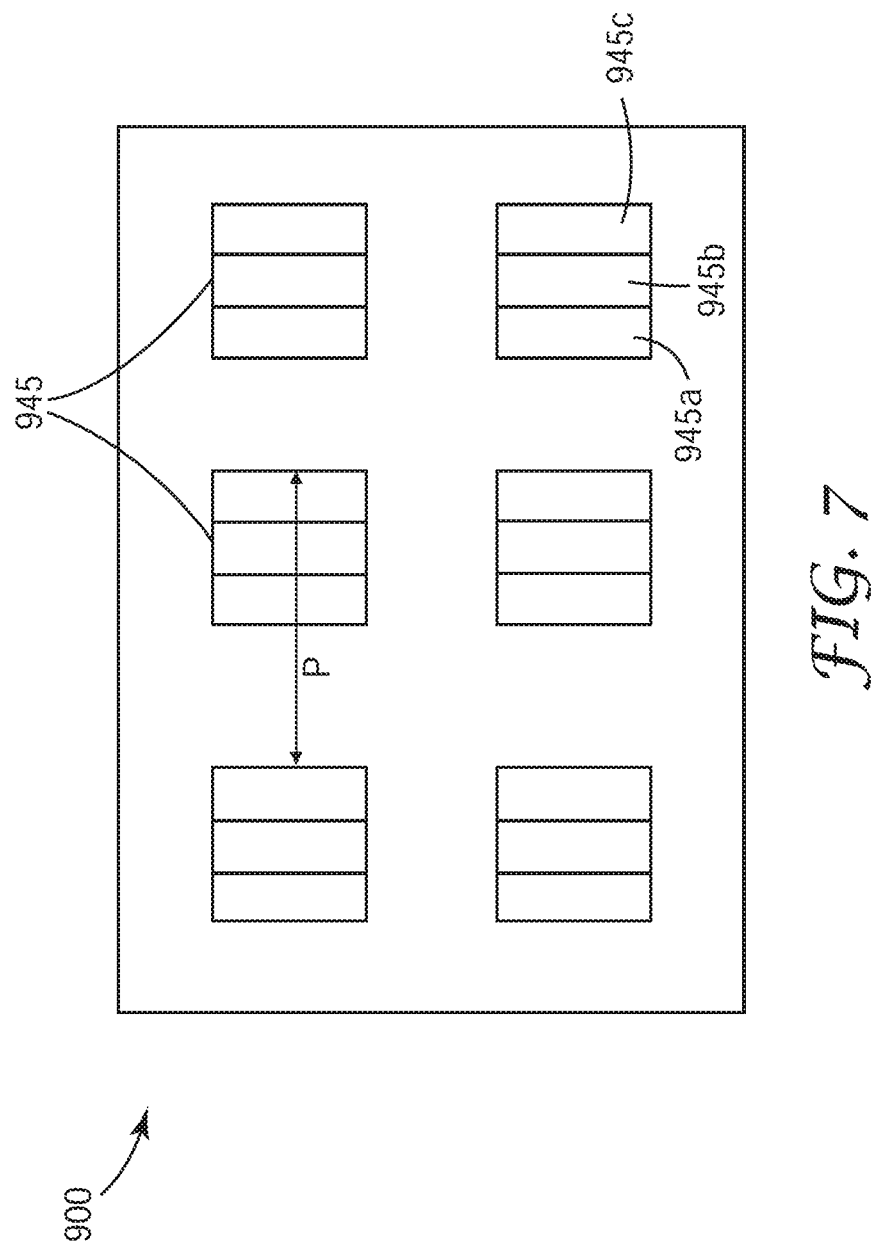
FIG. 7 is a schematic top view of an OLED display panel.

FIG. 7 is a schematic top view of an OLED display panel 900 which includes a plurality of pixels 945, where each pixel includes subpixels 945a, 945b and 945c. Subpixels 945a, 945b, and 945c are typically different colors such as red, green and blue. An average pixel spacing P is illustrated. The spacing P is the pitch between nearest neighbor pixels. Display panel 900 may be a display panel of the present description or may be a comparative display panel depending on the layers used for the subpixels 945a, 945b, and 945c. Additional subpixels (e.g., yellow) may be included in some embodiments. The pixel and subpixel arrangement can be similar to or different from that schematically illustrated in FIG. 7. For example, a triangular pattern, striped pattern, diagonal pattern, or a PENTILE matrix can be used as is known in the art. In the case of a PENTILE matrix which includes red and green pairs of subpixels and green and blue pairs of subpixels, for example, each pixel can be understood to include a red and green pair and a green and blue pair, so that each pixel includes four subpixels.

Figure 8:
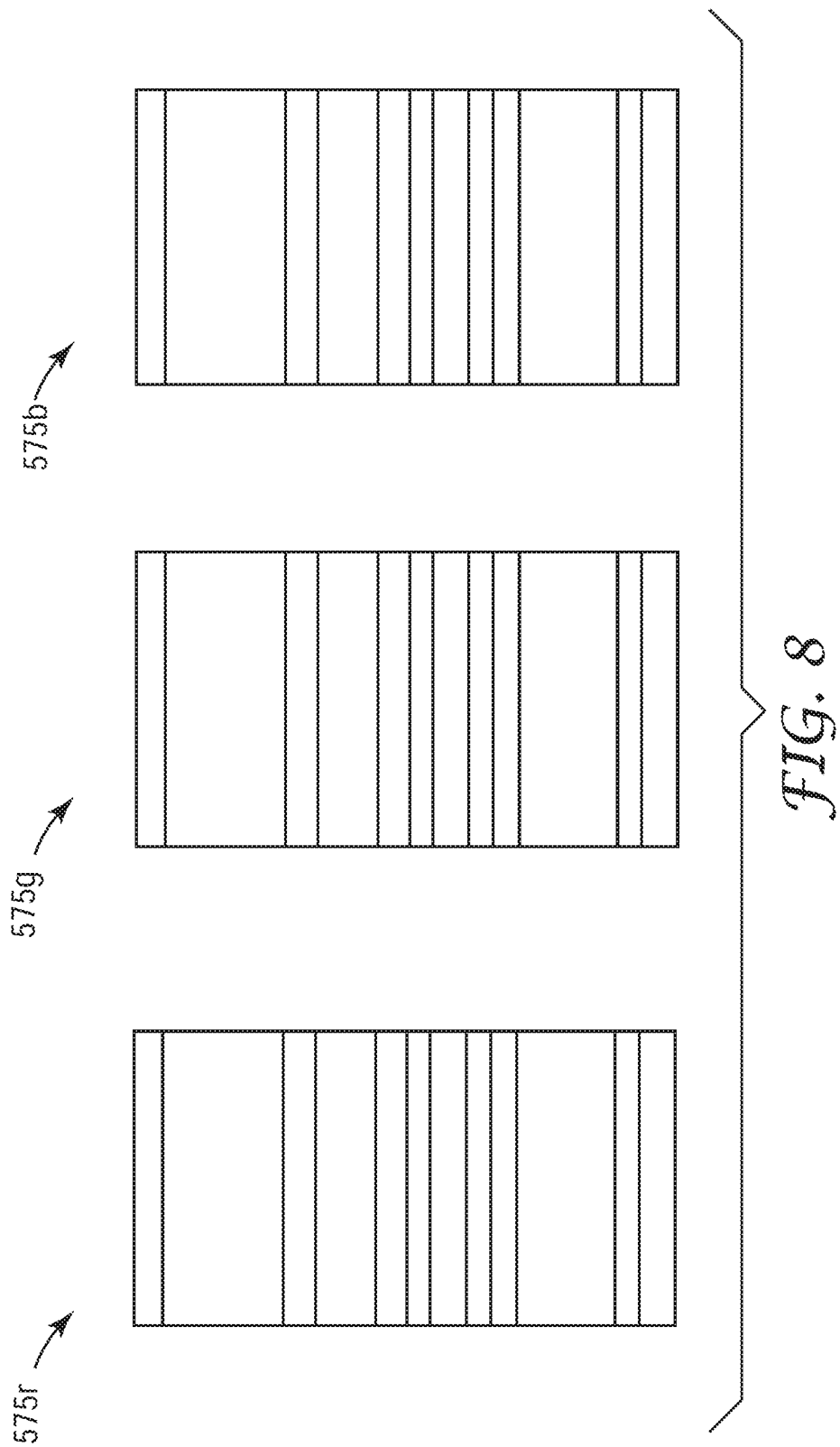
FIG. 8 is a schematic cross-sectional view of red, green and blue OLED emissive stacks.

FIG. 8 is a schematic cross-sectional view of a red OLED emissive stack 575r, a green OLED emissive stack 575g, and a blue OLED emissive stack 575b. Each emissive stack 575r, 575g, and 575b correspond to the emissive stack 575 and have the same types of layers described for the emissive stack 575. The materials used in one or more layers of one emissive stack may be different from those used in another emissive stack. For example, the emissive layer 678 used in different colored emissive stacks typically have differing compositions to provide the different colors. The layer thicknesses of one or more layers of one emissive stack may be different from those of another emissive stack. The emissive stacks 575r, 575g, and 575b may also correspond to subpixels 945a, 945b, and 945c.

In some embodiments, the OLED stacks used in the display panels of the present description use thicker and/or stronger cavities than comparative display panels. Using a thicker cavity shifts the peaks of cavity emissivity away from the sharp edge of the dopant emission spectrum. This results in increased shifts to shorter wavelengths in the device emission, resulting in a larger initial shift in the color toward shorter wavelengths. Strengthening the cavity narrows the peaks and increases the sensitivity of color to the peak wavelength. The net result, in some embodiments, is more than a factor of two increase in the maximum color shift between 0 and 45 degrees for the display panels of the present description relative to the comparative display panels. Without the color-correction component, such a large color shift would be unacceptable for many applications. However, the color-correction component can at least partially correct the color shift to provide an acceptable color shift. The axial efficiency is increased both by moving the axial peak away from the edge of the dopant emission and the increased peak amplitude of the stronger cavity emissivity. This results in an improved axial efficiency for a display that includes the color-correction component and that has a same color shift as a comparative display panel, according to some embodiments.

A simple model that is useful for understanding the emissivity of an emissive stack such as OLED emissive stack 575 is a Fabry-Perot optical cavity model where encapsulant layers 670 are disposed on a cavity having top side defined by buffer layer 674, capping layer 675, and cathode 676 and having a bottom side defined by anode 683. The electron transport layer 677, emissive layer 678, electron blocking layer 679, hole transport layer 680, and hole injection layer are considered to be layers in the interior of the cavity. The cavity emissivity is a maximum when 2 $n_{cav}$ $T_{cav}$ $\cos(\theta_{cav})$ is an integer times the wavelength of the light emitted into air, where $n_{cav}$ is an effective refractive index of the interior layers of the cavity, $T_{cav}$ is the thickness of the cavity, and $\theta_{cav}$ is the emission angle relative to normal in the cavity which is related to the view angle in air exterior to the emissive stack by Snell's law. The emission of the emissive stack is the cavity emissivity times the dopant emission. In the cavity model, the color shift results primarily from the $\cos(\theta_{cav})$ term in the cavity emissivity.

Figure 9:
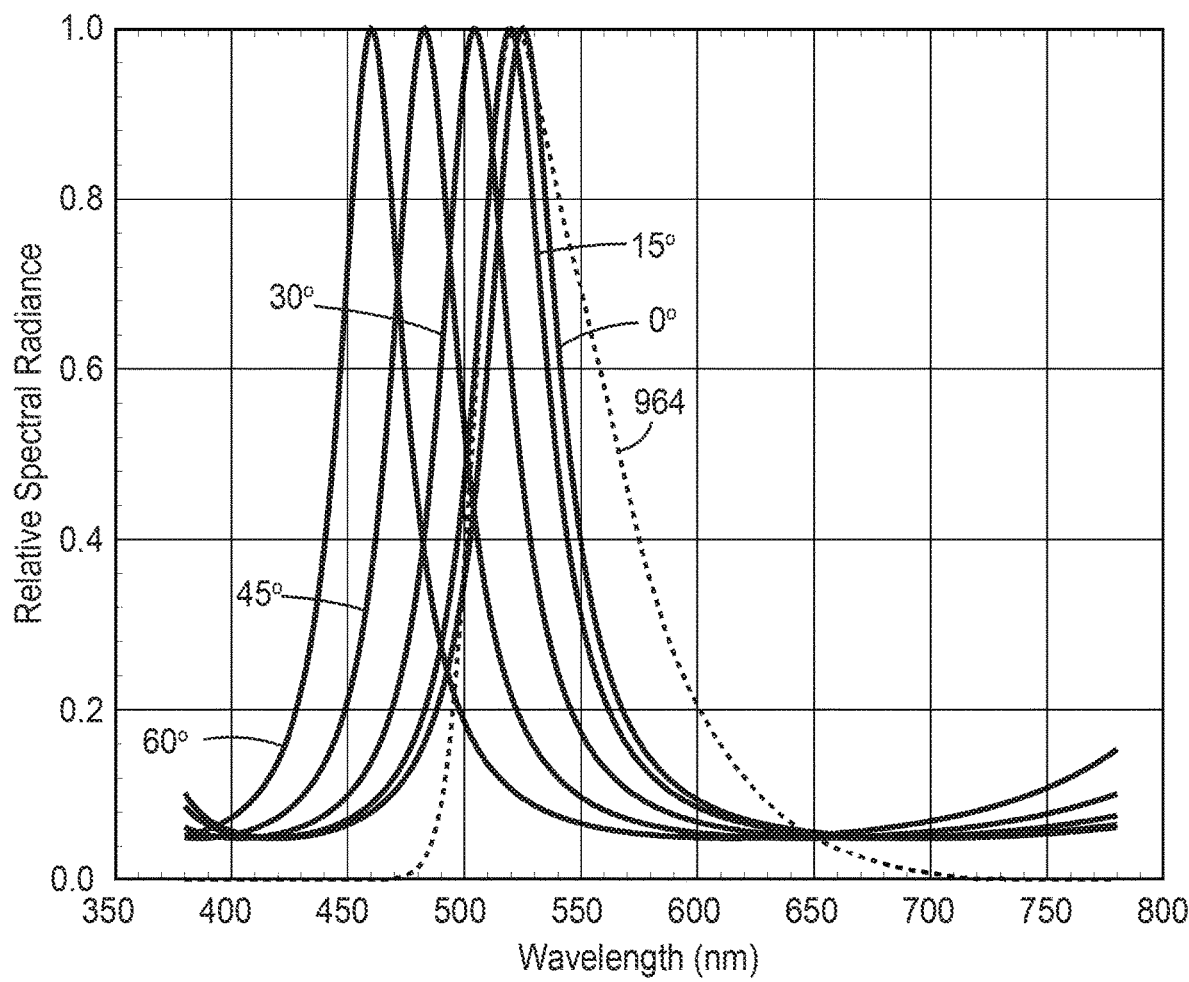
FIG. 9 is a plot of the cavity emissivity and dopant emission of a green subpixel of a comparative display panel.
Figure 10:
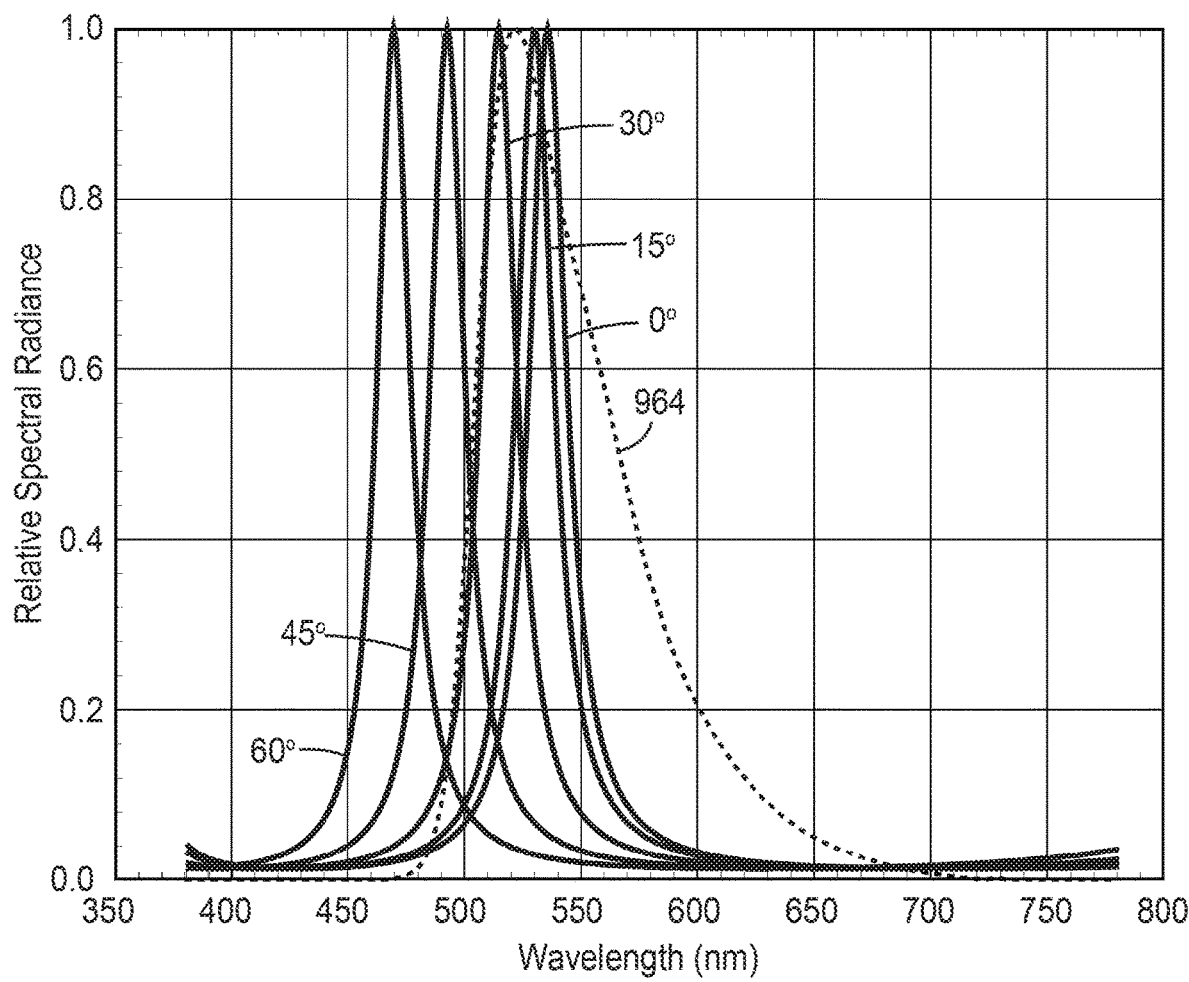
FIG. 10 is a plot of the cavity emissivity and dopant emission of a green subpixel of a display panel according to some embodiments.
Figure 11:
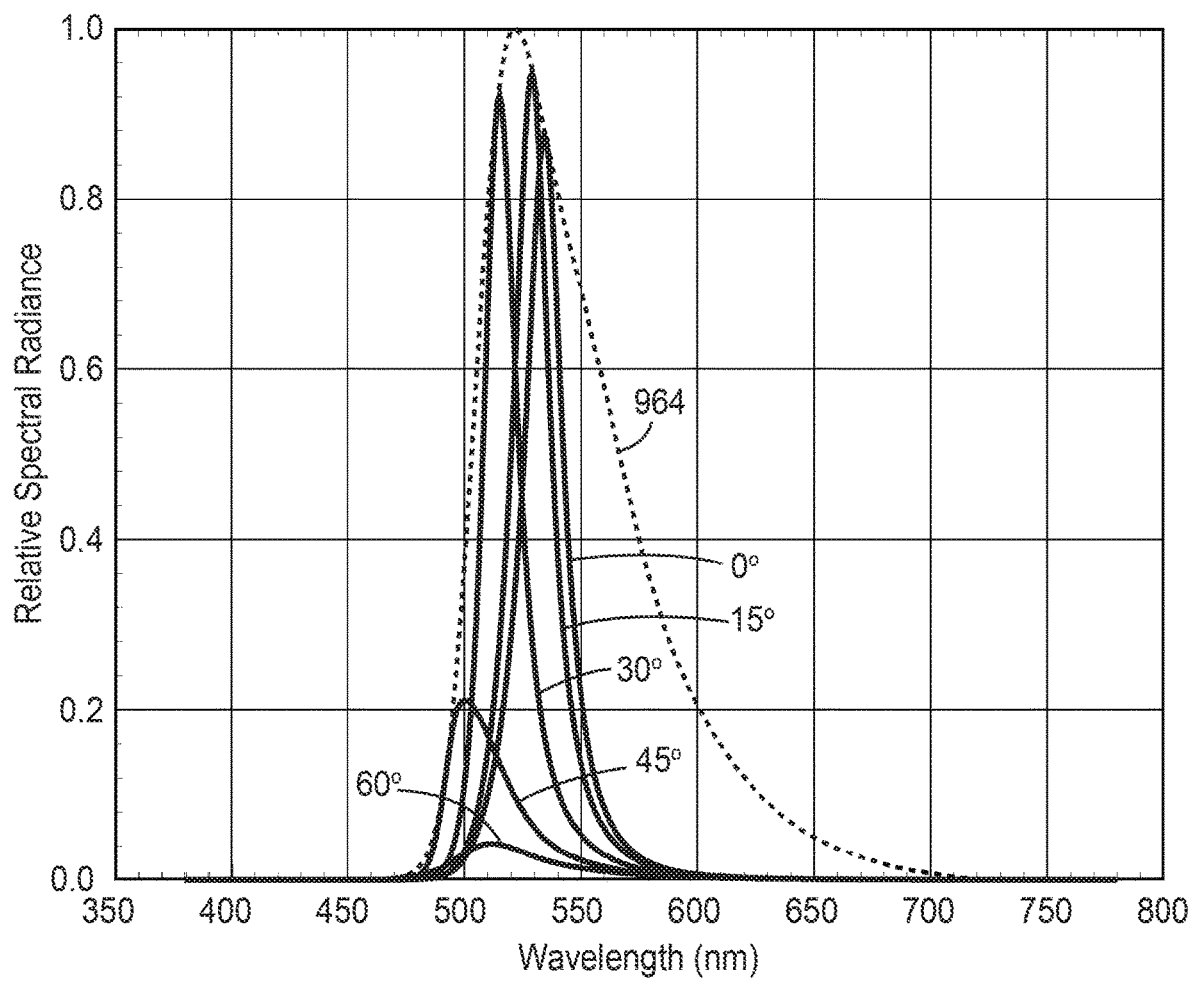
FIG. 11 is a plot of the relative spectral emission of the green subpixel of FIG. 10.

FIGS. 9-10 are plots of the cavity emissivity and dopant emission of a green subpixel of a comparative display panel and of a green subpixel of a display panel of the present description, respectively, resulting from the Fabry-Perot optical cavity model. Cavity emissivity at zero, 15, 30, 45 and 60 degrees and dopant emission are illustrated. The device emission is the product of the cavity emissivity and the dopant emission. FIG. 11 shows the relative spectral emission of the green subpixel of FIG. 10. In FIG. 9, the axial peak at zero-degree view angle is close to the edge 964 of the dopant emission and in FIG. 10 the axial peak at zero-degree view angle is farther away from the edge 964 of the dopant emission. As described elsewhere herein, this shift can be obtained by using a thicker cavity. In FIG. 10 the widths of the cavity emissivity peaks are narrowed compared to FIG. 9. As described elsewhere herein, this narrowing can be obtained by using a stronger cavity.

Figure 12:
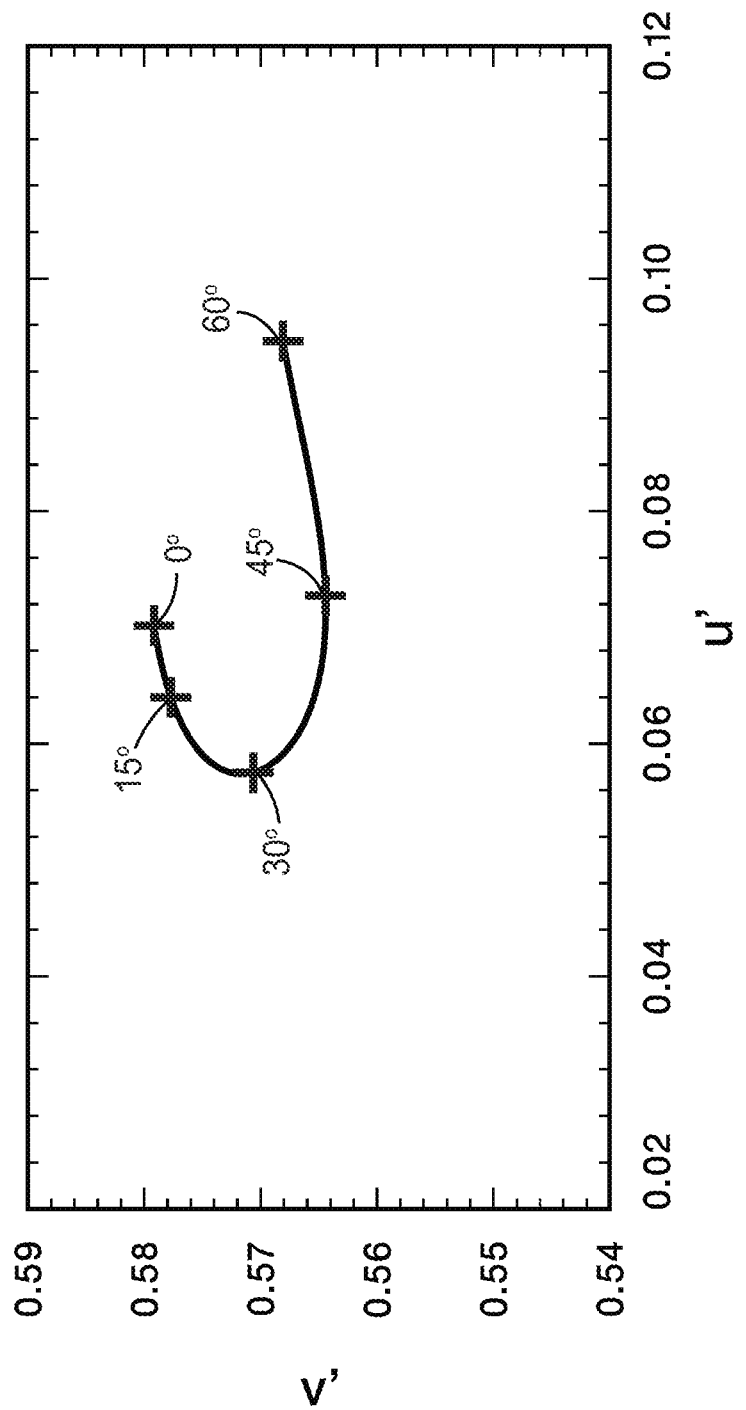
FIG. 12 is a u'-v' plot of the color shift with view angle of the green subpixel of FIG. 9.
Figure 13:
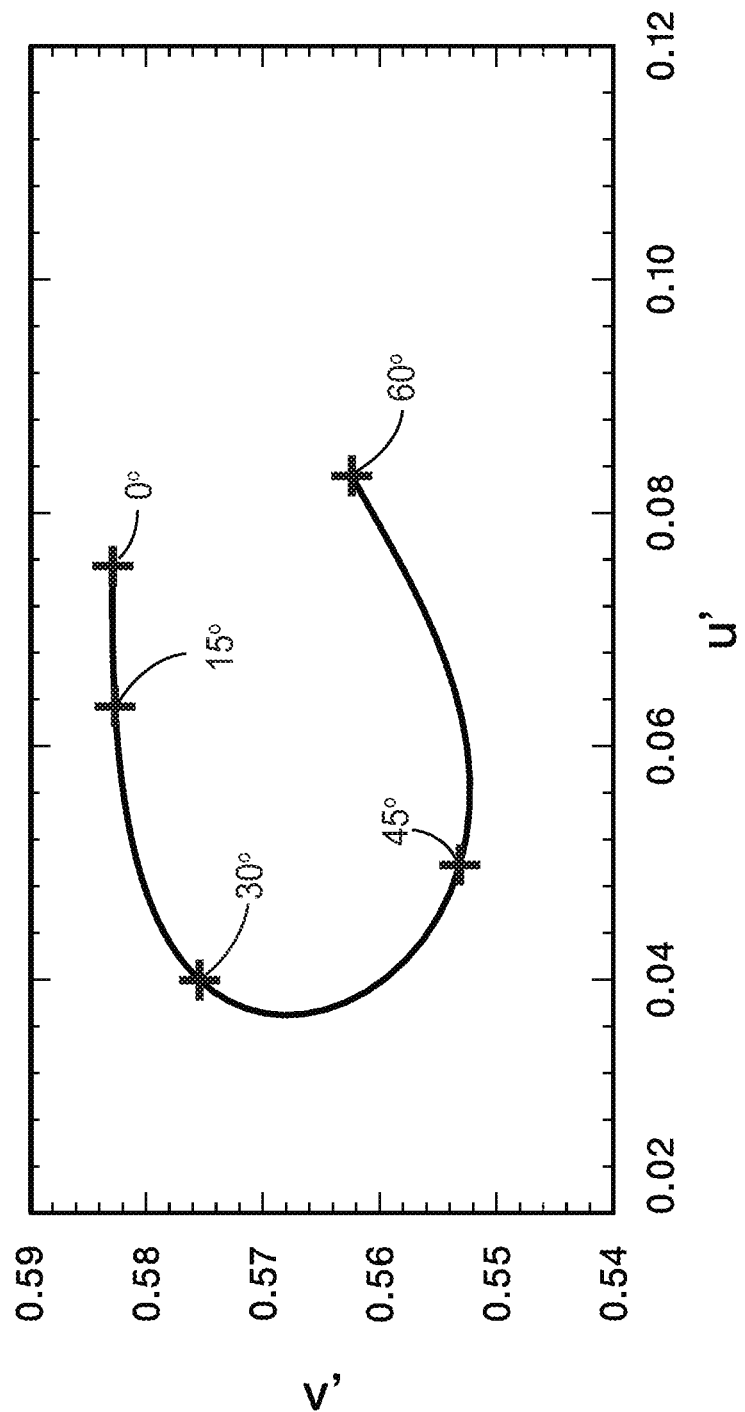
FIG. 13 is a u'-v' plot of the color shift with view angle of the green subpixel of FIG. 10.

FIGS. 12-13 show the color-shift with view angle of the green subpixels illustrated in FIGS. 9-10, respectively. The maximum color shift from zero to 45 degrees illustrated in FIG. 13 is substantially greater than that illustrated in FIG. 12. However, when a color-correction component is included the color-shift of FIG. 13 is reduced and may be less than that of FIG. 12 and/or may result in a display having an acceptable color-shift and an improved efficiency, for example.

The thickness of the cavity can be adjusted by adjusting the thickness of the hole transport layer and/or the emissive layer, for example. In some embodiments, the color-correction component has a substantially stronger effect on blue wavelengths than on green wavelengths and a substantially weaker effect on red wavelengths than on green wavelengths. It has been found that the thickness hole transport layer of the blue emissive stack in particular is a useful design parameter for adjusting the color shift of the emissive stack to effectively utilize the color-correction component. Since the refractive index times the cavity thickness enters the cavity emissivity model, when different materials are considered for the hole transport layer, a useful design parameter is the optical thickness of the hole transport layer of the blue emissive stacks.

Figure 14:
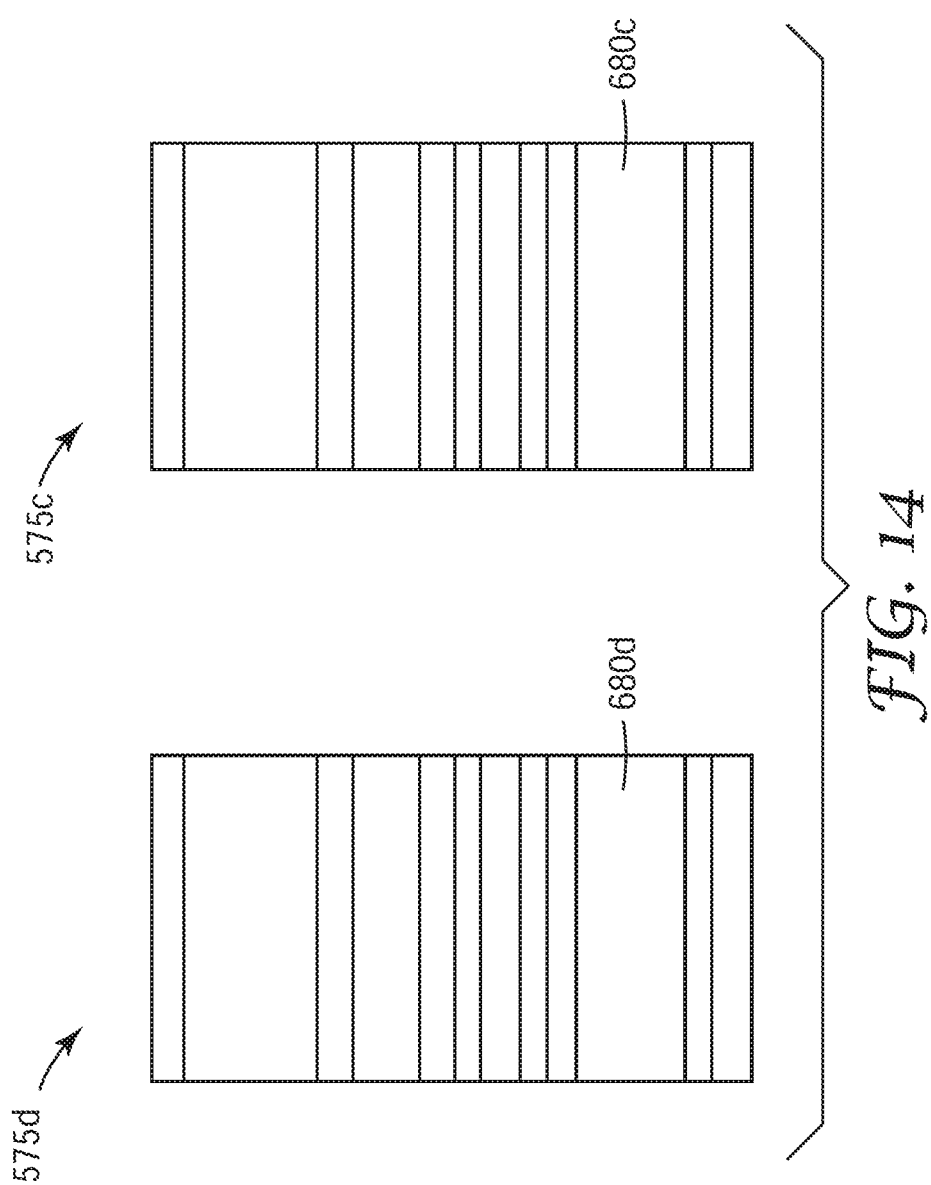
FIG. 14 is a schematic cross-sectional view of a subpixel of a display panel according to some embodiments and a subpixel of a comparative display panel.

FIG. 14 is a schematic cross-sectional view of a subpixel 575d of a display panel of the present description and a subpixel 575c of a comparative display panel. The subpixel 575d may correspond to any of the OLED emissive stacks 575r, 575g, and 575b, for example. The subpixel 575c differs from the subpixel 575d by one or more design parameters which may include a material of the layers of the subpixel, a thickness of the layers of the subpixel, and/or an optical thickness of the layers of the subpixel. In the illustrated embodiment, the subpixel 575d has a hole transport layer 680d that is thicker than the hole transport layer 680c of the subpixel 575c of the comparative display panel. In some embodiments, a thickness of the hole transport layer 680d of a blue subpixel is at least 1.02 times, or at least 1.03 times a thickness of a hole transport layer 680c of a corresponding blue subpixel in a comparative display panel. In some embodiments, the thickness of the hole transport layer 680*d* of the blue subpixel is no more than 1.1 times the thickness of the hole transport layer 680*c* of the corresponding blue subpixel in the comparative display panel.

The strength of the cavity can be adjusted by adjusting the reflectivity of the cathode (e.g. cathode 676). This could be done by changing the thickness of the cathode. However, it is typically desired that the cathode has a sufficient thickness to drain the required drive current without substantial voltage drop and this limits the degree that the cathode thickness can be varied to control reflectivity of the cathode. Another approach is to use a relatively thick and reflective cathode and to optimize the buffer and capping layer (e.g., buffer layer 674 and capping layer 675) thicknesses and refractive indices to exploit interference of reflected waves to diminish the reflectivity of the cathode. In some embodiments, an emissive cavity is strengthened relative to an emissive cavity of a comparative display panel by adjusting the buffer and capping layer thicknesses and refractive indices so that they are less effective in diminishing the reflectivity of the cathode compared to comparative display panel. In some embodiments, a thickness or a material choice or an optical thickness of the buffer layer and/or the capping layer are useful design parameter for adjusting the color shift of the emissive stack.

Figure 15:
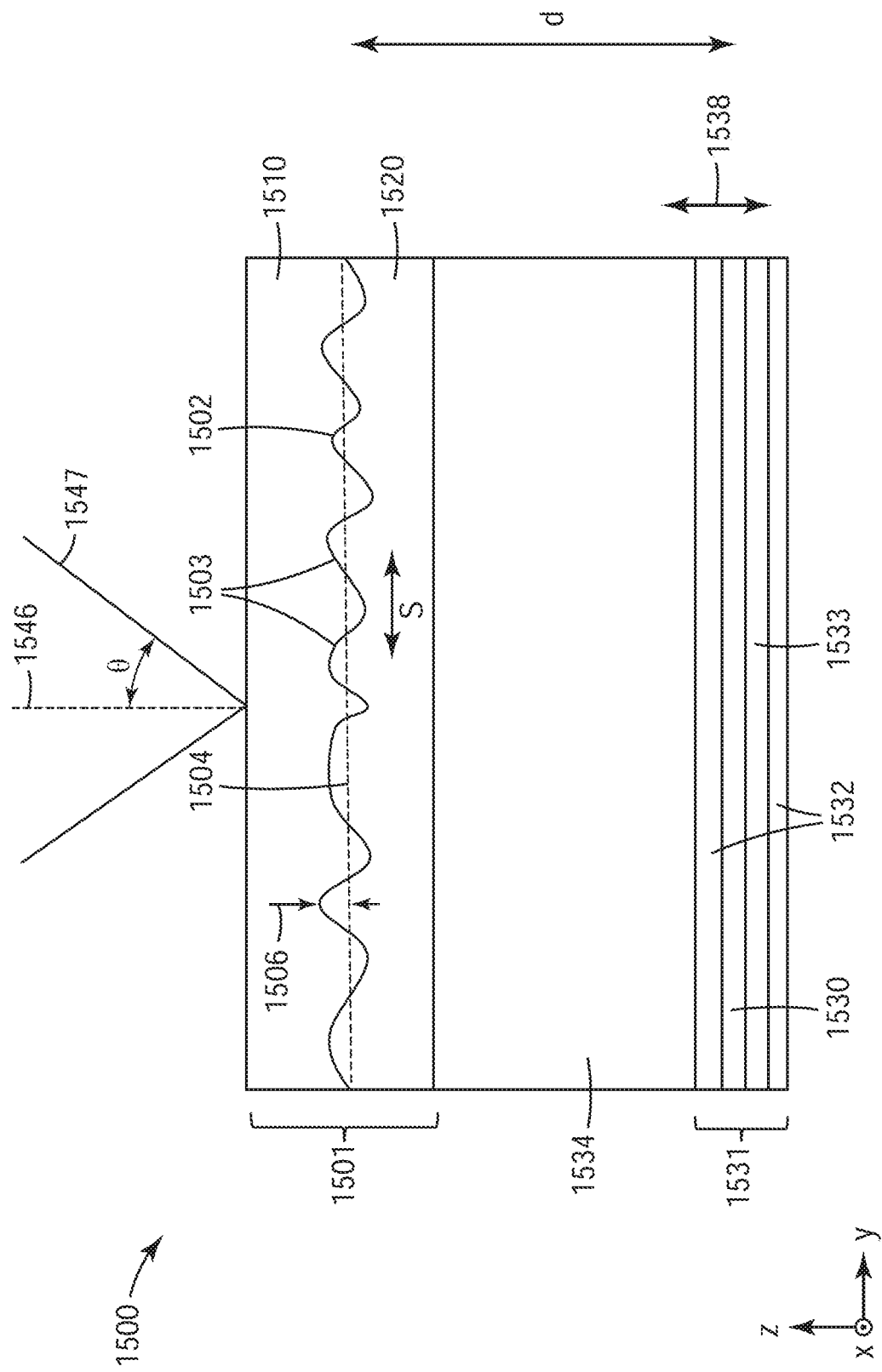
FIG. 15 is a cross-sectional view of an OLED display.

FIG. 15 is a cross-sectional view of an organic light emitting diode (OLED) display 1500 including a color-correction component 1501, which may be referred to as an optical stack, disposed proximate to and outside of an evanescent zone 1538 of an emissive OLED layer 1530. The evanescent zone 1538 typically extends only a few wavelengths of visible light from the emissive OLED layer 1530 in the z-direction. OLED stack 1531 contains emissive OLED layer 1530, electrodes 1532, and hole transport layer 1533. Other layers may also be include as illustrated in FIG. 6, for example. An inner layer 1534 separates the color-correction component 1501 from the emissive OLED layer 1530. Inner layer 1534 may be an encapsulant for the emissive OLED layer 1530 (e.g., corresponding to encapsulant layers 670). The color-correction component 1501 includes nanostructured interface 1502 disposed between first and second layers 1510 and 1520, with the second layer 1520 disposed between the first layer 1510 and the emissive OLED layer 1530. The nanostructured interface 1502 has a displacement 1506, which will be denoted h(x,y), from a mean plane 1504. The nanostructured interface 1502 is disposed at a distance d from the emissive OLED layer 1530. The distance d is the distance from the mean plane 1504 to the top of the emissive OLED layer 1530. In some embodiments, d is at least 5 micrometers, or at least 10 micrometers and in some embodiments, d is no more than 100 micrometers, or no more than 50 micrometers. The nanostructured interface 1502 has a plurality of peaks 1503 and an average spacing S between nearest neighbor peaks. As used herein, averages refer to unweighted arithmetic averages unless specified differently. The variance of the displacement 1506 from the mean plane 1504 of the nanostructured interface 1502 will be denoted Var. FIG. 15 also illustrates a cone of view 1547 for a pixel in the display 1500, the cone of view 1547 has a half-angle θ relative to a normal 1546 to the display 1500. The half-angle θ may be 60 degrees, or 45 degrees, for example.

In some embodiments, the first and second layers 1510 and 1520 are polymeric layers having a continuous polymeric phase. Either of the first and second layers 1510 and 1520 may include inorganic nanoparticles in order to modify the refractive index. Such nanoparticles typically have an average size less than 100 nm (the average size can be determined from the average volume V of the nanoparticles (unweighted arithmetic average) as $(6 V/\pi)^{1/3}$). In some embodiments, a tool having a desired nanostructured surface is used to form the first layer 1510 in a continuous cast and cure process as described further elsewhere herein. The second layer 1520 can be formed by backfilling a nanostructured surface of the first layer 1510 with a crosslinkable composition, for example. The backfill material can be applied to form the second layer 1520 using, for example, one of the following methods: liquid coating; vapor coating; powder coating; lamination; dip-coating; or roll-to-roll coating. In some embodiments, the backfill material forms a planar surface opposite the nanostructured interface. Each of the first and second layers 1510 and 1520 may be continuous layers (e.g., a layer with a continuous polymeric phase). Each of the first and second layers 1510 and 1520 may be solid layers (e.g., hard or soft polymeric layers).

The first layer 1510 may be a crosslinked resin layer and may have a refractive index in the range of 1.2 to 1.6, or in the range of 1.4 to 1.55, for example. The refractive index refers to the refractive index measured at 632 nm, unless specified differently or unless the context clearly indicates differently. In some embodiments, the second layer 1520 has a refractive index of at least 1.4, or at least 1.5, or at least 1.6, or at least 1.7, or at least 1.75. In some embodiments, the second layer 1520 has a refractive index of no more than 2.2, or no more than 2.1, or no more than 2.0. In some embodiments, the second layer 1520 has a refractive index larger than that of the first layer 1510. The first and second layers 1510 and 1520 provide a refractive index contrast (absolute value of the difference in the refractive index of the second layer 1520 and the refractive index of the first layer 1510) across the nanostructured interface 1502. In some embodiments, the refractive index contrast is constant along the nanostructured interface 1502. In some embodiments, the refractive index contrast is in a range of 0.1, or 0.2, or 0.3 to 1.0. In some embodiments, the first layer 1510 is an ultralow refractive index material, such as those described in U.S. Pat. App. Pub. No. 2012/0038990 (Hao et al.), and has a refractive index in a range of 1.2 to 1.35 and the second layer 120 is a high index layer having a refractive index greater than 1.6 or greater than 1.7.

Typically, it is desired to have a large refractive index contrast, since diffracted power transmitted through the nanostructured interface is proportional to the square of the refractive index contrast, and this can be achieved by utilizing a high refractive index material for the second layer 1520. Examples of suitable materials for the second layer 1520 include the following: high index inorganic materials; high index organic materials; a nanoparticle filled polymer material; silicon nitride; polymers filled with high index inorganic materials; and high index conjugated polymers. Examples of high index polymers and monomers are described in C. Yang, et al., Chem. Mater. 7, 1276 (1995), and R. Burzynski, et al., Polymer 31, 627 (1990) and U.S. Pat. No. 6,005,137, all of which are incorporated herein by reference to the extent that they do not contradict the present description. Examples of polymers filled with high index inorganic materials are described in U.S. Pat. No. 6,329,058. Examples of nanoparticles for the nanoparticle filled polymer material include the following high index materials: $TiO_2$, $ZrO_2$, $H_fO_2$, or other inorganic materials.

In some embodiments, the nanostructured interface 1502 has a substantially azimuthally symmetric power spectral density (PSD). The PSD is given by taking the magnitude squared of the two-dimensional Fourier transform of the displacement h(x,y), also denoted h($\vec{x}$), where $\vec{x}$=(x,y) is a vector in the x-y plane, over an area of the x-y plane and dividing by the area for an area sufficiently large compared to an average spacing between peaks in h(x,y) so that the ratio of the magnitude squared of the Fourier transform to the area is approximately independent of the area. The PSD at a wavevector, $\vec{k}$, (also denoted k), can be expressed as $$PSD(\vec{k}) = \frac{1}{A}\left|\int_A d^2 x \, e^{-i\vec{k}\cdot\vec{x}} h(\vec{x})\right|^2$$

for sufficiently large area, A. Typically, the average spacing is less than 1 micrometer and a square area 10 micrometers by 10 micrometers is a sufficiently large area for determining the PSD. PSDs have units of length to the fourth power. It follows from the definition of the PSD that the two-dimensional Fourier space integral of the PSD is equal to $(2\pi)^2$ times the variance Var of the displacement from the mean displacement of the nanostructured interface. It has been found that utilizing the substantially azimuthally symmetric power spectral densities described herein are useful for providing a desired color correction without significantly altering on-axis output (e.g., brightness, color and contrast) of the OLED display when the PSD is suitably chosen.

Figure 16:
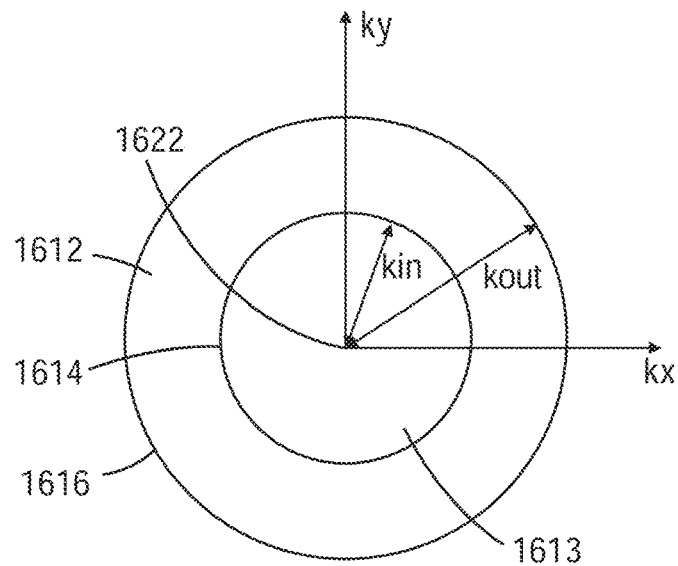
FIG. 16 is a schematic illustration of a region in Fourier space in which the power spectral density (PSD) of a nanostructured interface is concentrated.

FIG. 16 is a schematic illustration of a region in Fourier space in which the power spectral density (PSD) of a nanostructured interface is concentrated. Annulus 1612 is a two-dimensional region in Fourier space bounded by inner circle 1614 and outer circle 1616, both of which are centered at zero wavenumber 1622. Inner circle 1614 has a radius of kin, which may be described as the inner wavenumber of the annulus 1612, and outer circle 1616 has a radius of kout, which may be described as the outer wavenumber of the annulus 1612. The integral of the PSD over all of Fourier space is $(2\pi)^2$ times the variance Var, which is described elsewhere herein. In some embodiments, the integral in Fourier space of the PSD over the area 1613 contained in and bound by the circle 1614 is no more than 4 times Var, or no more than 2 times Var, or no more than Var. In some embodiments, the integral of the PSD over the two-dimensional annulus 1612 in Fourier space is between 0.8 and 1.0 times $(2\pi)^2$ times Var, or between 0.9 and 1.0 times $(2\pi)^2$ times Var. In some embodiments, the integral of the PSD over the two-dimensional annulus 1612 in Fourier space is about $(2\pi)^2$ times Var. In some embodiments, kin is 6 radians/micrometer times the second refractive index, or 8 radians/micrometer times the second refractive index, or 9 radians/micrometer times the second refractive index, or 10 radians/micrometer times the second refractive index, or 12 radians/micrometer times the second refractive index, or 13 radians/micrometer times the second refractive index, or 14 radians/micrometer times the second refractive index. In some embodiments, kout is 10 radians/micrometer times the sum of the second refractive index and 0.8, or 12 radians/ micrometer times the sum of the second refractive index and 0.8, or 13 radians/micrometer times the sum of the second refractive index and 0.8, or 14 radians/micrometer times the sum of the second refractive index and 0.866, or 16 radians/ micrometer times the sum of the second refractive index and 0.9. In some embodiments, kin is in a range of $2\pi$ radians/ (700 nanometers) times the second refractive index to $2\pi$ radians/(400 nanometers) times the second refractive index. In some embodiments, kin is in a range of $2\pi$ radians/(600 nanometers) times the second refractive index to $2\pi$ radians/ (500 nanometers) times the second refractive index. In some embodiments, kout is in a range of $2\pi$ radians/(700 nanometers) times the sum of the second refractive index and 0.8 to $2\pi$ radians/(400 nanometers) times the sum of the second refractive index and 0.9. In some embodiments, kout is in a range of $2\pi$ radians/(600 nanometers) times the sum of the second refractive index and 0.866 to $2\pi$ radians/(500 nanometers) times the sum of the second refractive index and 0.866.

Any point in Fourier space away from the origin defines a wavevector from the origin to the point. The wavevector of light propagating in a medium is a unit vector in the propagation direction times the refractive index of the medium times $2\pi$ divided by the free-space wavelength of the light. The magnitude of a wavevector is referred to as a wavenumber. As used herein, wavevectors and wavenumbers are expressed in radians per unit length even if the radians are not explicitly stated. The PSD is a function of a two-dimensional wavevector and when the PSD is azimuthally symmetric, the PSD is a function of a wavenumber. The product of the PSD evaluated at a wavevector and the magnitude of the wavevector will be referred to herein as a wavenumber-PSD product which in general is a function of the wavevector and when the PSD is azimuthally symmetric, the wavenumber-PSD product is a function of the wavenumber.

When light with an incident wavevector is incident in a medium on a nanostructured interface having a displacement h(x,y) with a peak to peak amplitude that is small compared to the wavelength of the incident light in the medium and light with a transmitted wavevector is diffracted by the nanostructured interface, the diffracted power transmitted through the nanostructured interface is approximately proportional to the PSD evaluated at the difference between the horizontal components of the transmitted and incident wavevectors (e.g., the projection of the transmitted and incident wavevectors onto the x-y plane of FIG. 15). Light with an incident wavevector of magnitude $(2\pi/\lambda)(n2)$, where n2 is the refractive index of the second layer (e.g., layer 1520) and λ is a characteristic wavelength of light from the emissive OLED layer, can diffract into a direction normal to the display if the light is incident on the nanostructured interface at a high incidence angle (so that the horizontal projection of the incident wavevector has a magnitude of approximately $(2\pi/\lambda)(n2)$) with a transmitted diffracted power proportional to the PSD evaluated at $(2\pi/\lambda)(n2)$. Since it is often desired for the light output normal to the display to be substantially unaltered by the presence of the nanostructured interface, it may be desired for kin to be no less than $(2\pi/\lambda)(n2)$. As described further elsewhere herein, in some cases it may be desired that the nanostructured interface does not significantly alter the light output for view angles in air relative to the normal to the display less than a certain angle φ. In such cases, it may be desired for kin to be no less than $(2\pi/\lambda)(n2+\sin\varphi)$.

The PSD at wavenumbers between kin and kout provide a gradual increase in diffractive transmission for increasing view angles relative to the normal to the display since the area in Fourier space contributing to diffractive transmission gradually increases. It has been found that this gradual increase in diffractive transmission provides a gradual increase in color mixing which results in improved color uniformity. Light incident on the nanostructured interface with a wavevector having a horizontal component with a magnitude larger than $(2\pi/\lambda)(n2+\sin\theta)$ cannot diffract into a view angle less than θ degrees relative to the normal to the display. If θ is the maximum view angle (e.g., the half-angle of the view cone of the display which may be 60 degrees, for example), then the portion of the PSD with wavenumbers above $(2\pi/\lambda)(n2+\sin\theta)$ do not significantly contribute to diffractive transmission into the view cone of the display. Accordingly, in some embodiments, kout is no more than $(2\pi/\lambda)(n2+\sin\theta)$.

The characteristic wavelength λ chosen to determine kin may be different from that chosen to determine kout. For example, the characteristic wavelength for determining kin may be based on the wavelengths of red emitters in the OLED display while the characteristic wavelength for determining kout may be based on the wavelengths of blue emitters in the OLED display. This may be done to ensure that the nanostructured interface provides the desired color mixing effect for all colors in the view cone of the display. In other embodiments, it may be advantageous for one color subpixel to be shifted more than the other subpixels and the characteristic wavelength λ may be taken to be the wavelength for that color subpixel in determining both kin and kout. For example, in some embodiments, it is desired that the nanostructured interface provides a substantially stronger color correction for blue subpixels than for green subpixels, and an even smaller (or substantially zero) color correction for red subpixels than for green subpixels. In this case, the characteristic wavelength λ can be taken to be a wavelength (e.g., a peak wavelength) of the blue subpixels.

Figure 17A:
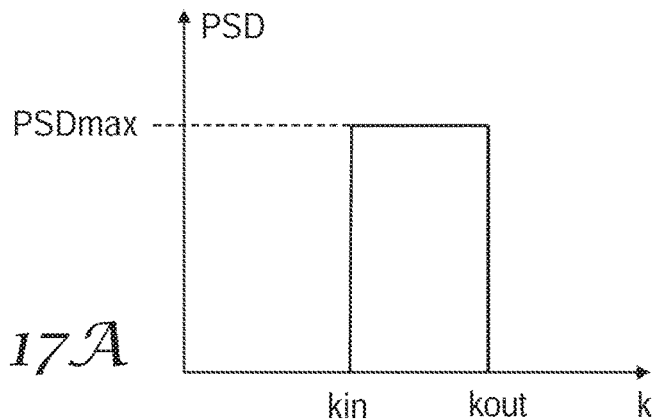
FIG. 17A is a schematic illustration of a PSD of a nanostructured interface as a function of wavenumber.
Figure 17B:
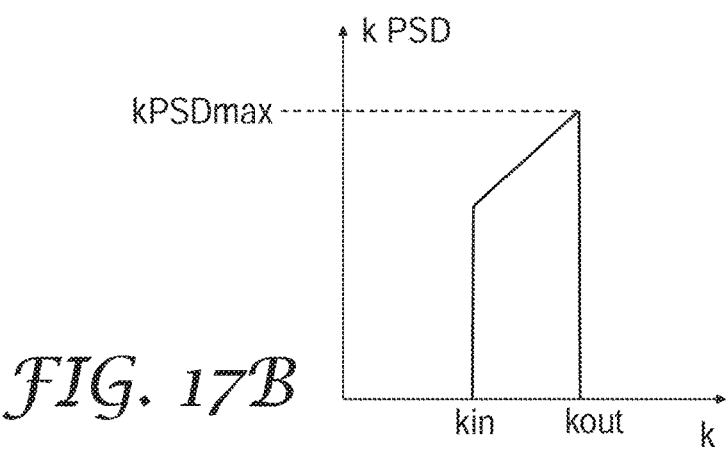
FIG. 17B is a schematic illustration of a wavenumber-PSD product of a nanostructured interface as a function of wavenumber.

FIG. 17A is an idealized schematic illustration of the PSD of a nanostructured interface as a function of wavenumber. In this idealized case, the PSD is non-zero only between kin and kout and it has a constant magnitude in this wavenumber range equal to the maximum value of PSDmax. In other cases, the PSD may not be zero for wavenumbers k less than kin, may not be constant for k between kin and kout, and may not be zero for k greater than kout. The diffracted power through the nanostructured interface is determined by a two-dimensional integral in Fourier space over an integrand proportional to the PSD. This two-dimensional integral has a differential area element $d^2k$ which is given by k dk dφ in polar coordinates with angular coordinate φ. Therefore, the diffracted power through the nanostructured interface is determined by an integral over wavenumber and angular coordinate of an integrand proportional the product of the wavenumber and the PSD evaluated at a wavevector having the magnitude of the wavenumber. This product is referred as the wavenumber-PSD product. FIG. 17B is an idealized schematic illustration of the wavenumber-PSD product (denoted kPSD) of a nanostructured interface as a function of the wavenumber. The wavenumber-PSD product kPSD has a maximum value of kPSDmax.

Figure 18A:
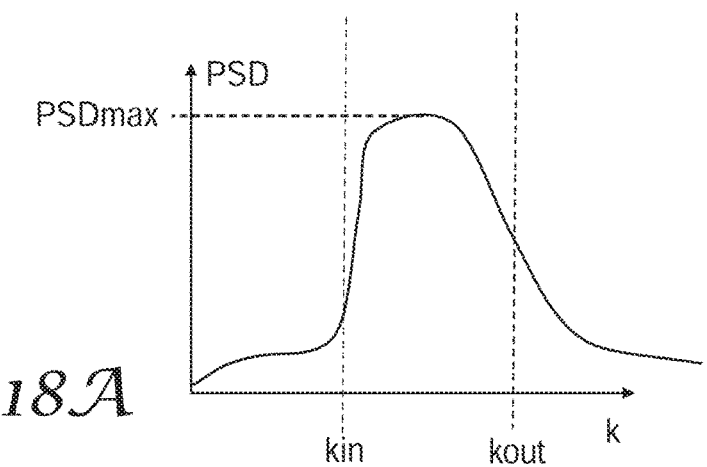
FIG. 18A is a schematic illustration of a PSD of a nanostructured interface as a function of wavenumber.
Figure 18B:
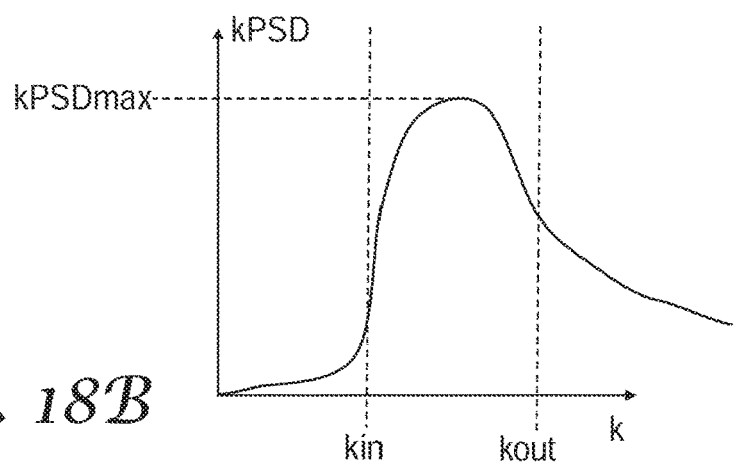
FIG. 18B is a schematic illustration of a wavenumber-PSD product of a nanostructured interface as a function of wavenumber.

FIG. 18A is a schematic illustration of the PSD of another nanostructured interface as a function of wavenumber. The PSD has a maximum, PSDmax, occurring for a wavenumber which is larger than kin and which is smaller than kout. In some embodiments, the wavenumbers kin and kout are taken to be points on either side of the maximum PSDmax where the PSD is 0.5, or 0.3, or 0.2, or 0.1 times its maximum value. In some embodiments, the wavenumbers kin and kout are taken to be points on either side of the maximum kPSDmax where the kPSD is 0.5, or 0.3, or 0.2, or 0.1 times its maximum value. FIG. 18B is a schematic illustration of the product of the wavenumber and the PSD of a nanostructured interface (the wavenumber-PSD product denoted kPSD) evaluated at the wavenumber as a function of the wavenumber. The wavenumber-PSD product kPSD has a maximum value of kPSDmax. In some embodiments, for all wavenumbers less than kin, the PSD is no more than 0.5 times PSDmax, or no more than 0.3 times PSDmax, or no more than 0.2 times PSDmax, or no more than 0.1 times PSDmax. In some embodiments, for all wavenumbers less than kin, the wavenumber-PSD product is no more than 0.3 times kPSDmax, or no more than 0.2 times kPSDmax, or no more than 0.1 times kPSDmax, or no more than 0.05 times kPSDmax. In some embodiments, the preceding ranges hold when the PSD and the wavenumber-PSD product are replaced with their respective annularly averaged values, which is described elsewhere herein, and when PSDmax is replaced with the maximum of the annularly averaged PSD and kPSDmax is replaced with the maximum of the annularly averaged wavenumber-PSD product.

In some embodiments, the two-dimensional integral in Fourier space over the annulus between kin and kout is between 0.8 and 1.0 times $(2\pi)^2$ times Var where Var is the variance of the displacement from the mean displacement of the nanostructured interface. In some embodiments, the two-dimensional integral in Fourier space over the area in the circle having a radius kin and over the region outside a circle having a radius of kout totals no more than 0.2 times $(2\pi)^2$ times Var.

In some embodiments, the PSD is concentrated between kin and kout, but there is substantial contribution (e.g., the PSD may be above 0.05 times PSDmax, or above 0.1 times PSDmax) from wavenumbers larger than kout. This can result from using a tool, as described elsewhere herein, in forming the nanostructured interface where the tool has abrupt changes in height resulting in high wavenumber contributions to the PSD. It is believed that such long wavenumber contributions typically do not significantly affect the color output uniformity of an OLED display including the nanostructured interface.

An average of a quantity (e.g., PSD or wavevector-PSD product) over a region in Fourier space refers to the integral of the quantity over the region divided by the area of the region. An annular average of a PSD (or a wavenumber-PSD product) at a wavenumber is an average of the PSD (or the wavenumber-PSD) product over an annulus in Fourier space having an inner radius of 0.9 times the wavenumber and an outer radius of 1.1 times the wavenumber. In some embodiments, an annular average of the PSD has a maximum for a wavenumber larger than k1 times the second refractive index, and the PSD is no more than 0.1, or 0.2, or 0.3 times the maximum annular average for wavenumbers less than k1 times the second refractive index, for at least one k1 in a range of 6 to 9 radians/micrometer. In some embodiments, an annular average of the wavenumber-PSD product has a maximum for a wavenumber larger than k1 times the second refractive index, and the wavenumber-PSD product is no more than 0.1, or 0.2, or 0.3 times the maximum annular average for wavenumbers less than k1 times the second refractive index, for at least one k1 in a range of 6 to 9 radians/micrometer.

The wavenumbers kin and kout of FIGS. 17A-18B may take any of the values described elsewhere herein in connection with FIG. 16.

Figure 19:
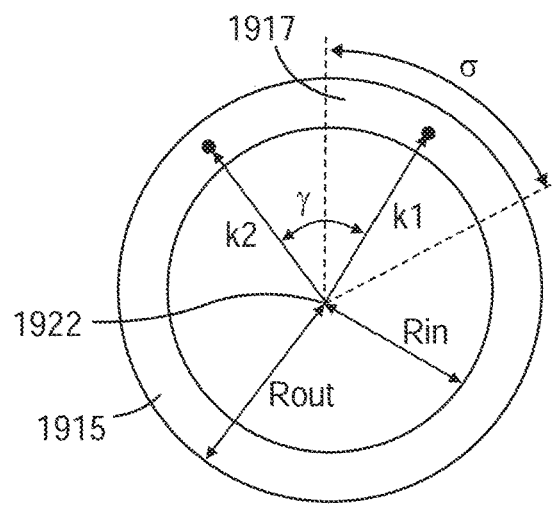
FIG. 19 illustrates an annular sector and an annulus in Fourier space.

FIG. 19 illustrates an annulus 1915 including an annular sector 1917 useful in describing substantial azimuthal symmetry. The annulus 1915 and annular sector 1917 are determined by a first wavevector k1 having a first magnitude k1. The annulus 1915 is the region in Fourier space bounded by an inner radius Rin of 0.9 times the first magnitude k1 and an outer radius Rout of 1.1 times the first magnitude k1. The annulus 1915 is centered on the zero wavenumber 1922. The annular sector 1917 is centered on the first wavevector k1 and has a subtended angle of σ. The annular sector is a portion of the annulus 1915 extending an azimuthal angle of one half σ on either side of k1. As used herein, a power spectral density is substantially azimuthally symmetric if for any first wavevector k1 having a first magnitude k1 between 10 radians/micrometer times the second refractive index and 13 radians/micrometer times a sum of the second refractive index and 0.8, a maximum difference between a local average of the power spectral density at the first wavevector k1 is between 0.67 and 1.33 times the annular average of the power spectral density at the first wavevector k1, where the local average is an average of the power spectral density over an annular sector 1917 in Fourier space centered on the first wavevector k1 and having an inner radius Rin of 0.9 times the first magnitude, an outer radius Rout of 1.1 times the first magnitude k1, and a subtended angle of σ, where the annular average is an average of the power spectral density over an annulus 1915 in Fourier space having an inner radius Rin of 0.9 times the first magnitude k1 and an outer radius Rout of 1.1 times the first magnitude k1, and where σ is equal to 60 degrees.

In some embodiments, for any first wavevector k1 having a first magnitude k1 between 10 radians/micrometer times the second refractive index and 13 radians/micrometer times a sum of the second refractive index and 0.8, the maximum difference between the local average of the power spectral density at the first wavevector k1 is between 0.7 and 1.3 times, or between 0.8 and 1.2 times, or between 0.9 and 1.1 times the annular average of the power spectral density at the first wavevector k1.

In some embodiments, the PSD is still substantially azimuthally symmetric when a smaller annular sector is used in determining whether the PSD is substantially azimuthally symmetric. For example, in some embodiments, the PSD is substantially azimuthally symmetric when the subtended angle σ is equal to 30 degrees.

The range between 10 radians/micrometer times the second refractive index and 13 radians/micrometer times a sum of the second refractive index and 0.8 is used in defining substantially azimuthal symmetry since it has been found that the resulting color uniformity provided by the nanostructure interface is typically more sensitive to this range than other ranges. The PSD may also be approximately azimuthally symmetric within a broader wavenumber range. In some embodiments, for any first wavevector k1 having a first magnitude k1 between 6 radians/micrometer times the second refractive index, or 8 radians/micrometer times the second refractive index, or 10 radians/micrometer times the second refractive index and 13 radians/micrometer times a sum of the second refractive index and 0.8, or 14 radians/micrometer times a sum of the second refractive index and 0.9, a maximum difference between a local average of the power spectral density at the first wavevector k1 is between 0.7 and 1.3, or between 0.8 and 1.2, times the annular average of the power spectral density at the first wavevector k1, where the local average is an average of the power spectral density over an annular sector 517 in Fourier space centered on the first wavevector k1 and having an inner radius Rin of 0.9 times the first magnitude, an outer radius Rout of 1.1 times the first magnitude k1, and a subtended angle of σ, where the annular average is an average of the power spectral density over an annulus 1915 in Fourier space having an inner radius Rin of 0.9 times the first magnitude k1 and an outer radius Rout of 1.1 times the first magnitude k1, and where σ is equal to 60 degrees or equal to 30 degrees.

The PSD may have some degree of azimuthal variability and still be considered substantially azimuthally symmetric. In some embodiments, a substantially azimuthally symmetric PSD has an n-fold symmetry axis. This means that the PSD has the same value for any two wavevectors having a common magnitude that separated by an angle of 360 degrees divided by n. For example, the wavevectors k1 and k2 of FIG. 19 have a same magnitude k1 and are separated by an angle γ. If a PSD has a common value at any two such pairs of wavevectors and if γ is 360 degrees divided by n, the PSD may be described as having an n-fold symmetry. In some embodiments, a substantially azimuthally symmetric power spectral density has at least a 6-fold rotation symmetry.

Nanostructured interfaces having the power spectral densities described elsewhere herein can be made using a tool having a nanostructured surface. In some embodiments, the tool includes a plurality of particles partially embedded in a substrate. Useful techniques for making the tool are described in U.S. Pat. Appl. No. 2014/0193612 (Yu et al.) and U.S. Pat. No. 8,460,568 (David et al.). The nanostructured surface of the tool can be characterized by atomic force microscopy (AFM) and this can be used to determine the PSD of the surface via fast Fourier transform, for example. In brief summary, the tool can be made by disbursing particles in a polymeric precursor matrix to form a layer. The layer is then dried or cured. This can be done by applying heat to evaporate a solvent or applying actinic radiation to cure the layer. In some cases, the layer is heated to remove solvent and then actinic radiation is applied to cure the layer. The layer can then be etched (e.g., reactive ion etched) to form the tool. The tool can then be used to form a nanostructured surface in a first layer which can then be backfilled to form an optical stack having a nanostructured interface. The nanostructured surface can be formed in a continuous cast and cure process where σ resin is cast against the tool and cured, for example, with actinic (e.g., ultraviolet) radiation or heat. Examples of continuous cast and cure processes are described in the following patents: U.S. Pat. Nos. 4,374,077; 4,576,850; 5,175,030; 5,271,968; 5,558,740; and 5,995,690.

The tool produces a nanostructured interface having an average spacing which will be denoted S. The particles are typically randomly agglomerated and so the particles are typically not on a periodic lattice. The average spacing of a nanostructured interface can be defined as an average peak to peak nearest neighbor distance, which in the case of the tool corresponds to an average center to center distance between neighboring particles. The particles have an average size which will be denoted D. In the case of monodispersed spherical particles this is the diameter of the particles. In other cases, the average size D is determined from the average volume V of the particles (unweighted arithmetic average over the particles used in forming the nanostructured interface) as $D=(6 \, V/\pi)^{1/3}$.

Utilizing a sufficiently high loading of particles in the layer results in a substantially azimuthally symmetric PSD for the nanostructured interface since the particles randomly agglomerate in an approximately azimuthally symmetric way. The size of the particles, D, and the loading of the particles, or the resulting average center to center spacing, S, of the particles, can be selected to determine the wavenumbers kin and kout illustrated in FIGS. 17A-18B. Typically, choosing a high loading of the particles will result in a PSD substantially azimuthally symmetric and localized in a thin region in Fourier space (kout not much greater than kin). A high loading means that when the tool is formed the particles are nearly closely packed in a layer. Reducing the particle loading increases S and moves the wavenumber kin to smaller values. Generally, the wavenumber kout is inversely proportional to the size D of the particles and the wavenumber kin is inversely proportional to the spacing S between particles. Thus, by selecting the length scales D and S for the tool, a nanostructured surface can be made that has a substantially azimuthally symmetric PSD that is concentrated between kin and kout as in FIGS. 17A-18B, for example.

In some embodiments, when the tool is etched to form the nanostructured interface, post-like structures with the particles and the top of the posts are formed. Such post-like structures give high wavenumber contributions to the resulting PSD. These high wavenumber contributions are believed to not significantly affect the color uniformity performance of the OLED displays incorporating the resulting nanostructured interfaces. The height of the posts can be controlled by the etching process. Reducing the heights reduce the high wavenumber contribution to the PSD and so increases the PSD between kin and kout.

Further details on useful nanostructured interfaces for a color-correction component and on methods of making the nanostructured interfaces can be found in described in U.S. Prov. Appl. Nos. 62/342,620 (Freier et al.) and 62/414,127 (Erickson et al.), and in PCT Publication No. WO 2017/205174 (Freier et al.).

Figure 20A:
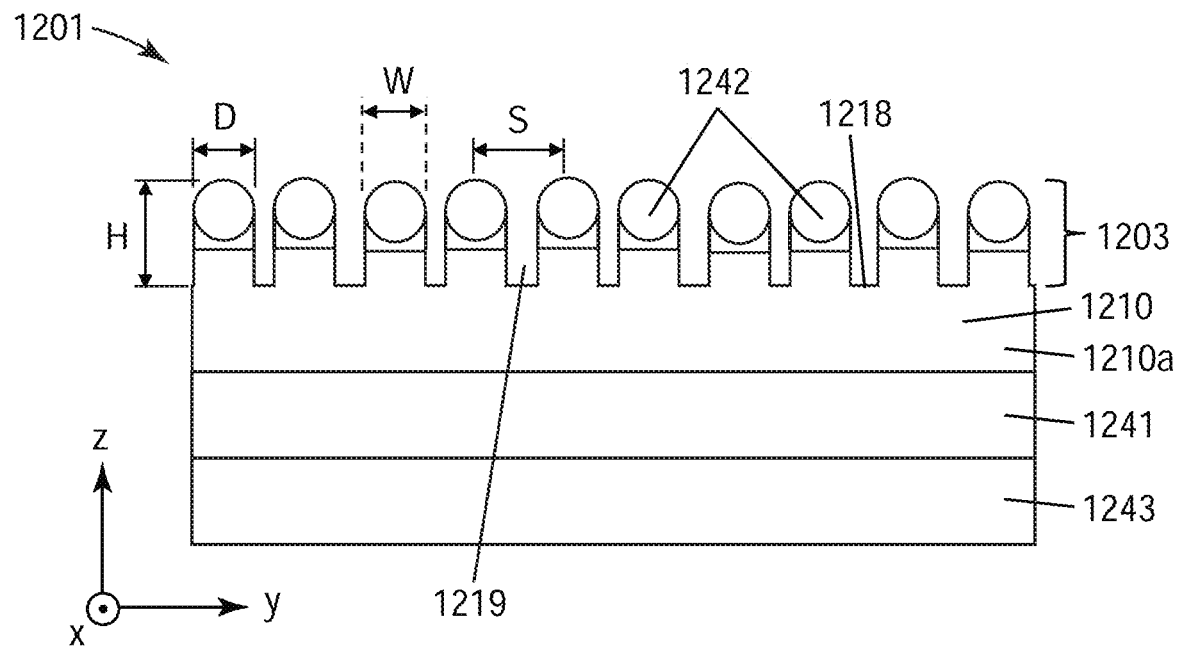
FIG. 20A is a cross-sectional view of a nanostructured article including a nanostructured surface having a plurality of pillars.

FIG. 20A is a schematic cross-sectional view of nanostructured article 1201 including first layer 1210 which has a nanostructured surface 1202 including a plurality of pillars 1203 extending from a base surface 1218, which is the portion of the nanostructured surface 1202 between the pillars 1203. Nanostructured article 1201 can be used to provide a color-correction component by removing the first release liner 1243 and optionally backfilling the nanostructured surface 1202. Pillars 1203 have an average lateral dimension W, an average height H, and an average center-to-center spacing S. Each of the pillars 1203 includes a nanoparticle 1242. The nanoparticles 1242 have an average diameter D. The etch layer 1210a is the portion of layer 1210 which is etched in forming the pillars 1203. The term nanostructured article may refer any article having a nanostructured surface or a nanostructured interface between two layers. A nanostructured surface or interface is a structure or interface having at least one dimension in a range of 1 nm to 1000 nm. In some cases, a nanostructure has each lateral dimension or all three dimensions in a range of 1 nm to 1000 nm, or in a range of 10 nm to 1000 nm. The first layer is disposed generally in the x and y-directions and the pillars 1203 extend generally in the z-direction. Nanostructured article 1201 includes a first release liner 1243 and a transfer layer 1241 disposed between the first layer 1210 and the first release liner 1243. The first layer 1210 and/or the transfer layer 1241 may be or include polymeric layers. In some embodiments, the first layer 1210 is formed by first applying a layer of a monomer or oligomer to the transfer layer 1241 and crosslinking the layer to form the polymer in situ, e.g., by flash evaporation and vapor deposition of a radiation-crosslinkable monomer, followed by crosslinking using, for example, an electron beam apparatus, UV light source, electrical discharge apparatus or other suitable device to form etch layer 1210a. Etch layer 1210a is then etched (e.g., by plasma etching as described generally in U.S. Pat. Appl. Pub. No. 2014/0193612 (Yu et al.) and U.S. Pat. No. 8,460,568 (David et al.), both of which are hereby incorporated herein by reference to the extent they do not contradict the present description) as described further elsewhere herein to form the pillars 1203 in first layer 1210. In some embodiments, the transfer layer 1241 is made as described in WO 2013/116103 (Kolb et al.) and WO 2013/116302 (Kolb et al.), which are hereby incorporated herein by reference to the extent that they do not contradict the present description. The release liner 1243 can be any conventional release treated film, such as a silicone-coated polyethylene terephthalate (PET) film, for example. Other useful materials for the first layer 1210, the transfer layer 1241 and the first release liner 1243 are described further elsewhere herein.

Using different materials for the etch layer 1210a and the transfer layer 1241 allows the etch layer 1210a to be selected for improved etching properties or for desired optical properties of the nanostructured surface 1202 and allows the transfer layer 1241 to be selected for improved coatability on release liner 1243 or improved release properties from the release liner 1243. In addition, the thickness and physical properties of the transfer layer 1241 may be chosen to improve the mechanical properties of the construction. This may help mitigate negative effects such as cracking of the construction during the transfer process and in use. The transfer layer may be chosen to alleviate stress in the backfill (BF) layer that can lead to cracking. In some embodiments the BF layer includes heavily loaded inorganic nanoparticles in a binder. In some cases, this causes the BF layer to be very brittle and prone to cracking. In other embodiments, the transfer layer 1241 is omitted and the etch layer 1210a is disposed on the first release liner 1243. In this case, the etch layer 1210a may be regarded as a transfer layer and can be prepared from materials described elsewhere herein for either an etch layer or a transfer layer. The transfer layer 1241 can also add additional functionality to the nanostructured article. For example, the transfer layer 1241 can have desired moisture or oxygen barrier properties or can be used to provide ultraviolet (UV) light blocking properties, for example. In some embodiments, the transfer layer 1241 has a thickness at least equal to the average pillar height.

The spaces 1219 between the lower portions 1203a (see FIG. 20B) of the pillars 1203 may be referred to as depressions and the pillars 1203 may be referred to as protrusions of the nanostructured surface 1202. Nanostructures other than pillars are also in the scope of the present description where portions of the nanostructured surface extending above an average height of the nanostructures are protrusions and portions of the nanostructured surface below an average height of the nanostructures are depressions.

Figure 20B:
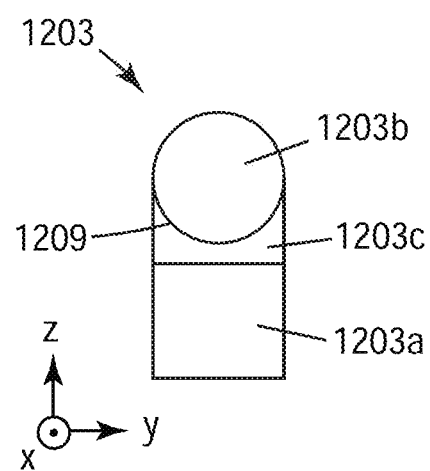
FIG. 20B is a cross-sectional view of a pillar of the nanostructured article of FIG. 20A.

FIG. 20B is a schematic side-view of a pillar 1203 of the nanostructured article of FIG. 20A. Pillar 1203 includes a lower portion 1203a, an upper portion 1203b, and an intermediate portion 1203c. In some embodiments, as described further elsewhere herein, the intermediate portion 1203c includes a matrix material or a binder which was not removed in an etching process used to make the pillars 1203. In some embodiments, the pillars have a circular cross-section. In other embodiments, the pillars may have other cross-sections, such as a tapered rectangular cross-section, for example. In some embodiments, the lower portion 1203a is cylindrical and the nanoparticle of upper portion 1203b is spherical. In some embodiments, the nanoparticle has a diameter substantially equal to a diameter of the lower portion. The nanoparticles can be any nanoparticles which can function as an etch mask in forming the pillars 1203. In some embodiments, the nanoparticles are inorganic nanoparticles such as $SiO_2$ nanoparticles. In other embodiments, the nanoparticle may be a silicone nanoparticle which can act as an etch mask. Other suitable nanoparticles are described further elsewhere herein. In some embodiments, the upper portion 1203b is surface treated and covalently bonded to intermediate portion 1203c along the interface 1209 as described further elsewhere herein. In any of the embodiments described herein, the upper portion (mask portion) of the nanostructures may be covalently bonded to a binder which is attached to the lower portion of the nanostructures.

The upper portion 1203b and the lower portion 1203a have differing compositions. In some embodiments, the lower portion 1203a includes a polymeric material and the upper portion 1203b includes an inorganic material. In some embodiments, the lower portion 1203a includes a polymeric material at at least 60 weight percent and the upper portion 1203b includes an inorganic material at at least 80 weight percent. In some embodiments, the upper portion 1203b includes or consists essentially of a nanoparticle (i.e., the upper portion 1203b may include a nanoparticle and possibly include residue of a binder that was not fully removed by the etching process used to make the pillars, and possibly other impurities on the nanoparticle that do not substantially affect the optical performance of the nanostructured article). In some embodiments, the lower portion 1203a is a polymer or has a continuous polymeric phase. Nanoparticles can also be included in lower portion 1203a. Preferably such nanoparticles are smaller than the nanoparticle of the upper portion 1203b. For example, a plurality of nanoparticles having a diameter less than about 100 nm, or less than about 50 nm, or less than about 40 nm, may be included in the lower portion 1203a in order to modify the refractive index of the lower portion 1203a. In some embodiments, the lower portion 1203a is free of nanoparticles having diameters larger than half of the diameter of the nanoparticle of the upper portion 1203b.

In some embodiments, the nanoparticle of the upper portion 1203b and a material of the lower portion 1203a are selected such that the refractive indices of the lower and upper portions 1203a and 1203b are approximately equal. In some embodiments, the absolute value of the refractive index difference between the lower portion 1203a and the upper portion 1203b is no more than 0.1, or no more than 0.05. Such refractive index ranges apply to any pillars described herein having different upper and lower portions. In some embodiments, the absolute value of the refractive index difference between the lower portion 1203a and the intermediate portion 1203c is no more than 0.1, or no more than 0.05. In some embodiments, the absolute value of the refractive index difference between the upper portion 1203b and the intermediate portion 1203c is no more than 0.1, or no more than 0.05. Such refractive index ranges apply to any pillars described herein having different upper, lower and intermediate portions.

In some embodiments, a second layer is disposed over the plurality of pillars 1203 and extends continuously to the base surface 1218. The second layer can be formed by backfilling the nanostructured surface 1202 of the first layer 1210 with a crosslinkable composition, for example. The backfill material can be applied to form the second layer using, for example, one of the following methods: liquid coating; vapor coating; powder coating; lamination; dip-coating; or roll-to-roll coating. In some embodiments, the backfill material forms a planar surface opposite the nanostructured surface. In some embodiments, the second layer is a high index backfill material. Examples of suitable high index backfill materials include the following: high index inorganic materials; high index organic materials; a nanoparticle filled polymer material; silicon nitride, indium tin oxide, zinc sulfide or a combination thereof; polymers filled with high index inorganic materials; and high index conjugated polymers. Examples of high index polymers and monomers are described in C. Yang, et al., Chem. Mater. 7, 1276 (1995), and R. Burzynski, et al., Polymer 31, 627 (1990) and U.S. Pat. No. 6,005,137, all of which are hereby incorporated herein by reference to the extent that they do not contradict the present description. Examples of polymers filled with high index inorganic materials are described in U.S. Pat. No. 6,329,058, which is hereby incorporated herein by reference to the extent that it does not contradict the present description. The high index inorganic materials may be nanoparticles having a size less than 100 nm, or less than 50 nm, or less than 40 nm, for example. Examples of nanoparticles for a nanoparticle filled polymer material include the following high index materials: $TiO_2$, $ZrO_2$, $H_fO_2$, or other inorganic materials.

The nanostructured surface 1202 or the corresponding nanostructured interface between the nanostructured surface 1202 and an adjacent second layer may have a power spectral density (PSD) as described further elsewhere herein.

Figure 21:
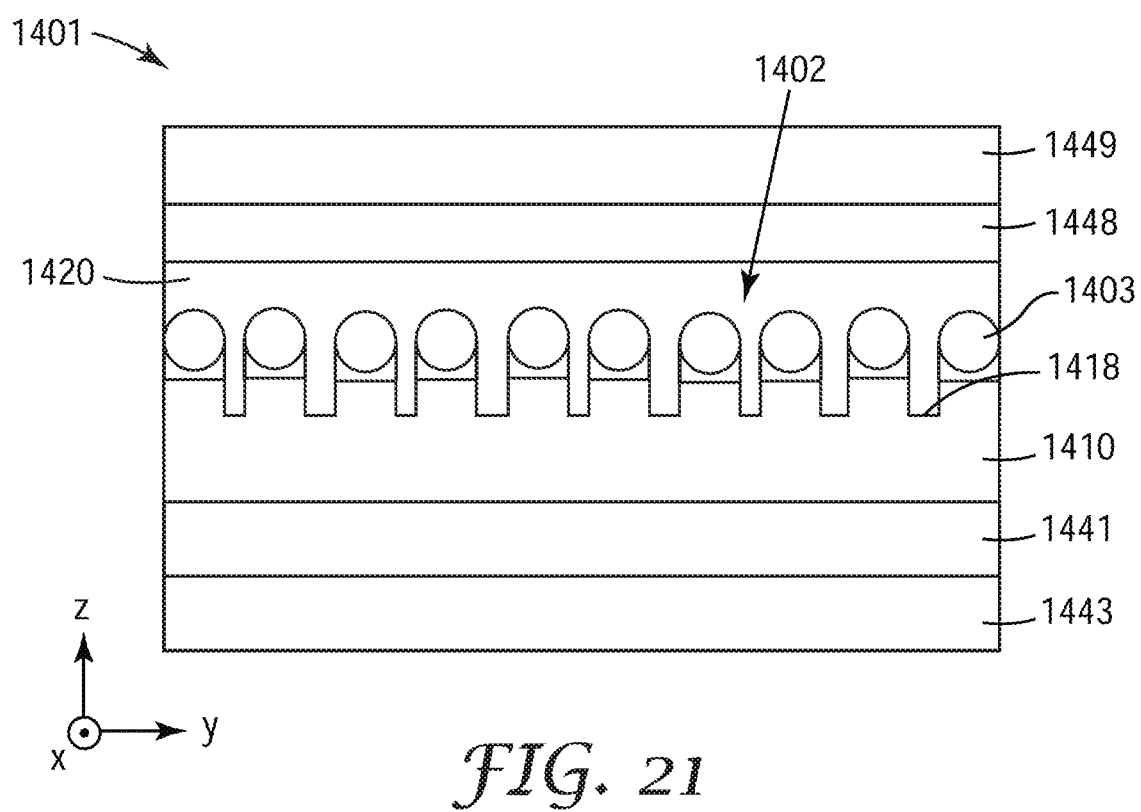
FIG. 21 is cross-sectional view of a nanostructured article.

FIG. 21 is a schematic cross-sectional view of nanostructured article 1401 including first layer 1410 which has a nanostructured surface 1402 including a plurality of pillars 1403 extending from a base surface 1418 of the first layer 1410. Nanostructured article 1401 further includes a transfer layer 1441 disposed on a first release liner 1443, a second layer 1420 disposed over the plurality of pillars 1403 and extending continuously to the base surface 1418, an adhesive 1448 disposed on the second layer 1420 opposite the first layer 1410, and second release liner 1449 disposed on the adhesive 1448 opposite the second layer 1420. The first layer 1410 can be deposited as described for first layer 1210, for example, or as described for other substrate layers described elsewhere herein. The first and second release liners 1443 and 1449 can be any release liner described elsewhere herein. The adhesive 1448 can be an optically clear adhesive (OCA), for example. Illustrative OCAs include those described in publication WO 2008/128073 relating to antistatic optically clear pressure sensitive adhesive, U.S. Patent Application Publications US 2009/030084 relating to stretch releasing OCA; US 2009/0087629 relating to indium tin oxide compatible OCA; US 2010/0028564 relating to antistatic optical constructions having optically transmissive adhesive; US 2010/0040842 relating to adhesives compatible with corrosion sensitive layers; US 2011/0126968 relating to optically clear stretch release adhesive tape; and US 2011/0253301 relating stretch release adhesive tape. Suitable OCAs include acrylic optically clear pressure sensitive adhesives such as, for example, 3M OCA 8146 available from 3M Company, St. Paul, MN. In some embodiments, the OCA has a thickness in a range of 1 micrometer to 50 micrometers, or in a range of 10 micrometers to 40 micrometers.

The first and second release lines 1443 and 1449 can be removed from nanostructured article 1401 and the adhesive 1448 can be used to attached the remaining layers to an OLED display panel to provide a color-correction component.

Pillars 1403 include lower portions 1403a, upper portions 1403b, and intermediate portions 1403c. In some embodiments, the upper portions 1403b may be collectively referred to as a mask or a mask layer since these portions can be used in forming the pillars 1403 as described further elsewhere herein. In some embodiments, the lower portions of the pillars 1403 have a first refractive index, the second layer 1420 has a second refractive index, the upper portion of the pillars 1403 has a third refractive index, and the intermediate portion of the pillars 1403 has a fourth refractive index. In some embodiments, an absolute value of a difference between the first and third refractive indices is no more than 0.1, or no more than 0.05. In some embodiments, an absolute value of a difference between the first and fourth refractive indices is no more than 0.1. In some embodiments, an absolute value of a difference between the first and second refractive indices is in a range of 0.1 to 1.5.

An interface between the nanostructured surface of the first layer 1410 and the second layer 1420 can have any of the geometries described elsewhere herein. For example, this nanostructured interface may have a PSD as described further elsewhere herein. The refractive index contrasts across the nanostructured interface may be in any of the ranges described elsewhere herein.

In some embodiments, the nanostructured surface has a pillar height distribution with a standard deviation about the average height of the pillars of no more than 10 percent (or no more than 8 percent, or no more than 5 percent, or even no more than 3 percent) of the average pillar height, or less than 20 nm (or less than 15 nm, or even less than 10 nm). The standard deviation and average pillar height can be calculated over a 10 micrometer by 10 micrometer area, for example.

In some embodiments, a color-correction component includes first and second layers and a nanostructured interface therebetween (e.g., as depicted in FIGS. 15 and 21), where the first layer has a first refractive index, the second layer faces the OLED display panel and has a different second refractive index being at least 1.4. The nanostructured interface has a substantially azimuthally symmetric power spectral density, PSD. A wavenumber-PSD product has a maximum for a wavenumber larger than 6 radians/micrometer times the second refractive index. In some embodiments, for all wavenumbers less than 6 radians/micrometer times the second refractive index, the wavenumber-PSD product is no more than 0.3 times the maximum.

In some embodiments, a color-correction is or includes a wavelength and polarization dependent partial reflector. In some embodiments, the partial reflector is a film which may be referred to as a color-correction film. In some embodiments, the partial reflector includes an optical stack which includes a plurality of optical repeat units which provide a desire wavelength and polarization dependent reflectivity and transmissivity.

Wavelength and polarization dependent partial reflectors according to some embodiments of the present description are useful for reducing the color shift with view angle of an organic light emitting diode (OLED) display when the partial reflector is used in a circular polarizer of the OLED display, for example. The partial reflectors may be referred to as reflective polarizers or as partial reflective polarizers since the partial reflectors, in some embodiments, have a reflection band for one polarization state and not for an orthogonal polarization state. The reflection band typically has an average reflectance for normally incident light polarized along a block axis less than 97%, or less than 95%, or less than 90%, or less than 75%, or less than 60%. The reflection band may be weaker than the reflection band of conventional multilayer optical film mirrors or reflective polarizers which typically provide an average reflectance of greater than 98%. The partial reflectors may be birefringent multilayer optical films with controlled band edges and tailored reflectivity with incidence angle. In some embodiments, the partial reflectors are designed to have minimal visual effects on axis when incorporated in a display but create optical gain for desired wavelengths off axis. It has been found that utilizing the partial reflectors of the present description in an OLED display can provide improved color uniformity with varying view angle by providing a wavelength and view angle dependent gain without sacrificing image quality despite the typically diffusive character of the backplane of the OLED display.

In some embodiments, the partial reflector is configured to negligibly affect light from an OLED display at normal incidence to the partial reflector, but provide a wavelength dependent gain at off-normal incidence by recycling a portion of light incident on the partial reflector at off-normal incidence. This can be achieved by choosing the reflection band to be predominately in the near-infrared (wavelengths from 700 nm to 2500 nm) at normal incidence. At off-normal view angles the reflection band is shifted into the red wavelength range (wavelengths from 600 nm to 700 nm) and this can provide a gain for red wavelengths that increases with increasing view angle. In some embodiments, the partial reflector may provide a wavelength dependent gain at normal incidence as well as providing a wavelength dependent gain at off-normal incidence (e.g., by including a second harmonic of a primary reflection band to recycle a portion of the blue light, for example). This can be done to allow additional flexibility in providing the desired light output from the display or to correct the color temperature of light output at normal incidence when the display is set to a white-point light output, for example.

Figure 22:
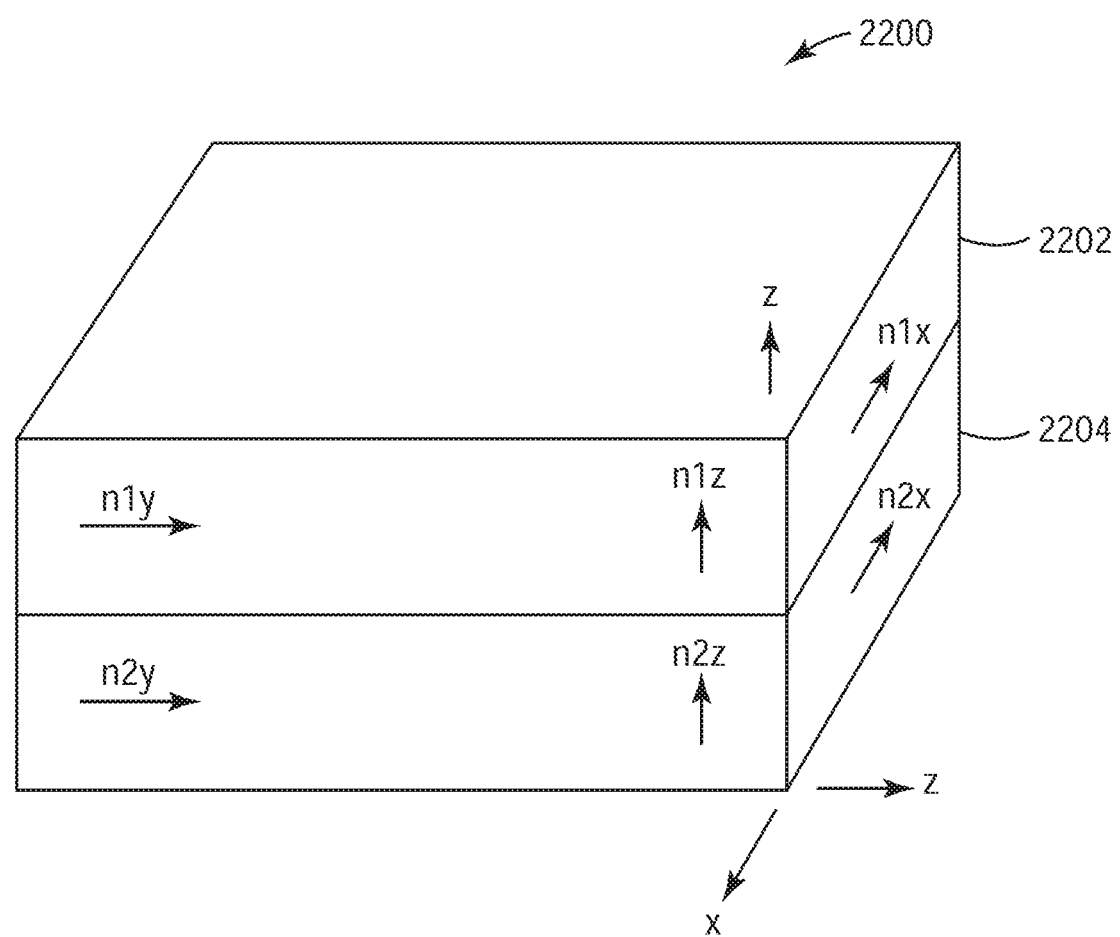
FIG. 22 is a schematic perspective view of an exemplary optical repeat unit of a multilayer optical film.

A wavelength and polarization dependent partial reflector or reflective polarizer of the present description is typically a multilayer optical film that includes an optical stack including a plurality of optical repeat units where each optical repeat unit includes first and second layers which may be polymeric layers. FIG. 22 is a schematic perspective view of an exemplary optical repeat unit (ORU) of a multilayer optical film 2200. FIG. 22 depicts only two layers of the multilayer optical film 2200, which can include tens or hundreds of such layers arranged in one or more contiguous packets or stacks. The film 2200 includes individual microlayers 2202, 2204, where "microlayers" refer to layers that are sufficiently thin so that light reflected at a plurality of interfaces between such layers undergoes constructive or destructive interference to give the multilayer optical film the desired reflective or transmissive properties. The microlayers 2202, 2204 can together represent one optical repeat unit (ORU) of the multilayer stack, an ORU being the smallest set of layers that recur in a repeating pattern throughout the thickness of the stack. The microlayers have different refractive index characteristics so that some light is reflected at interfaces between adjacent microlayers. For optical films designed to reflect light at ultraviolet, visible, or near-infrared wavelengths, each microlayer typically has an optical thickness (i.e., a physical thickness multiplied by the relevant refractive index) of less than about 1 micrometer. Thicker layers can, however, also be included, such as skin layers at the outer surfaces of the film, or protective boundary layers (PBL) disposed within the film that separate packets of microlayers, as desired. In some embodiments, only a single packet or stack of microlayers is included in the optical films of the present description.

Refractive indices of one of the microlayers (e.g. microlayer 2202 of FIG. 22, or the "A" layers of FIG. 23) for light polarized along principal x-, y-, and z-axes are n1x, n1y, and n1z, respectively. The mutually orthogonal x-, y-, and z-axes can, for example, correspond to the principal directions of the dielectric tensor of the material. In many embodiments, and for discussion purposes, the principle directions of the different materials are coincident, but this need not be the case in general. The refractive indices of the adjacent microlayer (e.g. microlayer 2204 in FIG. 22, or the "B" layers in FIG. 23) along the same axes are n2x, n2y, n2z, respectively. The differences in refractive index between these layers are $\Delta nx$ ($=n1x-n2x$) along the x-direction, $\Delta ny$ ($=n1y-n2y$) along the y-direction, and $\Delta nz$ ($=n1z-n2z$) along the z-direction. The nature of these refractive index differences, in combination with the number of microlayers in the film (or in a given stack of the film) and their thickness distribution, control the reflective and transmissive characteristics of the film (or of the given stack of the film). For example, if adjacent microlayers have a large refractive index mismatch along one in-plane direction ($\Delta nx$ large) and a small refractive index mismatch along the orthogonal in-plane direction ($\Delta ny \approx 0$), the film or packet may behave as a reflective polarizer for normally incident light. A reflective polarizer or polarization dependent partial reflector may be considered to be an optical body that relatively strongly transmits normally incident light that is polarized along one in-plane axis, which may be referred to as the pass axis or the first axis, and relatively strongly reflects normally incident light that is polarized along an orthogonal in-plane axis, which may be referred to as the block axis or the second axis, if the wavelength is within a reflection band of the reflective polarizer or polarization dependent partial reflector.

If desired, the refractive index difference ($\Delta nz$) between adjacent microlayers for light polarized along the z-axis can also be tailored to achieve desirable reflectivity properties for the p-polarization component of obliquely incident light. To maintain near on-axis reflectivity of p-polarized light at oblique angles of incidence, the z-index mismatch $\Delta nz$ between microlayers can be controlled to be substantially less than the maximum in-plane refractive index difference $\Delta nx$, such that $|\Delta nz| \leq 0.5*|\Delta nx|$. Alternatively, $|\Delta nz| \leq 0.25*|\Delta nx|$. A zero or near zero magnitude z-index mismatch yields interfaces between microlayers whose reflectivity for p-polarized light is constant or near constant as a function of incidence angle. Furthermore, the z-index mismatch $\Delta nz$ can be controlled to have the opposite polarity compared to the in-plane index difference $\Delta nx$, e.g., $\Delta nz<0$ when $\Delta nx>0$. This condition yields interfaces whose reflectivity for p-polarized light increases with increasing angles of incidence, as is the case for s-polarized light. If $\Delta nz>0$, then the reflectivity for p-polarized light decreases with angle of incidence. The foregoing relationships also of course apply to relationships involving $\Delta nz$ and $\Delta ny$, e.g., in cases where significant reflectivity and transmission are desired along two principal in-plane axes (such as a partial polarizing film whose pass axis has significant reflectivity at normal incidence).

Figure 23:
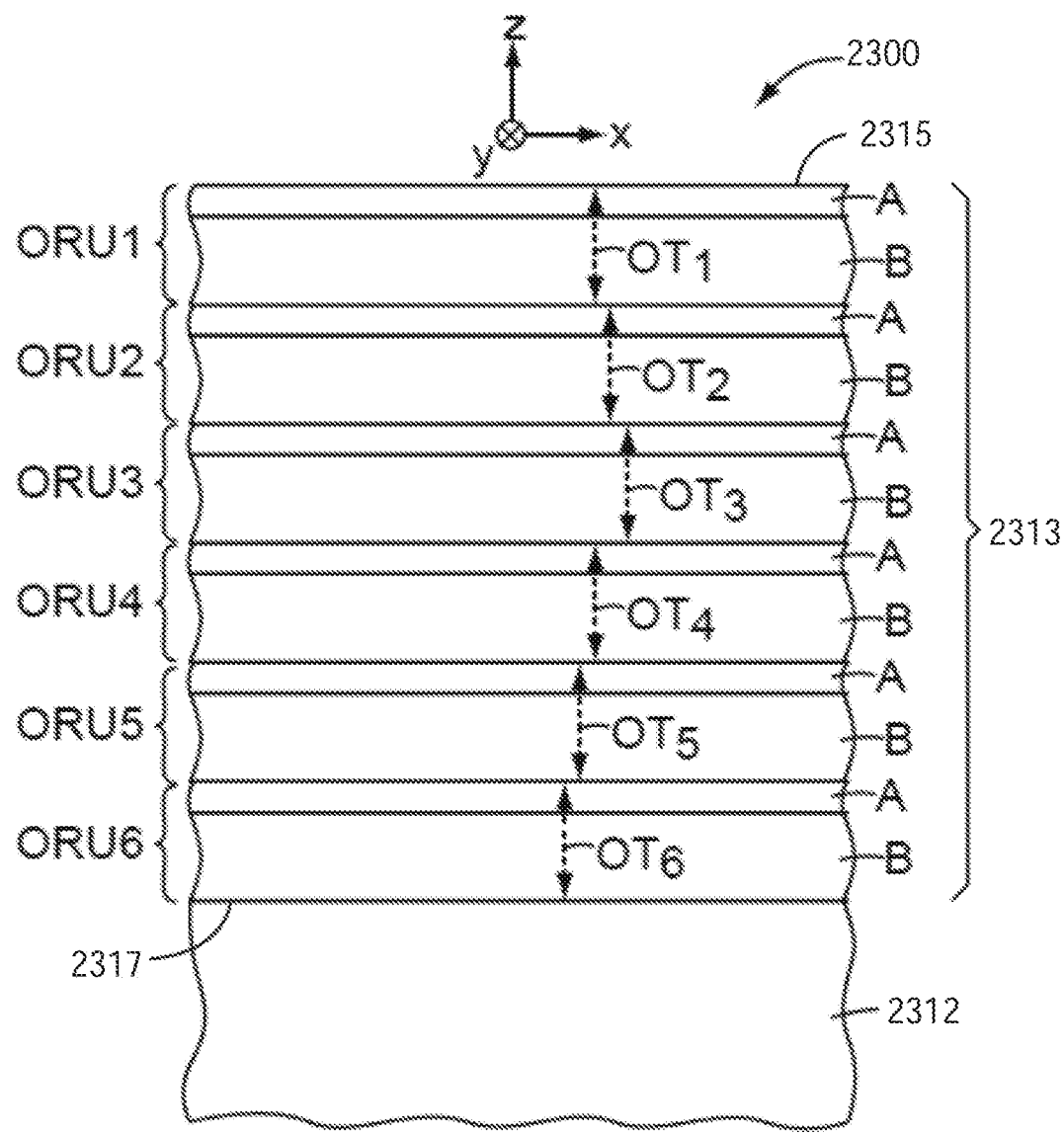
FIG. 23 is a schematic side view of a partial reflector.

In the schematic side view of FIG. 23, more interior layers of a multilayer optical film 2310 are shown so that multiple ORUs can be seen. The film is shown in relation to a local x-y-z Cartesian coordinate system, where the film extends parallel to the x- and y-axes, and the z-axis is perpendicular to the film and its constituent layers and parallel to a thickness axis of the film.

In FIG. 23, the microlayers are labeled "A" or "B," the "A" layers being composed of one material and the "B" layers being composed of a different material, these layers being stacked in an alternating arrangement to form optical repeat units or unit cells ORU 1, ORU 2, . . . ORU 6 as shown. In some embodiments, a multilayer optical film composed entirely of polymeric materials would include many more than 6 optical repeat units if high reflectivities are desired. In other embodiments, as few as 6 or 8 microlayers may be used when at least some of the microlayers include inorganic materials, for example. The multilayer optical film 2310 is shown as having a substantially thicker layer 2312, which may represent an outer skin layer, or a protective boundary layer ("PBL," see U.S. Pat. No. 6,783, 349 (Neavin et al.)) that may separate the stack of microlayers shown in the figure from another stack or packet of microlayers (if present), or a substrate layer. Multilayer optical film 2310 includes a single stack 2313 having opposing first and second sides 2315 and 2317.

In some embodiments, the thicker layer 2312 is optically thick in that it is too thick to significantly contribute to the constructive and destructive interference provided by the optical stack. In some embodiments, an optically thick layer has at least one of a physical thickness and an optical thickness that is at least 1 micrometer, or at least 2 micrometers, or at least 3 micrometers, or at least 5 micrometers. In some embodiments, a circular polarizer used in an OLED display includes a partial reflector of the present description disposed between a linear absorbing polarizer and a retarder for improved color uniformity with view angle.

In some cases, the microlayers of a given stack or packet can have thicknesses and refractive index values corresponding to a ¼-wave stack, i.e., arranged in ORUs each having two adjacent microlayers of equal optical thickness, such ORU being effective to reflect by constructive interference light whose wavelength $\lambda$ is twice the overall optical thickness of the optical repeat unit. The "optical thickness" of a body refers to its physical thickness multiplied by its refractive index. In the case of a polarization dependent partial reflector, the refractive index used in determining the optical thickness is the refractive index along the axis of the partial reflector where the reflection band reflects more strongly (e.g., the block axis of a reflective polarizer). A ¼-wave stack, in which the two adjacent microlayers in each ORU have equal optical thickness, is said to have an "f-ratio" of 0.5 or 50%. "F-ratio" in this regard refers to the ratio of the optical thickness of a constituent layer "A" to the optical thickness of the complete optical repeat unit, where the constituent layer "A" is assumed to have a higher refractive index than the constituent layer "B"; if the layer "B" has the higher refractive index, then the f-ratio is the ratio of the optical thickness of the constituent layer "B" to the optical thickness of the complete optical repeat unit. The use of a 50% f-ratio is often considered desirable because it maximizes the reflective power of the $1^{st}$ order (primary) reflection band of a stack of microlayers. However, a 50% f-ratio suppresses or eliminates the $2^{nd}$ order (second harmonic) reflection band (and higher even orders). This too is often considered desirable in many applications; however, as described further elsewhere herein, it may not be desirable to suppress the $2^{nd}$ order reflection band in some applications since a second harmonic of a primary reflection band can be utilized to provide additional flexibility in achieving a desired color output. For example, in some embodiments, a second harmonic is used to provide reflection in the blue wavelength range. Furthermore, according to some embodiments, it may be desired for the reflection band to have a relatively low reflectance. In this case, a smaller f-ratio (or an f-ratio closer to unity), along with the total number of layers and the difference in refractive indices between layers in an optical repeat unit, can be chosen to provide a desired reflectivity. The relative reflective powers of a primary reflection band and of harmonics of the primary reflection band as a function off-ratio is described in U.S. Pat. No. 9,279,921 (Kivel et al.), for example, which is hereby incorporated herein by reference to the extent that it does not contradict the present description.

In some embodiments, the f-ratio is in a range of 0.06, or 0.1, or 0.2 to 0.4 or in a range of 0.6 to 0.8, or 0.9, or 0.94.

In other embodiments, the f-ratio is in a range of 0.4 to 0.6, for example. In the embodiment of FIG. 23, the "A" layers are depicted for generality as being thinner than the "B" layers. Each depicted optical repeat unit (ORU 1, ORU 2, etc.) has an optical thickness (OT1, OT2, etc.) equal to the sum of the optical thicknesses of its constituent "A" and "B" layer, and each optical repeat unit provides $1^{st}$ order reflection of light whose wavelength A is twice the overall optical thickness of the ORU.

To achieve a desired reflectivity with a reasonable number of layers, adjacent microlayers may exhibit a difference in refractive index ($|\Delta nx|$) for light polarized along the x-axis of at least 0.05, or at least 0.1, or at least 0.15, for example. Adjacent microlayers may exhibit a smaller difference in refractive index ($\Delta ny|$) for light polarized along the y-axis. For example, in some embodiments, $|\Delta ny|$ is no more than 0.04, or no more than 0.02, or no more than 0.01. In some embodiments, the adjacent microlayers may exhibit a refractive index match or mismatch along the z-axis ($\Delta nz=0$ or $|\Delta nz|$ large), and the mismatch may be of the same or opposite polarity or sign as the in-plane refractive index mismatch(es). Whether the reflectivity of the p-polarized component of obliquely incident light increases, decreases, or remains the same with increasing incidence angle can be controlled by such tailoring of $\Delta nz$. The refractive indices and refractive index differences may be specified at a fixed reference wavelength (e.g., 532 nm or 550 nm or 632 nm) or may be specified for each optical repeat unit at the wavelength where the optical repeat unit is configured to reflect.

In some embodiments, the total number of optical repeat units in the optical stack is at least 4, or at least 10, or at least 20, or at least 25, or at least 30, or at least 35, or at least 40. In some embodiments, the total number of optical repeat units is no more than 300, or no more than 200, or no more than 180, or no more than 160, or no more than 150. A larger number of optical repeat units may be used in embodiments with a smaller (or closer to unity) f-ratio, and a smaller number of optical repeat units may be used in embodiments with an f-ratio near 0.5. A lager number of optical repeat units are typically utilized when each alternating layer is polymeric and a smaller number of optical repeat units are typically utilized when at least the high refractive index layers (e.g., microlayer 2202 of FIG. 22, or the "A" layers of FIG. 23) is inorganic. In some embodiments, no more than 26 or no more than 20 microlayers are utilized.

At least some of the microlayers in at least one packet of the multilayer optical films may be birefringent, e.g., uniaxially birefringent. In some cases, each ORU may include one birefringent microlayer, and a second microlayer that is either isotropic or that has a small amount of birefringence relative to the other microlayer. In alternative cases, each ORU may include two birefringent microlayers.

The multilayer optical films can be made using any suitable light-transmissive materials, but in many cases it is beneficial to use low absorption polymer materials. With such materials, absorption of a microlayer stack over visible and infrared wavelengths can be made small or negligible, such that the sum of reflection and transmission for the stack (or an optical film of which it is a part), at any given wavelength and for any specified angle of incidence and polarization state, is approximately 100%, i.e., $R+T \approx 100\%$, or $R \approx 100\%-T$. Exemplary multilayer optical films are composed of polymer materials and may be fabricated using coextruding, casting, and orienting processes. Reference is made to U.S. Pat. No. 5,882,774 (Jonza et al.) "Optical Film", U.S. Pat. No. 6,179,948 (Merrill et al.) "Optical Film and Process for Manufacture Thereof", U.S. Pat. No. 6,783, 349 (Neavin et al.) "Apparatus for Making Multilayer Optical Films", and patent application publication US 2011/0272849 (Neavin et al.) "Feedblock for Manufacturing Multilayer Polymeric Films". The multilayer optical film may be formed by coextrusion of the polymers as described in any of the aforementioned references. The polymers of the various layers may be chosen to have similar rheological properties, e.g., melt viscosities, so that they can be co-extruded without significant flow disturbances. Extrusion conditions are chosen to adequately feed, melt, mix, and pump the respective polymers as feed streams or melt streams in a continuous and stable manner. Temperatures used to form and maintain each of the melt streams may be chosen to be within a range that avoids freezing, crystallization, or unduly high pressure drops at the low end of the temperature range, and that avoids material degradation at the high end of the range.

In brief summary, the fabrication method can include: (a) providing at least a first and a second stream of resin corresponding to the first and second polymers to be used in the finished film; (b) dividing the first and the second streams into a plurality of layers using a suitable feedblock, such as one that includes: (i) a gradient plate including first and second flow channels, where the first channel has a cross-sectional area that changes from a first position to a second position along the flow channel, (ii) a feeder tube plate having a first plurality of conduits in fluid communication with the first flow channel and a second plurality of conduits in fluid communication with the second flow channel, each conduit feeding its own respective slot die, each conduit having a first end and a second end, the first end of the conduits being in fluid communication with the flow channels, and the second end of the conduits being in fluid communication with the slot die, and (iii) optionally, an axial rod heater located proximal to said conduits; (c) passing the composite stream through an extrusion die to form a multilayer web in which each layer is generally parallel to the major surface of adjacent layers; and (d) casting the multilayer web onto a chill roll, sometimes referred to as a casting wheel or casting drum, to form a cast multilayer film. This cast film may have the same number of layers as the finished film, but the layers of the cast film are typically much thicker than those of the finished film. Furthermore, the layers of the cast film are typically all isotropic. A multilayer optical film with controlled low frequency variations in reflectivity and transmission over a wide wavelength range can be achieved by the thermal zone control of the axial rod heater, see e.g., U.S. Pat. No. 6,783,349 (Neavin et al.).

After the multilayer web is cooled on the chill roll, it can be drawn or stretched to produce a finished or near-finished multilayer optical film. The drawing or stretching accomplishes two goals: it thins the layers to their desired final thicknesses, and it may orient the layers such that at least some of the layers become birefringent. The orientation or stretching can be accomplished along the cross-web direction (e.g., via a tenter), along the down-web direction (e.g., via a length orienter), or any combination thereof, whether simultaneously or sequentially. If stretched along only one direction, the stretch can be "unconstrained" (where the film is allowed to dimensionally relax in the in-plane direction perpendicular to the stretch direction) or "constrained" (where the film is constrained and thus not allowed to dimensionally relax in the in-plane direction perpendicular to the stretch direction). The stretch can be asymmetric between orthogonal in-plane directions so that the resulting film will have a polarization dependent reflectivity. In some embodiments, the film may be stretched in a batch process. In any case, subsequent or concurrent draw reduction, stress or strain equilibration, heat setting, and other processing operations can also be applied to the film.

The film may be formed by coextruding one or more sets of films composed of large numbers of microlayers to constitute what is commonly called a packet of typically alternating isotropic and birefringent layers. The packets are typically formed in roll processes where the cross-web dimension is commonly labelled transverse direction (TD) and the dimension along the length of the roll is called machine direction (MD). Furthermore, the packets may be carefully stretched in the forming process in machine direction and transverse direction in carefully controlled temperature zones to affect the birefringent layers in what is commonly referred to as a tentering process. Furthermore, the tentering processes may provide either linear transverse stretch or parabolic stretch of the packets as they are formed. A controlled inward linear retraction commonly referred to as "toe-in" may be used to allow for controlled shrinkage during the cool down zone. The process can be used to provide 30 to 600 layers, for example, or more for desired optical effects and may also include external "skin" layers as needed.

Figure 24A:
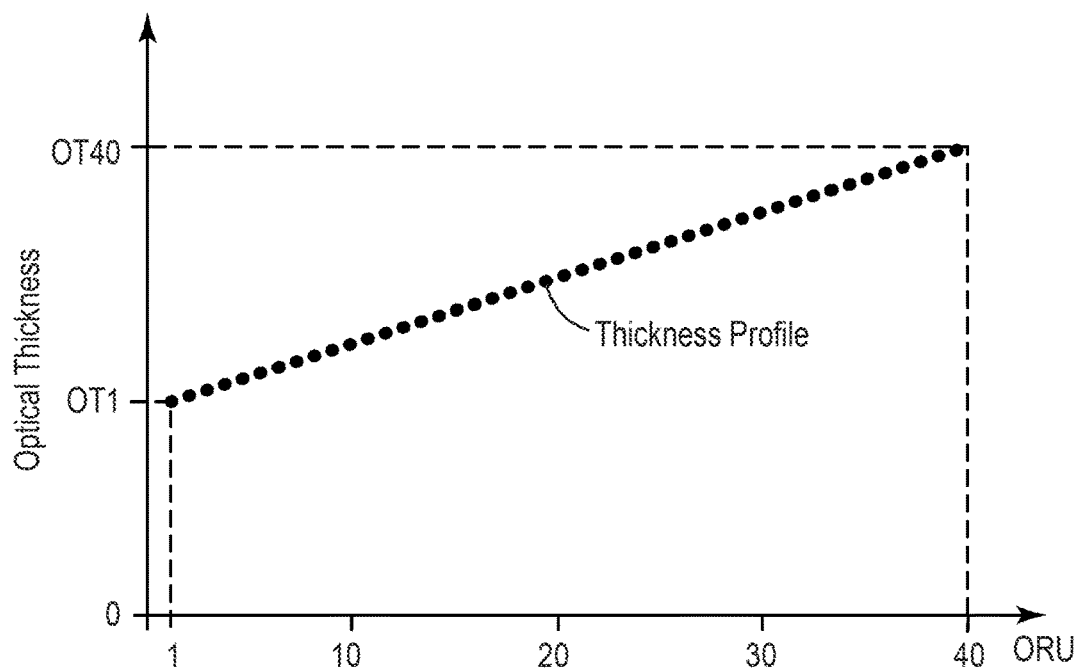
FIGS. 24A-24B are a schematic illustrations of layer thickness profiles of multilayer optical films.

The partial reflectors of the present description typically have a primary (first order) reflection band in the red and/or near infrared and optionally a second harmonic (second order) band partially in the blue. Each wavelength in an $m^{th}$-order band is $1/m$ times a wavelength in the first order band. The location and bandwidth of the higher order bands are therefore determined by the location and bandwidth of the first order band. In order to achieve a desired wavelength range for the primary reflection band and the second harmonic, it is desired that the primary reflection band lie in a suitable wavelength range (e.g., an infrared reflection band with a suitable bandwidth). This can be achieved by tailoring the thickness profile; that is, by tailoring the optical thicknesses of the ORUs according to a thickness gradient along the z-axis or thickness direction of the film, whereby the optical thickness of the optical repeat units increases, decreases, or follows some other functional relationship as one progresses from one side of the stack (e.g., the top) to the other side of the stack (e.g., the bottom). The thickness profile can also be tailored to adjust the slope of the primary reflection band and/or a sharpness of the band edges FIG. 24A is a schematic illustration of a layer thickness profile of an optical film having a single stack of optical repeat units. In this case, 40 optical repeat units are included and the thickness varies linearly across the film. In some embodiments, the layer thickness profile is substantially continuous. A layer thickness profile may be described as substantially continuous if to a good approximation (e.g., to within 10 percent error, or to within 5 percent error, or to within 3 percent error), the optical thickness of any interior optical repeat unit can be determined by linear extrapolation from the optical thickness of the optical repeat units on either side of the interior optical repeat unit.

Figure 24B:
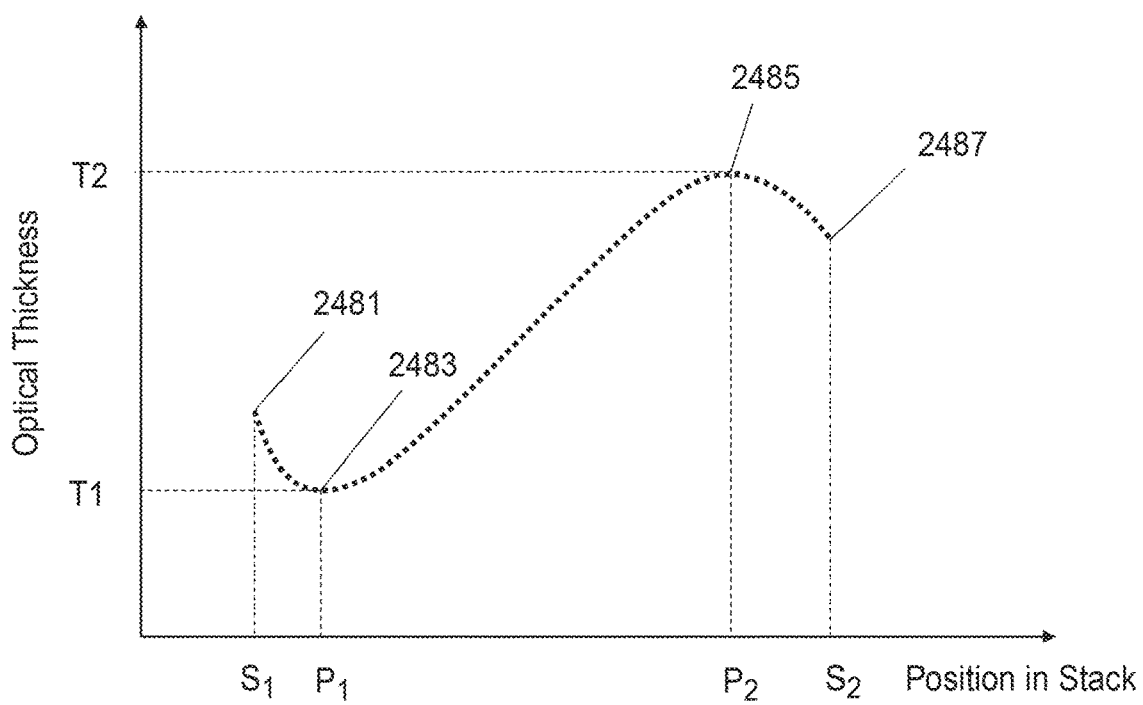

In some embodiments, the optical repeat units have an optical thickness that varies substantially continuously from a first side of the optical stack to an opposing second side of the stack. The thickness variation may be chosen to provide sharpened band edges as described in U.S. Pat. No. 6,157,490 (Wheatley et al.), for example, or may be chosen to provide a more gradual transition from high to low reflectivity. In some embodiments, the optical thickness of the optical repeat units varies between a minimum value and a maximum value, the maximum value minus the minimum value being no more than 35 percent of the maximum value and no less than 5 percent of the maximum value. In some embodiments, the optical thickness monotonically increases from a first side of the single stack to an opposing second side of the single stack. As illustrated in FIG. 24B, which is a plot of the optical thickness of the optical repeat units in a single stack as a function of vertical (z-coordinate of FIG. 23) position in the single stack, in some embodiments, the optical thickness monotonically decreases from an optical repeat unit 2481 at the first side at position $S_1$ of the single stack to an optical repeat unit 2483 (which has a smallest optical thickness T1) within the stack at position $P_1$, monotonically increases from the optical repeat unit 2483 to an optical repeat unit 2485 (which has a largest optical thickness T2) within the single stack at position $P_2$ disposed between the second side at position $S_2$ of the single stack and the optical repeat unit 2483, and monotonically decreases from the optical repeat unit 2485 to the second side at position $S_2$ of the single stack. In some embodiments, a separation between the first and second optical repeat units $(P_2-P_1)$ is at least half, or at least 70%, of a thickness of the single stack $(S_2-S_1)$. Other possible layer profiles include a smile profile (thinner in the middle of the stack than at the edges) and a frown profile (thicker in the middle of the stack than at the edges).

In some embodiments, the thickness variation of the optical repeat units is selected to give a desired slope of the primary reflection band. For example, the primary reflection band may be more reflective at higher wavelengths and less reflective at lower wavelengths, or may be less reflective at higher wavelengths and more reflective at lower wavelengths, or may have a substantially constant reflectivity in the primary reflection band. Adjusting the slope of the reflection band can provide additional flexibility to adjust the reflectivity with incidence angle and thereby adjust the output color of a display with view angle, for example.

In some embodiments, for wavelengths $\lambda 1 < \lambda 2 < \lambda 3$, the partial reflector has a transmittance for normally incident light polarized along a first axis of at least 85% for wavelengths between $\lambda 1$ and $\lambda 3$, and the partial reflector has a first reflection band having band edges at $\lambda 2$ and $\lambda 3$ for normally incident light polarized along an orthogonal second axis. In some embodiments, the partial reflector has an f-ratio of the optical repeat units, a refractive index difference between the first and second polymer layers along the second axis, and a total number of optical repeat units in the optical stack such that the first reflection band has an average reflectance for normally incident light polarized along the second axis between 15% and 97%, or between 15% and 95%, or between 15% and 90%, or between 20% and 85%, or between 20% and 75%, or between 25% and 60%, for example. In some embodiments, the optical repeat units have a range of optical thicknesses such that $(\lambda 3-\lambda 2)/(\lambda 3+\lambda 2)$ is at least 0.03, or at least 0.05, or at least 0.07, and no more than 0.25, or no more than 0.02, or no more than 0.015 (e.g., in a range of 0.05 to 0.2). For example, in some embodiments, the optical repeat units have a smallest optical thickness T1 proximate a first side (e.g., position S1) of the optical stack and a largest optical thickness T2 proximate an opposite second side (e.g., position $S_2$) of the optical stack where $(T2-T1)/(T2+T1)$ is in a range of 0.05 to 0.2 or in any of the ranges described for $(\lambda 3-\lambda 2)/(\lambda 3+\lambda 2)$. A position within the optical stack may be described as proximate a first side of the optical stack if it is closer to the first side than the second side. Similarly, a position within the optical stack may be described as proximate a second side of the optical stack if it is closer to the second side than the first side. In some embodiments, T2 is at least 300 nm, or at least 325 nm, or at least 350 nm, or at least 355 nm, or at least 360 nm, or at least 375 nm. In some embodiments, T2 is no more than 1250 nm, or no more than 800 nm, or no more than 500 nm, or no more than 450 nm.

Figure 25:
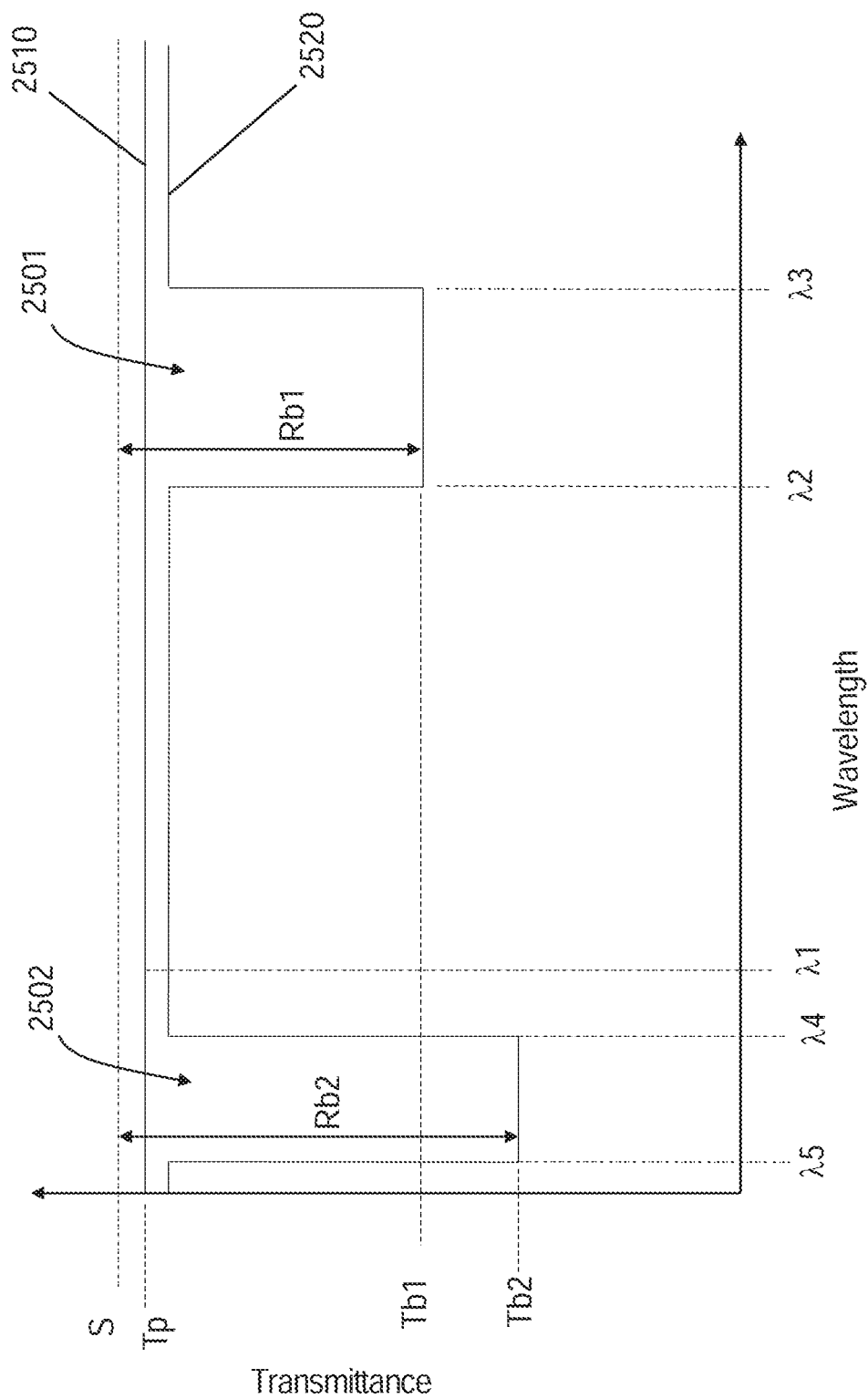
FIG. 25 is a schematic plot of the transmittance versus wavelength of a wavelength and polarization dependent partial reflector.

The transmittance of a wavelength and polarization dependent partial reflector or partial reflective polarizer is schematically illustrated in FIG. 25. In the illustrated embodiment, the transmittance 2510 in the pass state (polarization state with light polarized along a first (pass) axis) for normally incident light has the value Tp which may be at least 85%, or at least 90%, for example. In some embodiments, the transmittance in the pass state for normally incident light is at least 85%, or at least 90% over at least a wavelength range from λ1 to λ3. The transmittance 2520 in the block state (polarization state with light polarized along a second (block) axis) exhibits a first reflection band 2501 and a second reflection band 2502. In some embodiments, the first reflection band 2501 is a primary reflection band and the second reflection band 402 is a second harmonic of the primary reflection band. The first reflection band 2501 has a shorter wavelength band edge of λ2 and a longer wavelength band edge of λ3. In some embodiments, λ2 is about 2 times a smallest optical thickness T1 of the optical stack of the partial reflector, and λ3 is about 2 times a largest optical thickness T2 of the optical stack. The second reflection band 2502 has a shorter wavelength band edge of λ5 and a longer wavelength band edge of λ4. In embodiments where the first reflection band 2501 is a primary reflection band and the second reflection band 2502 is a second harmonic of the primary reflection band, λ5 is about λ2/2 and λ4 is about λ3/2. In some embodiments, the first reflection band 2501 includes near infrared wavelengths (i.e., at least one wavelength between 700 nm and 2500 nm is included in the range from λ2 to λ3). In some embodiments, the second reflection band 2502 includes visible wavelengths (i.e., at least one wavelength in a range of 400 nm to 700 nm (e.g., 400 nm) is included in the range from λ5 to λ4). In other embodiments, λ4 may be less than 400 nm. In some embodiments, λ4 is no more than 500 nm, or no more than 450 nm, or no more than 430 nm, or no more than 410 nm. In some embodiments, λ4 is in a range of 400 nm to 500 nm.

In some embodiments, the first reflection band is a primary reflection band having a band edge λ3 of at least 700 nm, or at least 710 nm, or at least 720 nm, or at least 750 nm. In some embodiments, the band edge λ3 is no more than 2500 nm, or no more than 1500 nm, or no more than 1000 nm, or no more than 900 nm. For example, in some embodiments, λ3 is in a range of 700 nm to 2500 nm, or 710 nm to 1000 nm, or 720 nm to 900 nm, or 750 nm to 900 nm. In some embodiments, the band edge λ2 is at least 600 nm, or at least 610 nm, or at least 620 nm. In some embodiments, λ2 is no more than 750 nm, or no more than 710 nm, or no more than 700 nm, or no more than 690 nm, or no more than 680 nm. For example, in some embodiments, λ2 is in a range of 600 nm to 700 nm, or in a range of 610 nm to 690 nm. In some embodiments, λ1 is no more than 480 nm, or no more than 450 nm, or no more than 420 nm, or no more than 400 nm. In some embodiments, λ1 is at least 380 nm, or at least 400 nm. For example, in some embodiments, λ1 is in a range of 380 nm to 480 nm, or in a range of 400 nm to 450 nm. In some embodiments, λ1 is 400 nm.

In some embodiments, the first reflection band of a partial reflector is centered on a wavelength λc between 900 nm and 980 nm (e.g., 940 nm), for example, and satisfies 0.05≤(λ3−λ2)/(λ3+λ2) 0.2. The partial reflector could be adapted to reflect wavelengths near λc at one angle of incidence but not at another angle of incidence due to the band shift with incidence angle. Such partial reflectors are useful in sensor systems, for example, as described further elsewhere herein.

Figure 26:
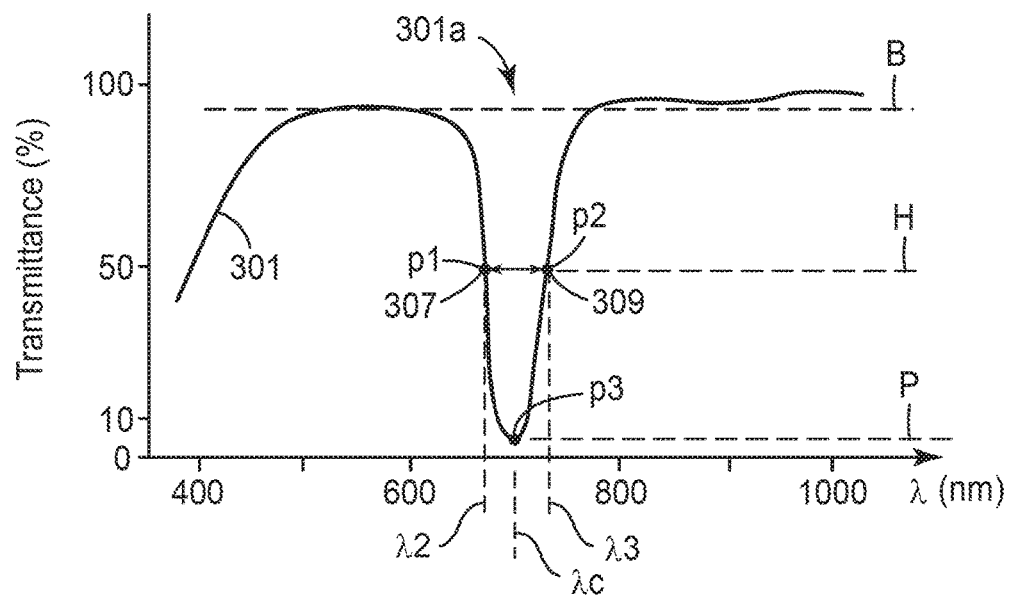
FIG. 26 is a schematic graph of the transmission spectrum of a partial reflector.

The first reflection band 2501 has an average transmittance for normally incident light polarized along the second axis of Tb1. The corresponding average reflectance, Rb1, for normally incident light polarized along the second axis is S-Tb1, where S is the sum of the average reflectance and the average transmittance which may be about 100% neglecting surface reflections and absorption. In some embodiments, the reflectance is not constant over the band width of the reflection band. The average reflectance over a band can be expressed as the integral of the reflectance over wavelengths in the band divided by the width (e.g., λ3−λ2) of the band. In some embodiments, Rb1 is greater than 15%, or greater than 20%, or greater than 25%, or greater than 30%. In some embodiments, Rb1 is less than 97%, or less than 95%, or less than 90%, or less than 75%, or less than 60%. For example, in some embodiments, Rb1 is between 15% and 90%, or between 20% and 75%, or between 25% and 60%. Similarly, in some embodiments, Th1 is between 10% and 85%, or between 25% and 80%, or between 40% and 80%. The second reflection band 402 has an average transmittance for normally incident light polarized along the second axis of Tb2. The corresponding average reflectance, Rb2, for normally incident light polarized along the second axis is S-Tb2. Rb2 may be in any of the ranges described for Rb1. Similarly, Tb2 may be in any of the ranges described for Tb1. Rb2 may be greater than, less than, or about equal to Rb1 depending on the f-ratio of the optical stack of the partial reflector. FIG. 26 is a schematic graph of the transmission spectrum of a hypothetical partial reflector. In this figure, transmittance is plotted against wavelength λ in nanometers, the wavelength axis extending over the range from 400 to 1000 nm. The curve 301 may represent the measured transmittance for light at normal incidence polarized along a block axis. The illustrated reflector selectively blocks light within a narrow band in a portion of the red and near infrared region of the spectrum, evidenced by the relatively low transmittance of the reflection band 301a of the curve 301.

In order to quantify relevant features of the curve 301, a baseline value B of the curve 301, a peak value P of the curve 301 (in this case the peak value P corresponds to a transmittance minimum for the reflection band 301a, shown at point p3), and an intermediate value H of the curve 301, halfway between P and B are identified in FIG. 26. The curve 301 intersects with the value H at the points p1 and p2. These points lie on the shorter wavelength band edge 307 and the longer wavelength band edge 309, respectively, of the reflection band 301a and define the shorter wavelength band edge wavelength λ2 and the longer wavelength band edge wavelength λ3. The shorter and longer wavelength band edge wavelengths can be used to calculate two other parameters of interest: the width (full width at half-maximum, or "FWHM") of the reflection band 301a, which equals λ3−λ2; and the center wavelength λc of the reflection band 301a, which equals (λ2+λ3)/2. Note that the center wavelength λc may be the same as or different from the peak wavelength (see point p3) of the reflection band 301a, depending on how symmetrical or asymmetrical the reflection band 301a is.

The transmittance of an optical element refers generally to the transmitted light intensity divided by the incident light intensity (for light of a given wavelength, incident direction, etc.), but may be expressed in terms of "external transmittance" or "internal transmittance". The external transmittance of an optical element is the transmittance of the optical element when immersed in air, and without making any corrections for Fresnel reflections at the air/element interface at the front of the element or for Fresnel reflections at the element/air interface at the back of the element. The internal transmittance of an optical element is the transmittance of the element when the Fresnel reflections at its front and back surfaces have been removed. The removal of the front and back Fresnel reflections may be done either computationally (e.g. by subtracting an appropriate function from the external transmission spectrum), or experimentally. For many types of polymer and glass materials, the Fresnel reflections are about 4 to 6% (for normal or near-normal angles of incidence) at each of the two outer surfaces, which results in a downward shift of about 10% for the external transmittance relative to the internal transmittance. FIG. 26 does not specify which of these transmittances is used, hence, it may generally apply to either internal or external transmittance. If transmittance is referred to herein without being specified as internal or external, it may be assumed that the transmittance refers to external transmittance, unless otherwise indicated by the context.

In some embodiments, a polymeric multilayer optical film may have a reflection band having a maximum reflectance (e.g., at point p3 in FIG. 26) of at least 15%, or at least 20%, or at least 25%, or at least 30% (or a minimum transmittance that is less than 85%, or less than 80%, or less than 75%, or less than 70%). In some cases, the internal transmittance through the optical film may be at least 80% in regions on either side of the reflection band, or at least 20% higher than the minimum transmittance on either side of the reflection band. For example, in some embodiments, the optical film may have a minimum internal transmittance in the reflection band of less than 40% and may have an internal transmittance of at least 80% at a wavelength 10 nm shorter, or 20 nm shorter, or 30 nm shorter than a shorter wavelength band edge of the reflection band, and/or the optical film may have an internal transmittance of at least 80% at a wavelength 10 nm longer, or 20 nm longer, or 30 nm longer than a longer wavelength band edge of the reflection band.

Figure 27:
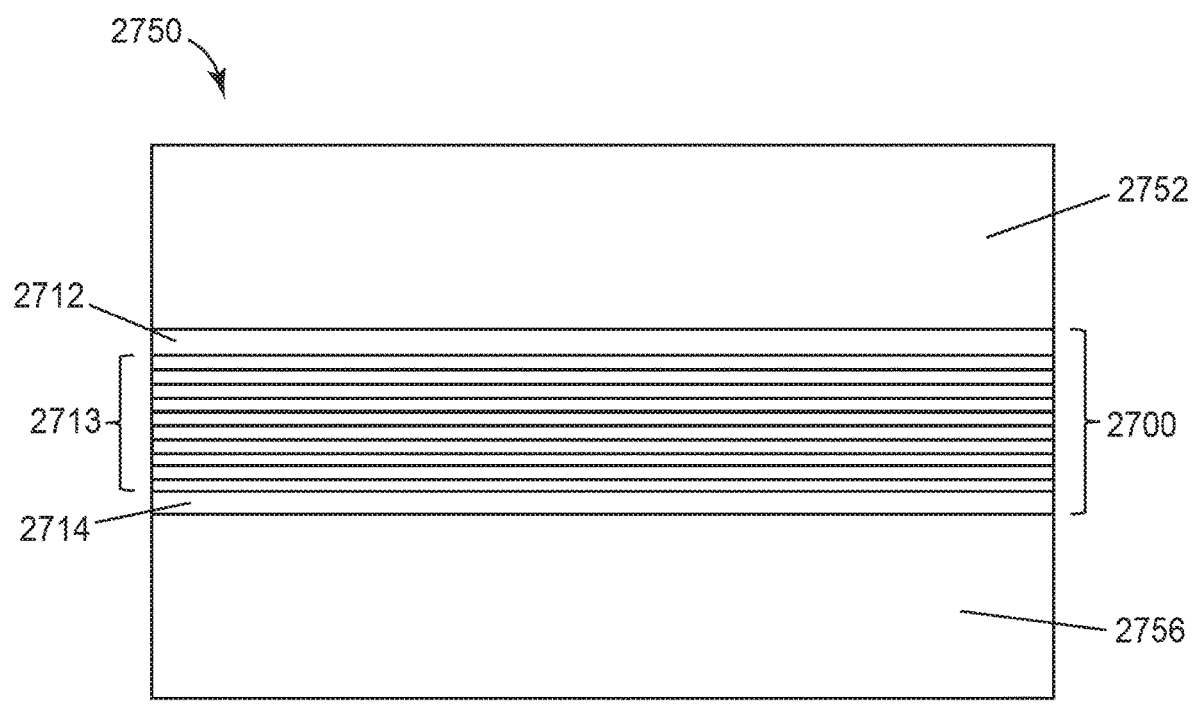
FIG. 27 is a schematic cross-sectional view of a circular polarizer.

The partial reflectors of the present description are useful in display applications and have been found to provide reduced color shift in OLED displays incorporating the partial reflector. In some embodiments, the partial reflector is a color-correcting partial reflector disposed in a circular polarizer between a linear absorbing polarizer and a retarder. FIG. 27 is a schematic cross-sectional view of a circular polarizer 2750 including a linear absorbing polarizer 2752, a partial reflector 2700 and a retarder 2756. The partial reflector 2700 may be any partial reflector described herein. Partial reflector 2700 includes optical stack 2713, which includes plurality of alternating polymer layers, and includes optically thick layers 2712 and 2714. Circular polarizer 2750 can be disposed on a light output surface of an OLED display panel with the retarder 2756 facing the display panel.

In some embodiments, partial reflector 2700 is a reflective polarizer disposed between the linear absorbing polarizer 2752 and the retarder 2756, where the reflective polarizer has a primary reflection band having a shorter wavelength band edge (e.g., λ2 of FIG. 25) at a wavelength of at least 600 nm.

In some embodiments, partial reflector 2700 is a reflective polarizer disposed between the linear absorbing polarizer 2752 and the retarder 2756, where the reflective polarizer includes an optical stack including a plurality of optical repeat units where each optical repeat unit includes first and second polymer layers, and where σ refractive index difference between the first and second polymer layers along a first axis is Δny, a refractive index difference between the first and second polymer layers along an orthogonal second axis is Δnx. In some embodiments, |Δnx| is at least 0.1 and |Δny| is no more than 0.04. In some embodiments, for refractive indices along the second axis, the optical repeat units have a smallest optical thickness T1 proximate a first side of the optical stack and a largest optical thickness T2 proximate an opposite second side of the optical stack. T2 and/or (T2−T2)/(T2+T2) may be in any of the ranges described elsewhere herein. For example, in some embodiments, T2 is at least 300 nm, or at least 350 nm, and/or is no more than 1250 nm.

Figure 28:
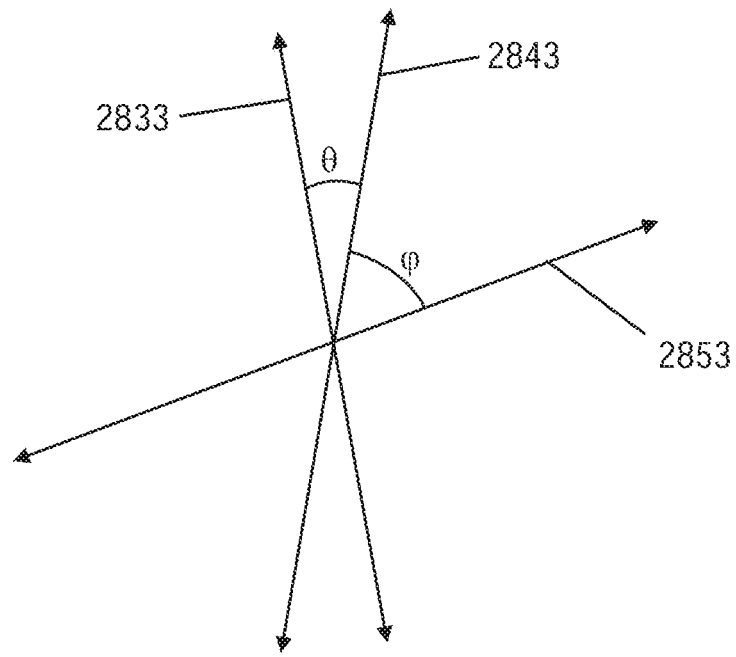
FIG. 28 is a schematic illustration of a pass axis of a partial reflector, a pass axis of a linear absorbing polarizer, and a fast axis of a retarder.

FIG. 28 is a schematic illustration of a first axis 2833 of a partial reflector, which is a pass axis of the partial reflector, and a pass axis 2843 of a linear absorbing polarizer. An angle θ between the pass axis 2843 and the first axis 2833 is illustrated. If the angle θ is less than 20 degrees, the pass axis 2843 may be described as substantially aligned with the first axis 2833. In some embodiments, the angle θ is less than 10 degrees, or less than 5 degrees. A fast axis 2853 of a retarder is also illustrated. The fast axis 2853 makes an oblique angle φ with the pass axis 2843 of the linear absorbing polarizer. In some embodiments, the oblique angle φ is between 40 and 50 degrees. In some embodiments, φ is about 45 degrees.

In some embodiments, a retarder includes a plurality of retarder layers. Multiple retarder layers may be utilized to give a retardance in waves (e.g., the retardance in nm divided by the wavelength in nm) that is independent or only weakly dependent on wavelength. In some embodiments, for at least one wavelength in a range from 400 nm to 700 nm, the retarder has a retardance of one fourth of the wavelength. In some embodiments, the retarder has a retardance of one fourth the wavelength for one wavelength and in some embodiments, the retarder has a retardance of one fourth the wavelength for two or more wavelengths. In some embodiments, the retarder has a retardance different from quarter wave. For example, a retardance of $(n+\frac{1}{4})\lambda$ may be used.

Any retarder which allows the circular polarizer to function as a circular polarizer may be used. In some embodiments, a retarder includes a plurality of retarder layers where σ first retarder layer in the plurality of retarder layers has a first fast axis and a second retarder layer in the plurality of retarder layers has a second fast axis. In some embodiments, the first and second fast axes are parallel and in some embodiments, the first and second fast axes are not parallel. Non-parallel fast axes may be used in a retarder of a circular polarizer for improving the achromaticity of the circular polarizer. The angle between the fast axes of first and second retarder layers may be any suitable angle. In some embodiments, this angle is about 0 degrees (e.g., between −5 degrees and 5 degrees). In other embodiments, this angle is between 0 degrees and 45 degrees, or between 45 degrees and 90 degrees.

Further details on partial reflectors useful as a color-correction component are described in U.S. Prov. Appl. No. 62/566,654 (Haag et al.), for example.

In some embodiments, the color-correction component includes a color-correction film. In some embodiments, the color-correction film is disposed between the emissive display panel and a circular polarizer. In some embodiments, the color-correction film includes a plurality of microlayers where each microlayer has a maximum difference among its three orthogonal refractive indices at 550 nm less than or equal to 0.05. Each microlayer has an average refractive index being the arithmetic average of the three orthogonal refractive indices at 550 nm. In some embodiments, the plurality of microlayers are configured into layer pairs of alternating high and low index microlayers, where the average refractive index of each high index microlayer is between 0.15 and 0.75 more than the average refractive index of each low index microlayer. In some embodiments, the layer pairs each have optical thicknesses at 550 nm between 150 nm and 550 nm, and at least half of the layer pairs have optical thicknesses at 550 nm between 275 nm and 400 nm. In some embodiments, the color-correction film has few enough microlayers to transmit at least 80% of unpolarized visible light at normal incidence, photopically weighted, and the color-correction film has enough microlayers to reflect at least 15% of at least one wavelength of unpolarized light at 60 degrees incidence. A suitable photopic weighting function is the CIE (1931) photopic luminosity function $\bar{y}(\lambda)$ (also denoted $V(\lambda)$).

In some embodiments, the alternating layers are organic (e.g., organic polymer). In some embodiments, one of the alternating layers are organic and the other is inorganic. In other embodiments, both of the alternating layers are inorganic. In some embodiments, at least some of the plurality of microlayers of the color-correction film include both inorganic and organic materials. In some embodiments, at least some of the plurality of microlayers of the color-correction film include inorganic materials dispersed in an organic matrix. In some embodiments, the inorganic materials include metal oxides.

Layer-by-layer coatings, also known as polyelectrolyte multilayer (PEM) coatings or electrostatically self-assembled (ESA) coatings, are one class of coatings that can be used for the color-correction film. The plurality of microlayers, which may be disposed on a substrate, include at least one "bi-layer" deposited by what is commonly referred to as a "layer-by-layer self-assembly process". This process is commonly used to assemble thin films or coatings of oppositely charged polyions such as polyelectrolytes and/or inorganic oxide particles electrostatically, but other functionalities such as hydrogen bond donor/acceptors, metal ions/ligands, and covalent bonding moieties can be the driving force for film assembly. Typically, this deposition process involves exposing the substrate having a surface charge, to a series of liquid solutions, or baths. This can be accomplished by immersion of the substrate into liquid baths (also referred to as dip coating), spraying, spin coating, roll coating, inkjet printing, and the like. Exposure to the first polyion (e.g., polyelectrolyte bath) liquid solution, which has charge opposite that of the substrate, results in charged species near the substrate surface adsorbing quickly. This establishes a concentration gradient and draws more polyelectrolyte from the bulk solution to the surface. Further adsorption occurs until a sufficient microlayer has developed to mask the underlying charge and reverse the net charge of the substrate surface. In order for mass transfer and adsorption to occur, this exposure time is typically on the order of seconds to minutes. The substrate is then removed from the first polyion (e.g., bath) liquid solution, and is then exposed to a series of water rinse baths to remove any physically entangled or loosely bound polyelectrolyte. Following these rinse (e.g., bath) liquid solutions, the substrate is then exposed to a second polyion (e.g., polyelectrolyte or inorganic oxide nanoparticle bath) liquid solution, which has charge opposite that of the first polyion (e.g., bath) liquid solution. Once again adsorption occurs, since the surface charge of the substrate is opposite that of the second (e.g., bath) liquid solution. Continued exposure to the second polyion (e.g., bath) liquid solution then results in a reversal of the surface charge of the substrate. A subsequent rinsing can be performed to complete the cycle. This sequence of steps is said to build up one "bi-layer" of deposition and can be repeated as desired to add further bi-layers to the substrate. Multiple bi-layers are typically deposited to form one microlayer.

Some examples of suitable processes include those described in U.S. Pat. No. 8,234,998 (Krogman et al.); U.S. Pre-Grant Publication No. 2011/0064936 (Hammond-Cunningham et al.); and U.S. Pat. No. 8,313,798 (Nogueira et al.). Commercially available equipment for carrying out the layer-by-layer coating process include the STRATOSEQUENCE VI (nanoStrata Inc., Tallahassee, FL) dip coating robot and the SPALAS (Spray-Assisted Layer-by-Layer Assembly) coating system available from Agiltron, Inc. (Woburn, MA).

Thickness of layer-by-layer coatings on a substrate can be determined by common methods known in the art including, for example, stylus profilometry. Thickness and refractive index of layer-by-layer coatings can be determined by common methods known in the art including, for example, spectroscopic ellipsometry or reflectometry. Many layer-by-layer coatings exhibit a linear increase in thickness with the number of deposited bi-layers, while others exhibit exponential or super-linear growth. So-called "growth curves" (i.e., plots of thickness vs. number of bi-layers) are generally made for a given layer-by-layer material set (i.e., a polycation and a polyanion pair) under a specific set of conditions (e.g., concentration of the polyelectrolytes, ionic strength in the coating solutions, and pH of the coating solutions). For low index microlayers, the material set typically includes a polymeric polycation (e.g., polydiallyldimethylammonium chloride) and a low refractive index, anionic inorganic oxide nanoparticle (e.g., colloidal silicon dioxide). For high refractive index microlayers, the material set typically includes a polymeric polycation and a high refractive, anionic index inorganic oxide nanoparticles (e.g., colloidal zirconia or colloidal titania).

Inorganic silica sols in aqueous media are well known in the art and available commercially. Silica sols in water or water-alcohol solutions are available commercially under such trade names as LUDOX (manufactured by E.I. duPont de Nemours and Co., Inc., Wilmington, DE), NYACOL (available from Nyacol Co., Ashland, MA) or NALCO (manufactured by Nalco Chemical Co., Naperville, IL). Some useful silica sols are NALCO 1115, 2326, 1050, 2327, and 2329 available as silica sols with mean particle sizes of 4 nanometers (nm) to 77 nm. Another useful silica sol is NALCO 1034a available as a silica sol with mean particle size of 20 nanometers. A useful silica sol is NALCO 2326 available as a silica sol with mean particle size of 5 nanometers. Additional examples of suitable colloidal silicas are described in U.S. Pat. No. 5,126,394 (Revis et al.).

Various high refractive index inorganic oxide sols are commercially available. Zirconia sols are available from Nalco Chemical Co. (Naperville, IL) under the trade designation "Nalco 00SS008", Buhler AG (Uzwil, Switzerland) under the trade designation "Buhler zirconia Z-WO sol" and Nissan Chemical America Corporation (Houston, TX) under the trade name "NANOUSE ZR". A nanoparticle dispersion that includes a mixture of tin oxide and zirconia covered by antimony oxide (RI~1.9) is commercially available from Nissan Chemical America Corporation (Houston, TX) under the trade designation "HX-05M5". A tin oxide nanoparticle dispersion (RI~2.0) is commercially available from Nissan Chemicals Corp. under the trade designation "CX-S501M".

In some embodiments, the inorganic oxide nanoparticles include or are made from titania. Various forms of titania can be utilized including anatase, brookite, rutile and amorphous forms. Anatase titania nanoparticle (5-15 nm diameter) dispersions are commercially available from U.S. Research Nanomaterials (Houston, TX) as an aqueous suspension at 15 wt %. $TiO_2$ sols are also available dispersed in an acidic or basic solution from Ishihara Sangyo Kaisha Ltd. (Osaka, Japan). Titania has an isoelectric point at about pH 4-6 and thus can be used as a polyanion in layer-by-layer self-assembly at pH sufficiently above the isoelectric point, or the polycation in layer-by-layer self-assembly at pH sufficiently below the isoelectric point.

Suitable polyelectrolytes include polycationic polymers (i.e., polycations), such as polyallylamines or polyethylenimines. Suitable polycationic polymers include, for instance and without limitation, linear and branched poly(ethylenimine), poly(allylamine hydrochloride), polyvinylamine, chitosan, polyaniline, polyamidoamine, poly(vinylbenzyltriamethylamine), poly(diallyl-dimethyl ammonium chloride), poly(dimethylaminoethyl methacrylate), and poly(methacryloylamino)propyl-trimethylammonium chloride. Suitable polyanionic polymers include, but are not limited to, poly(vinyl sulfate), poly(vinyl sulfonate), poly(acrylic acid), poly(methacrylic acid), poly(styrene sulfonate), dextran sulfate, heparin, hyaluronic acid, carrageenan, carboxymethylcellulose, alginate, sulfonated tetrafluoroethylene based fluoropolymers such as NAFION, poly(vinylphosphoric acid), and poly(vinylphosphonic acid).

To match a target design for a color-correction film, growth curves are made for the high refractive index and low refractive index material sets typically on a glass substrate; other substrates such as silicon wafers or polymer film are also applicable. The growth curves allow for determination of the number of bi-layers required to reach a desired thickness. Color-correction coatings are then fabricated with the requisite number of bi-layers for each material set, and the UV/Vis/NIR reflection and/or transmission spectra are measured with a spectrophotometer. The spectra are then compared to the theoretical spectrum for the target design. If the spectra are not sufficiently close, then different numbers of bi-layers are deposited until the spectra are more closely matched. The actual thickness of the high and low index microlayers can be determined, for example, using cross-sectional scanning or transmission electron microscopy. Alternatively, optical modeling software can be used to determine the actual thickness of the microlayers. Often, non-idealities exist, such as different rates of coating growth affected by the substrate. Thus, the number of bi-layers may need to be altered accordingly to more closely match an optical design.

Vacuum deposited thin films are another class of coatings that may be used for the color-correction film. The alternating microlayers of high index microlayer (e.g., microlayer 2202 of FIG. 22, or the "A" layers of FIG. 23) and low index microlayer (e.g., microlayer 2204 of FIG. 22, or the "B" layers of FIG. 23) may be may be fabricated by conventional thin film vacuum deposition techniques for either polymer thin films, inorganic thin films or in hybrid combination of polymer and inorganic layers as described in U.S. Pat. No. 7,018,713 (Padiyath et al.). Depending on the type of polymer material, the films can be vapor deposited with different strategies. Direct vapor deposition can be applied for such polymers as polyethylene or polytetrafluoroethylene that have weak intermolecular interaction. In general, polymer thin films are obtained by a vapor-deposition polymerization method, which evaporates monomer materials and produces polymer thin films by polymerization reaction on the substrate surface. Co-evaporation of bifunctional monomers leads to stepwise reaction via polycondensation or polyaddition to obtain thin films of such polymers as polyimide and polyurea. This method can also be applied for preparing thin films of π-conjugated polymers. Another class of vapor-deposition polymerization utilizes chain-addition reaction to achieve radical polymerization of vinyl or acrylic monomers. This method has advantages in obtaining higher degrees of polymerization and in enabling versatile molecular design. A surface-initiated vapor-deposition polymerization, which combines the self-assembled monolayer (SAM) with vapor deposition of monomers, is a unique method to grow polymer thin films that are chemically bound to the substrate surface. The solvent-free nature of PVD is convenient for the formation of nanometer-thick films and multilayer films that are sometimes required for device fabrication.

Alternating microlayers of high index microlayer and low index microlayer may have a thickness that varies within the color-correction film. In some embodiments, the microlayers may be configured roughly from thinnest to thickest optical layer pair thickness (for example, with no more than two layer pair exceptions), or vice versa. In some embodiments, each layer pair optical thickness is different. In some embodiments, each layer optical thickness is the same. In some embodiments, with so few layers, it is necessary to maximize the breadth of reflected wavelengths by having each layer pair covering a different portion of the desired reflection band. In some embodiments, however, with so few layers, it is necessary to maximize the intensity of a certain reflected wavelength by having more than one layer pair for a given wavelength or having more than one layer pair within 10 nm of each other. In some embodiments, each of the layer pairs each have optical thicknesses at 550 nm between 150 nm and 550 nm. In some embodiments, at least half of the layer pairs have optical thicknesses at 550 nm between 275 and 400 nm. In some embodiments, at least half the layer pairs have optical thicknesses that correspond to a reflection band centered on yellow, orange, or red light. The exact tuning and configuration of the layer thicknesses that is desired may depend on the configuration on the rest of the display and the particularities of the emissive display's white point.

Because the color-correction film enhances color fidelity with shifting angle based on reflection or absorption, there is a tradeoff between the magnitude of those properties and transmission. In some embodiments, it may be desirable to keep the transmission high. In some embodiments, the color-correction film has few enough layers to transmit at least 80% of unpolarized visible light at normal incidence. In some embodiments, the color-correction film has few enough layers to transmit at least 85% of unpolarized visible light at normal incidence. In some embodiments, the color-correction film has few enough layers to transmit at least 90% of unpolarized visible light at normal incidence. The percentage of transmission here refers to the photopically weighted transmission average. Conversely, in some embodiments, in order to be effective at correcting color shift, the reflection or absorption of at least one wavelength of unpolarized light at 60 degree incidence should be at least 10%. In some embodiments, the reflection or absorption of at least one wavelength of unpolarized light at 60 degree incidence should be at least 15%. In some embodiments, the reflection or absorption of at least one wavelength of unpolarized light at 60% incidence should be at least 20%. In some embodiments, the color-correction film has between 6 and 26 optical layers, inclusive. In some embodiments, the color-correction film has between 8 and 20 microlayers, inclusive.

In some embodiments, the thickness of the plurality of microlayers of the color-correction film is less than 3 micrometers. In some embodiments, the thickness of the plurality of microlayers of the color-correction film is less than 1 micrometer. In some embodiments, the thickness of the plurality of microlayers of the color-correction film is between 1.5 and 2.5 micrometers.

In some embodiments, the color-correction film appears cyan in transmission at normal incidence. In some embodiments, the color-correction film appears magenta in transmission at 60 degrees incidence.

Further details on color-correction films useful as color-correction components are described in U.S. Prov. Pat. Appl. No. 62/383,058 (Benoit et al.), for example.

In some embodiments, the color-correction component is or includes a diffuser film. It has been found that certain diffuser films when placed proximate an OLED display panel reduce the color shift of the OLED display panel. In some embodiments, the diffuser film is a polymeric film including a polymeric layer including interconnected pores and channels. In some embodiments, the diffuser film is a polymeric film including a polymeric layer that is void free and that includes particles uniformly dispersed in a polymeric matrix.

In some embodiments, the color-correction component is or includes a polymeric film where the polymeric film includes a first polymeric layer having two major surfaces. In some embodiments, the first polymeric layer includes a first polymer region including a first material having a refractive index of n1; and a second region including a network of interconnected pores and channels within the first polymer region, the channels including a second material having a refractive index of n2. In some embodiments, the first material includes a first elastic polymeric material and optional particles. In some embodiments, the second material includes a second polymeric material and optional particles; and/or air. In some embodiments, the polymeric film has a clarity of at least 70%, or at least 80%, or at least 90%, a visible light transmission of at least 80%; and a bulk haze of 25% to 80%. In some embodiments, the polymeric film has a normalized micro-haze non-uniformity of not more than 12% across the polymeric film.

The term "haze" refers to wide angle light scattering, where light emitting from a display is diffused in all directions causing a loss of contrast. More particularly, the term "bulk haze" refers to the wide-angle light scatter measured with a broad sampling beam of several millimeters (mm) so as to give an average result from said several-millimeter aperture of the polymeric film. Also, more particularly, the term "micro-haze" refers to wide angle light scattering as measured by a smaller illuminated area of tens of microns (i.e., less than 100 microns, e.g., 10 to 40 microns) such that the average micro-haze measurement represents the average result from many measurements, each tens of microns in area, extending over several millimeters of the polymeric film.

The term "normalized micro-haze non-uniformity" refers to the ratio of the standard deviation of the micro-haze to the average value of micro-haze when measured over at least 1 mm, and typically over several millimeters. The standard deviation of micro-haze is a measure of micro-haze noise. As such, normalized micro-haze non-uniformity is a metric for the ratio of visual micro-haze noise to micro-haze signal.

The term "clarity" refers to narrow angle scattering, where light is diffused in a small angle range with high concentration. The effect of having a certain clarity basically describes how well very small details can be seen through a specimen.

Haze, clarity and visible light transmission can be determined as described in the ASTM D1003-13 test standard.

The first material includes a first elastic polymeric material and optional particles. The first material forms a porous structure with a network of interconnected pores (i.e., voids) and channels. That is, the pores and channels are defined by the first polymer region.

Typically, the plurality of interconnected pores and channels includes pores connected to one another via hollow tunnels or tunnel-like passages. In certain embodiments, in a network there can be multiple pluralities of interconnected pores and channels. In certain embodiments, there can be minor amounts of closed or unconnected pores.

Typically, the pores and channels have an average cross-section (e.g., diameter for spherical pores) of no greater than 2 micrometers. Alternatively stated, the network of interconnected pores and channels possess angular-averaged scattering properties that are similar to a scattering particle of less than 2 micrometers in size. The term angular-averaged scattering property has the following significance: The scattering centers of irregular shapes have scattering properties such as scattering cross section and scattering angle which are highly dependent of the impinging light angle. The angular-averaged scattering property takes the impinging light angle into account, and presents the averaged property of all the impinging light angles.

In certain embodiments, a volume fraction of the plurality of interconnected pores and channels is at least 10%.

The first polymeric material is typically a cured product of multifunctional monomers and/or oligomers. In certain embodiments, the first polymeric material includes an organic polymer selected from the group of an acrylate, a polyolefin, a polyurethane, a silicone, a polyester, and a combination thereof. In certain embodiments, the first polymeric material includes a cured product of multifunctional (meth)acrylate monomers and/or oligomers (where (meth)acrylate includes methacrylates and acrylates).

The polymeric material is preferably sufficiently elastic to support the porous structure such that the pores and channels do not collapse. In this context, a "elastic" material may be a soft or hard elastic material, but not a viscous or viscoelastic material that would slowly fill in the porous structure due to material flow.

Examples of multifunctional monomers that can form the first polymeric material include trimethylolpropane triacrylate (commercially available from Sartomer Company, Exton, PA under the trade designation SR351), ethoxylated trimethylolpropane triacrylate (commercially available from Sartomer under the trade designation SR454), pentaerythritol tetraacrylate, pentaerythritol triacrylate (commercially available from Sartomer under the trade designation SR444), dipentaerythritol pentaacrylate (commercially available from Sartomer under the trade designation SR399), ethoxylated pentaerythritol tetraacrylate, ethoxylated pentaerythritol triacrylate (from Sartomer under the trade designation SR494), dipentaerythritol hexaacrylate, and tris(2-hydroxyethyl)isocyanurate triacrylate (from Sartomer under the trade designation SR368), 1,6-hexanediol diacrylate (from Sartomer under trade name of SR238), and (meth)acrylate functionalized oligomers. Examples of such oligomers include those resins with high tensile strength and high elongation, for example, CN9893, CN902, CN9001, CN961, and CN964 that are commercially available from Sartomer Company; and EBECRYL 4833 and Eb8804 that are commercially available from Cytec Industries, Woodland Park, NJ). Suitable materials also include combinations of "hard" oligomeric acrylates and "soft" oligomeric acrylates. Examples of "hard" acrylates include polyurethane acrylates such as EBECRYL 4866, polyester acrylates such as EBECRYL 838, and epoxy acrylates such as EBECRYL 600, EBECRYL 3200, and EBECRYL 1608 (commercially available from Cytec); and CN2920, CN2261, and CN9013 (commercially available from Sartomer Company). Examples of the "soft" acrylates include EBECRYL 8411 that is commercially available from Cytec; and CN959, CN9782, and CN973 that are commercially available from Sartomer Company. Suitable materials are described, for example, in U.S. Pat. No. 9,541,701 B2 (Thompson et al).

In certain embodiments, the first material also includes particles to help control morphology. In certain embodiments, the particles are nanoparticles, optionally surface-modified nanoparticles. Examples of such particles include $SiO_2$ (e.g., A174-treated NALCO 2329K silica particles, surface-modified MP4540M silica particles from Nissan Chemical America), $ZrO_2$, $TiO_2$, $SnO_2$, and combinations thereof. Preferred particles are $SiO_2$. Examples of such particles are described, for example, in U.S. Pat. Appl. Publ. No. 2012/0038990 A1 (Hao et al). The amount of particles in the first material can be up to 60 wt-%, based on the total weight of the first material.

The preparation of the porous structure defined by the first polymeric material is described, for example, in U.S. Pat. Appl. Publ. No. 2012/0038990 A1 (Hao et al.) and U.S. Pat. No. 8,808,811 B2 (Kolb et al). In one process, first a solution is prepared that includes a polymerizable material dissolved in a solvent, where the polymerizable material can include, for example, one or more types of monomers, optionally additives such as coupling agents, crosslinkers, and initiators, and optionally a plurality of particles, such as nanoparticles. Next, the polymerizable material is polymerized, for example, by applying heat or light, to form an insoluble polymer matrix in the solvent. In some cases, after the polymerization step, the solvent may still include some of the polymerizable material, although at a lower concentration. Next, the solvent is removed by drying or evaporating the solution resulting in a first polymeric matrix that includes a network of interconnected channels dispersed in the polymer binder. Optionally, the first polymeric matrix includes a plurality of particles dispersed in the first polymeric matrix. If used, the particles are bound within the first polymeric matrix, where the bonding can be physical or chemical.

In certain embodiments, the first material is present in the first polymeric layer in an amount of at least 35 vol-%, based on the total volume of the polymeric film. In certain embodiments, the first material is present in the first polymeric layer in an amount of up to 90 vol-%, based on the total volume of the polymeric film.

The polymeric film of present description can be made utilizing a network of pores and channels within the first material as the "host" that is completely or even partially filled with the second material. The second material has a mismatched refractive index with that of the first material. Typically, the difference of refractive index between the first and second materials is at least 0.01. With completely filling of the pores and channels with a polymeric material, the original "air voids" will be displaced by the "guest" polymeric phase in the first polymeric "host" phase. The optical properties of the resulting polymeric film of present description can be determined by the difference of refractive index between the first ($n_1$) and second ($n_2$) polymeric materials and the unique morphology of those two intermixed materials.

In certain embodiments, the network of pores and channels is filled with air. In certain embodiments, the network of pores and channels is filled with a second polymeric material and optionally particles. In certain embodiments, the network of pores and channels is filled with a mixture of air and a second polymeric material (optionally mixed with particles). The air, the second polymeric material (optionally mixed with particles), or a mixture thereof, are referred to herein as the second material, and the plurality of interconnected pores and channels that is filled with the second material is referred to herein as the second interconnected region.

Thus, herein the first material defines a first polymer region including a first material having a refractive index of $n_1$. A second interconnected region including a second material having a refractive index of $n_2$ forms an interpenetrating network within the first material.

If the second material includes a polymeric material, the second polymeric material includes an organic polymer selected from the group of an acrylate, a polyolefin, a polyurethane, a silicone, a polyester, and a combination thereof. Particles may also be mixed with the second polymeric material to control the refractive index. In certain embodiments, the particles are nanoparticles, optionally surface-modified nanoparticles. Examples of such particles include $TiO_2$, $ZrO_2$, $SnO_2$, as well as some mixed metal oxides such as HX-305M5, a mixture of $SnO_2/ZrO_2/SbO_2$, manufactured by Nissan Chemical America, Houston, TX Examples of such particles are described, for example, in U.S. Pat. No. 8,343,622 (Liu et al). The amount of particles in the second material can be up to 80 vol-%, based on the total volume of the second material.

If the second material includes a polymeric material, such polymeric material is typically present in the polymeric film in an amount of at least 10 vol-%, based on the total volume of the polymeric film. If the second material includes a polymeric material, such polymeric material is typically present in the polymeric film in an amount of up to 65 vol-%, based on the total volume of the polymeric film.

The first material (of the first polymer region) has a refractive index of $n_1$. The second material (of the second interconnected region) has a refractive index of $n_2$. The materials of these regions are selected such that $n_1$ is different than $n_2$. In certain embodiments, $|n_1-n_2|$ is at least 0.01. In certain embodiments, $|n_1-n_2|$ is at least 0.02, or at least 0.03, or at least 0.04, or at least 0.05, or at least 0.1. In certain embodiments, $|n_1-n_2|n_1$ is at most 0.5. In certain embodiments, $n_1$ is within 0.5 of $n_2$, $n_1$ is within 0.4 of $n_2$, $n_1$ is within 0.3 of $n_2$, $n_1$ is within 0.2 of $n_2$, or $n_1$ is within 0.1 of $n_2$. In this context, "within" means within 0.5 (or 0.4, or 0.3, or 0.2, or 0.1) higher or lower.

In certain embodiments, the first polymeric layer is the only polymeric layer of the polymeric film of the present description. In certain embodiments, the first polymeric layer is one of two or more polymeric layers of the polymeric film of the present description. In certain embodiments, the first polymeric layer is one of two polymeric layers of the polymeric film of the present description.

Figure 29:
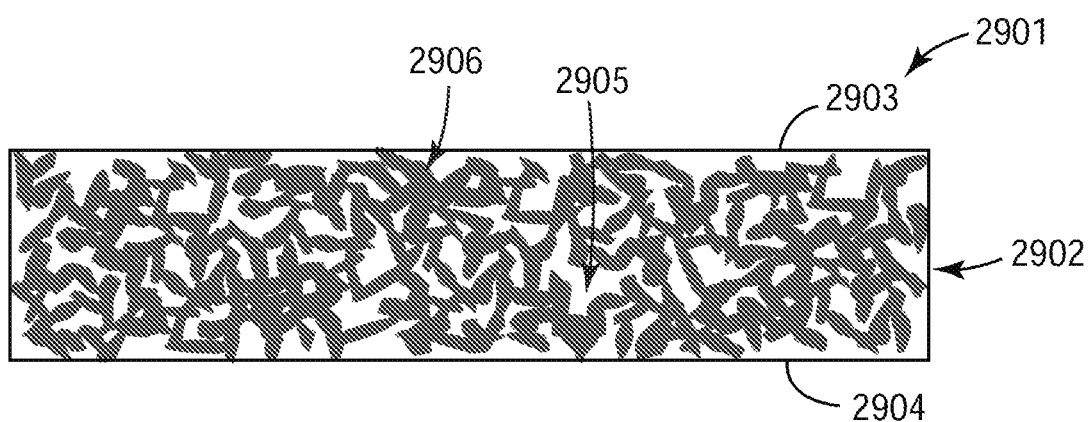
FIG. 29 is a schematic cross-sectional representation of a polymeric film.

As shown in FIG. 29, in certain embodiments, polymeric film 2901 includes a polymeric layer 2902 having two major surfaces 2903 and 2904, where the polymeric layer 2902 includes a first polymer region 2905 including a first material having a refractive index of $n_1$; a second region including a network of interconnected pores and channels 2906 within the first polymer region 2905, which is filled with a second material having a refractive index of $n_2$. The second material within the interconnected pores and channels 2906 may be air, a polymeric material, or a combination thereof.

In certain embodiments, the polymeric film of the present description includes a second polymeric layer disposed on one or both major surface(s) of the first polymeric layer; where the second polymeric layer includes a third polymeric material having a refractive index $n_3$; where the first polymeric material and the third polymeric material are the same or different.

Figure 30:
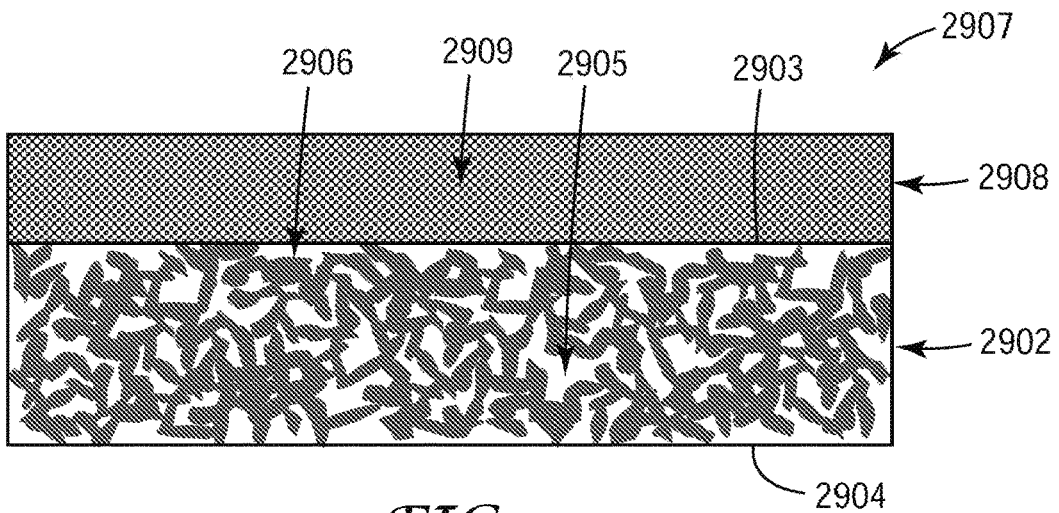
FIG. 30 is a schematic cross-sectional representation of the polymeric film of FIG. 29 with an additional polymeric layer.

As shown in FIG. 30, in certain embodiments, polymeric film 2907 of the present description includes a second polymeric layer 2908 disposed on one major surface 2903 of the first polymeric layer 2902, which includes first polymer region 2905. The second polymeric layer 2908 includes a third polymeric material. The first polymeric material (of region 2905) and the third polymeric material (of layer 2908) may be the same or different. Alternatively, the third polymeric material (or layer 2908) may be the same as the second polymeric material within the network of interconnected pores and channels 2906.

If the second material includes air, the intermixing network of the first and second materials forms a porous structure. The second polymeric layer 2908 (FIG. 30) forms a capping layer, where the third polymeric material of the capping layer is not penetrated into or only partially penetrated into a portion of the porous structure. In certain embodiments, the third polymeric material includes an organic polymer selected from the group of an acrylate, a polyolefin, a polyurethane, a silicone, a polyester, and a combination thereof.

In certain embodiments the first and third polymeric materials are different such that $n_1$ is different than $n_3$. In certain embodiments, $|n_1-n_3|n_1$ is at least 0.05. In certain embodiments, $|n_1-n_3|$ is at most 0.5. In certain embodiments, $n_1$ is within 0.5 of $n_3$, $n_1$ is within 0.4 of $n_3$, $n_1$ is within 0.3 of $n_3$, $n_1$ is within 0.2 of $n_3$, or $n_1$ is within 0.1 of $n_3$. In this context "within" means within 0.5 (or 0.4, or 0.3, or 0.2, or 0.1) higher or lower.

In certain embodiments, at least one of the second or third polymeric materials is an adhesive material. In certain embodiments, each of the second and third polymeric materials is an adhesive material.

In certain embodiments, the first (possibly only) polymeric material of the polymeric film has a thickness of at least 500 nanometers micrometers (micrometers or μm). In certain embodiments, the first (possibly only) polymeric layer of the polymeric film has a thickness of up to up to 25 micrometers, or up to 15 micrometers, or up to 5 micrometers, or up to 1 micrometers.

In certain embodiments, the second polymeric material can fill partially the pores and channels within the first material, or completely fill the pores and channels within the first material and optionally have excess second polymeric layer on top of the filled intermixing layer (layer 2902, FIG. 30). There is no maximum thickness to this excess second polymeric layer (e.g., layer 2908, FIG. 30), although, in certain embodiments, it may be up to 1 millimeter (mm) thick.

In certain embodiments, the overall polymeric film has a thickness of at least 1 micrometer. In certain embodiments, the overall polymeric film has a thickness of up to 15 micrometers, up to 25 micrometers, up to 50 micrometers, or even over 100 micrometers.

A polymeric film used in a color-correction component of the present description may have the following characteristics: a clarity of at least 70% (preferably at least 80 percent, or preferably at least 85%, or more preferably at least 90%); a visible light transmission of at least 85% (preferably at least 90%); a bulk haze of 15% to 80% (preferably 20% to 80%, more preferably 30% to 70%, and even more preferably 30% to 50%). In certain embodiments, a polymeric film of the present description has a normalized micro-haze non-uniformity of not more than 12% (preferably less than 10%, or more preferably less than 8%) across the polymeric film. Such films can function as very moderate optical diffusers with controlled local uniformity when used in a OLED device. The clarity, transmission, and bulk haze can be measured using a Haze Gard Plus (from BYK Gardner, Columbia, MD), which reports measurements from a sampling beam of 18 millimeters (mm) aperture of the polymeric film. The preferred clarity, transmission and haze ranges may differ for the displays of the present description from the corresponding preferred ranges when used in conventional displays due to the differing design space for display panels used in the present description.

In some embodiments, a color-correction component is or includes a polymeric film including a polymeric layer having two major surfaces, where the polymeric layer includes a polymeric matrix and particles (preferably, polymeric particles) and is preferably void free. The polymeric layer having particles is referred to as the first polymeric layer. The first polymeric layer includes: a first polymeric matrix having a refractive index n1; and particles having a refractive index n2 uniformly dispersed within the first polymeric matrix; where the particles are present in an amount of less than 30 vol-%, based on the volume of the first polymeric layer, and have a particle size range of 400 nanometers (nm) to 3000 nm; and where n1 is different than n2. Such a polymeric film has the optical function of a very moderate optical diffuser.

In certain embodiments, the first polymeric layer is the only polymeric layer of the polymeric film of the present description. In certain embodiments, the first polymeric layer is one of two polymeric layers of the polymeric film of the present description. In certain embodiments, the first polymeric layer is one of two or more polymeric layers of the polymeric film of the present description.

Figure 31:
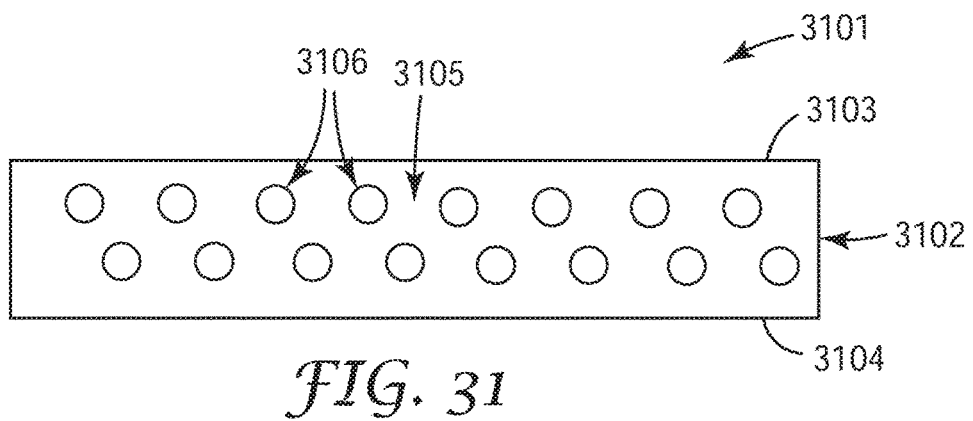
FIG. 31 is a schematic cross-sectional representation of a single-layer polymeric film.

As shown in FIG. 31, in certain embodiments, polymeric film 3101 includes a polymeric layer 3102 having two major surfaces 3103 and 3104, where the polymeric layer 3102 includes a polymeric matrix 3105 and particles 3106 (preferably, polymeric particles) uniformly dispersed within this first polymeric matrix 5. In certain embodiments, such polymeric film 3101 is void-free. In this context, "void-free" means that there is less than 0.5 volume percent (vol-%) pores or voids.

Figure 32:
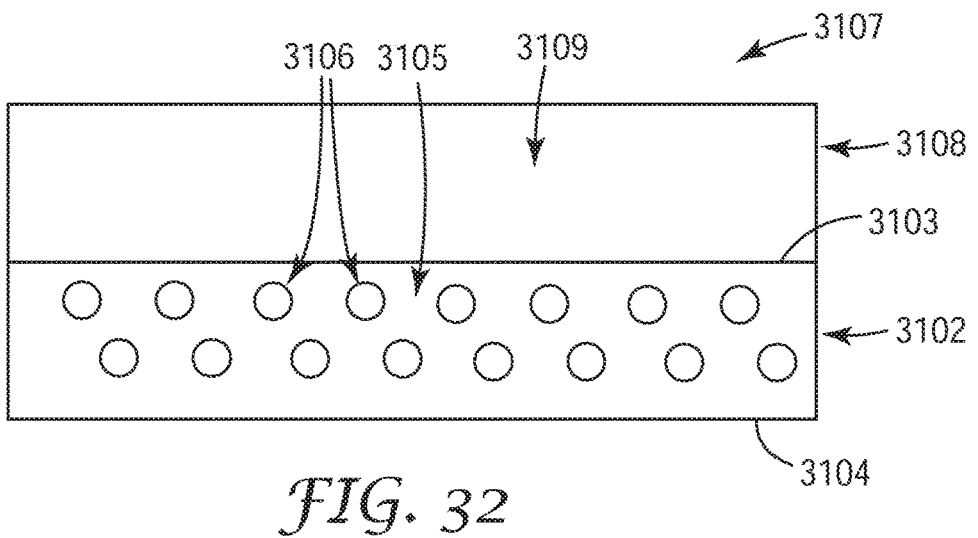
FIG. 32 is a cross-sectional representation of a dual-layer polymeric film.

As shown in FIG. 32, in certain embodiments, polymeric film 3107 of the present description includes a second polymeric layer 3108 disposed on one major surface 3103 of the first polymeric layer 3102, which includes polymeric matrix 3105 (i.e., first polymeric matrix 3105) and particles 3106. The second polymeric layer 3108 includes a second polymeric matrix 3109. The first polymeric matrix 3105 and the second polymeric matrix 3109 may be the same or different.

The first polymeric matrix (the matrix in which the particles are dispersed) has a refractive index $n_1$, and the second polymeric matrix has a refractive index n3. In certain embodiments, the first polymeric matrix and the second polymeric matrix include the same material. In certain embodiments, the first polymeric matrix is different than the second polymeric matrix.

In certain embodiments, if the first and second polymeric matrices are different, n1 is at least 0.05 different than n3. In certain embodiments, n1 is within 0.2 of n3, and in certain embodiments, n1 is within 0.1 of n3. In this context "within" means within 0.2 (or 0.1) higher or lower.

In certain embodiments, at least one of the first polymeric matrix and the second polymeric matrix is an adhesive matrix. In certain embodiments, the first polymeric matrix and the second polymeric matrix each is or includes an adhesive matrix. In certain embodiments, the first adhesive matrix and the second adhesive matrix include the same material. In certain embodiments, the first adhesive matrix is different than the second adhesive matrix.

In certain embodiments, the first (possibly only) polymeric layer of the polymeric film has a thickness of at least 10 micrometers (micrometers or µm). In certain embodiments, the first (possibly only) polymeric layer of the polymeric film has a thickness of up to 100 micrometers, or up to 50 micrometers, or up to 25 micrometers, or up to 15 micrometers.

In certain embodiments, the second polymeric layer of the polymeric film has a thickness of at least 25 micrometers. There is no maximum thickness to this second polymeric layer, although, in certain embodiments, it may be up to 1 millimeter (mm) thick.

In certain embodiments, the overall polymeric film has a thickness of at least 35 micrometers. In certain embodiments, the overall polymeric film has a thickness of up to 130 micrometers.

A polymeric film used in a color-correction component of the present description may have the following characteristics: a clarity of at least 70% (preferably at least 80%, or preferably at least 85%, or more preferably at least 90%); a visible light transmission of at least 85% (preferably at least 90%); a bulk haze of 15% to 80% (preferably 20% to 80%, more preferably 30% to 70%, and even more preferably 30% to 50%); and a normalized micro-haze non-uniformity of not more than 12% (preferably less than 10%, or more preferably less than 8%) across the polymeric film. The preferred clarity, transmission and haze ranges may differ for the displays of the present description from the corresponding preferred ranges when used in conventional displays due to the differing design space for display panels used in the present description.

Uniformity of the controlled haze (e.g., of the polymeric film of any of FIGS. 29-32) for spatial distributions on the order of the length scale of the display pixels is typically preferred so that a desired visually perceived quality of a pixelated display can be achieved. Non-uniformity of the haze above the order of length scale of the display pixels can lead to optical defects such as pixel blur or so-called sparkle. This quality is measurable by means of a micro-haze uniformity measurement, which provides measurements from a sampling beam illuminating a few tens of micrometers of the sample. In this measurement, the polymeric film surface is scanned with an optical probe that has sub-pixel dimensions while measuring standard deviation in the measured micro-haze levels. This micro-haze measurement technique allows sample analysis for spatial frequencies corresponding to the peak for human vision perception—namely, spatial frequencies in the range of 1-5 line pairs per millimeter for typical viewing distances. The micro-haze measurements allow the examination of size scale variations on the size scale for display pixel dimensions. In contrast, conventional haze measurement systems analyze a large area of the optical film for each measurement and are unable to distinguish visually perceived differences on the critical length scales for pixelated displays.

Significantly, the polymeric films control light diffusion and significantly improve angular color uniformity of OLED displays by controlling the differences in refractive indices between the particles and the polymeric matrix, the size and loading of the particles, the thickness of the polymeric films, and the distance between the first polymeric layer of the polymeric film and display. The larger the distance between the first polymeric layer of the polymeric film and the emissive display plane, the more undesirable pixel blur increases. The smaller the pixel size, the closer the first polymeric layer of the polymeric film and display plane should be. Also, as this distance increases, the contrast ratio becomes undesirably low. Because of these two factors, the distance between the first polymeric layer of the polymeric film and emissive display plane is desirably minimized. For one example, for commercially available handheld devices having typical pixel spacing of 50 micrometers, the distance between the first polymeric layer of the polymeric film and emissive display plane distance should preferably be less than 150 micrometers. For an additional example, large display monitors having typical pixel spacing of 500 micrometers, the distance between the first polymeric layer of the polymeric film and emissive display plane should preferably be less than 1500 micrometers. In general, the distance between the first polymeric layer of the polymeric film and emissive display plane is desirably less than 3 times the pixel spacing dimension of the display. Smaller first polymeric layer to display plane distances are even more preferable. In some embodiments, the distance between the first polymeric layer of the polymeric film and the emissive display plane is desirably less than 2 times the pixel spacing dimension of the display. In other embodiments, the distance between the first polymeric layer of the polymeric film and emissive display plane is desirably less than the pixel spacing dimension for the display. In preferred embodiments, the polymeric films do not significantly affect major performance characteristics, including brightness, circular polarizer compatibility, and view angle. Also, importantly, the pixel blur can be significantly reduced.

A wide variety of polymers may be used in the polymeric materials of the polymeric films of the present description. Exemplary polymers for use in the polymeric materials include silicones, acrylates, polyurethanes, polyesters, and polyolefins.

In certain embodiments, the polymeric materials can be selected from a single-phase polymer or a polymer having a multiphase morphology. The multiphase morphology may be inherent in the choice of polymer matrix, such as for example, in a semi-crystalline polymer having both amorphous and crystalline domains, or may result from a polymer blend. Alternatively, the multiphase morphology may develop during drying or curing of the polymer matrix. Useful polymer matrices having multiphase morphology include those where each of the phases has the same refractive index or those where the refractive index is mismatched but the domain size of the dispersed phase does not exceed the size of the particles dispersed in the polymer matrix.

In certain embodiments, the polymeric materials are adhesive materials. In certain embodiments, at least one adhesive material includes an optically clear adhesive (OCA). In certain embodiments, the optically clear adhesive is selected from an acrylate, a polyurethane, a polyolefin (such as a polyisobutylene (PIB)), a silicone, or a combination thereof. Illustrative OCAs include those described in International Pub. No. WO 2008/128073 (3M Innovative Property Co.) relating to antistatic optically clear pressure sensitive adhesives and WO 2009/089137 (Sherman et al.) relating to stretch releasing OCA, U.S. Pat. App. Pub. Nos. US 2009/0087629 (Everaerts et al.) relating to indium tin oxide compatible OCA, US 2010/0028564 (Cheng et al.) relating to antistatic optical constructions having optically transmissive adhesive, US 2010/0040842 (Everaerts et al.) relating to adhesives compatible with corrosion sensitive layers, US 2011/0126968 (Dolezal et al.) relating to optically clear stretch release adhesive tape, and U.S. Pat. No. 8,557,378 (Yamanaka et al.) relating to stretch release adhesive tapes. Suitable OCAs include acrylic optically clear pressure sensitive adhesives such as, for example, 3M OCA 8146 available from 3M Company, St. Paul, MN.

In certain embodiments, a dual layer product construction (see, e.g., FIGS. 30 and 32) may include one layer (e.g., layer 2902 in FIG. 30 or layer 3102 in FIG. 32) having particular optically diffusing properties and a second layer (e.g., layer 2908 in FIG. 30 or layer 3108 in FIG. 32) being an optically clear adhesive. Some of the benefits for forming a dual layer product construction would be to provide improved adhesive properties such as peel strength, robustness, coating integrity, etc. In cases where the dual layer product is incorporated into an OLED display device, the optically diffuse layer e.g., layer 2902 in FIG. 30 or layer 3102 in FIG. 32) is preferably facing an OLED emissive display plane and placed as close to that plane as the construction allows. For best performance, including contrast ratio and minimization of pixel blur, etc., the optically diffuse layer would be preferably in direct contact with an OLED encapsulation layer(s). If not in direct contact, the performance may be degraded as the distance between the diffuse layer and emissive plane increases.

In embodiments where the color-correction component includes a polymeric film including particles in a polymeric matrix, the particles, such as polymeric particles, are preferably uniformly dispersed within the polymeric matrix. In this context, "uniformly dispersed" means a continuous randomly dispersed particle distribution throughout a polymeric matrix. Such dispersed particles are dispersed individual particles, not aggregates or aggregations of particles. The presence of such aggregates creates highly localized haze differences that show up in a lit display as a defect known in the industry as sparkle. Unlike typical bulk diffusers that are often positioned on the backside of the display panel, such as an LCD, the color-correcting diffuser film is placed between the display panel and the viewer, making defects due to particle aggregation more obvious. In addition, for wide view color applications a high clarity of the optical film is often desired. Such clarity would also make particle agglomerates more apparent, in contrast with typical diffusers which are commonly higher in haze and lower in clarity.

In order to get uniformly dispersed particles in a polymer matrix, mixing processes and coating methods need to be controlled. For example, to effectively disperse particles in a polymer precursor (for example, curable monomers) or a polymer composition, mechanical mixing may be carried out for a period of time on the order of minutes. Alternatively, rolling of samples (dry particles added to polymer precursor or solution) may be carried out, although to get complete and homogenous particle dispersion this may have to be done for extensive periods of time (e.g., on the order of days or weeks). Thus, roller mixing is not very practical or effective, and mechanical mixing is preferred because of its efficiency and high shearing capability, which helps break up any particle agglomerates that may be present during the initial mixing.

In addition to mechanical mixing, controlled (slow) addition of the particles to the components being mechanically mixed is typically necessary to avoid agglomeration of the individual particles. Rapid addition of particles can easily form a "wet-cake-like solid" that is difficult to redisperse once formed. Slow addition can involve adding small volumes (i.e., small shots) of particles so the mixer does not get overwhelmed and a cake is not formed. Once a small shot of particles is mixed in, another shot is added. Once a cake forms, it can be difficult to break it up and get a completely uniform dispersion in a reasonable amount of time.

Thus, in certain embodiments, to effectively uniformly disperse particles in a polymer matrix, a high shear mixer (e.g., disperser disk DSFB635, manufactured by Promix, Ontario, Canada) in combination with slow addition of the particles is preferred. Typically, for the more robust polymer or inorganic beads, high shear can be used, while for softer or more fragile particles, lower but longer shear exposure is recommended.

In contrast to the methods used in International Publication No. WO 2010/033558 (which typically involved dumping particles in a syrup and mixing on a roller mixer for only a few hours because dispersion uniformity was not necessary for the desired application, e.g., backside diffuser for an LCD), mechanically stirring (i.e., mechanically mixing) can significantly reduce particle aggregations in solution, resulting in a uniform dispersion of particles in a coated polymer matrix. In addition, sufficient mixing time can be used to break up particle aggregations in solution, if it occurs. Furthermore, to avoid particle settling and/or agglomeration, polymer/particle mixtures are continuously mixed, at least on a roller, until they are coated onto a substrate. In-line mixing during the coating process can be advantageously used, provided the shear/mixing time is sufficient to uniformly disperse the particles in the coating composition. In-line mixers such as those available from Quadro (Waterloo, Ontario, Canada) may be useful.

To retain uniformly dispersed particles in the final polymeric film, it is also preferred that a coating composition is coated through a precision coating method, such as slot die coating, where σ relatively large gap between the die and carrier film is preferred. For example, the addition of an optical clear adhesive layer that is not optically functional (diffusive) can open more gap between the die and carrier film, as a result, providing uniformly dispersed samples. Coating methods where dispersed particles may hang-up or dry on the coating knife or die may cause issues with particle agglomeration and are generally not preferred.

The particles have a particle size range of 400 nanometers (nm) to 3000 nm, or a particle size range of 700 nm to 2.0 micrometers (micrometers). In this context, "particle size" refers to the longest dimension of a particle, which is the diameter of a spherical particle. A "particle size range" refers to a distribution of particle sizes from the smallest to the largest (not an average). Thus, the particles are not necessarily uniform in size. The particle size can be determined by scanning electron microscopy (SEM).

The particles may be of a variety of shapes, including polyhedron, parallelepiped, diamond, cylinder, arcuate, arcuate cylinder, rounded (e.g., oval or spherical or equiaxial), hemisphere, gumdrop, bell, cone, frusto conical cone, irregular, and mixtures thereof. In certain embodiments, the particles are spherical beads.

The polymeric film of the present description may include a first polymeric layer having two major surfaces, where the first polymeric layer includes a first polymeric matrix and particles (preferably, polymeric particles) uniformly dispersed therein. The particles have a refractive index n2 and the first polymeric matrix in which the particles are dispersed have a refractive index n1, where n1 is different than n2. In certain embodiments, |n1−n2| is at least 0.01. In certain embodiments, |n1−n2| is at least 0.02, or at least 0.03, or at least 0.04, or at least 0.05. In certain embodiments, |n1−n2| is at most 0.5. In certain embodiments, n1 is within 0.5 of n2, n1 is within 0.4 of n2, n1 is within 0.3 of n2, n1 is within 0.2 of n2, or n1 is within 0.1 of n2. In this context "within" means within 0.5 (or 0.4, or 0.3, or 0.2, or 0.1) higher or lower.

Particles are preferably organic polymeric particles, but other particles may be used as well. Exemplary non-organic particles include $SiO_2$, $Al_2O_3$, $ZrO_2$, ZnO, and mixtures thereof. Exemplary organic polymers for use in the organic particles include an organic polymeric material selected from a silicone, such as a polydimethylsiloxane (PDMS), a polyurethane, a polymethyl methacrylate (PMMA), a polystyrene, or a combination thereof.

In certain embodiments, the particles are present in the first polymeric layer in an amount of less than 30 percent by volume (vol-%), based on the volume of the first polymeric layer. In certain embodiments, the particles are present in the first polymeric matrix in an amount of up to 25 vol-%, up to 20 vol-%, or up to 15 vol-%, based on the total volume of the first polymeric layer. In certain embodiments, the particles are present in the first polymeric matrix in an amount of at least 0.5 vol-% (or at least 1 vol-%), based on the total volume of the first polymeric layer.

Further details on polymeric films useful as color-correction components are described in U.S. patent application Ser. No. 15/587,929 (Hao et al.) and Ser. No. 15/587,984 (Hao et al.), for example.

The following is a list of illustrative embodiments of the present description.

Embodiment 1 is a method of making an organic light emitting diode (OLED) display, the method including:

providing an OLED display panel such that each comparative display panel in a plurality of comparative display panels otherwise equivalent to the OLED display panel except for one or more values of a plurality of design parameters has a maximum white-point color shift as a view angle varies from 0 to 45 degrees of $WPCS^C_{45}$ and a white-point axial efficiency of $WPAE^C$, the plurality of comparative display panels defining a performance curve along a boundary of performance points in $WPCS^C_{45}$–$WPAE^C$ space, the performance curve extending from a first endpoint having a lowest acceptable efficiency to a second endpoint having a largest acceptable white-point color shift $WPCS_{45}^{LA}$, the providing step including selecting the plurality of design parameters such that the OLED display panel has a maximum white-point color shift as a view angle varies from 0 to 45 degrees of $WPCS^O_{45}$ and a white-point axial efficiency of $WPAE^O$, $WPCS^O_{45}$ and $WPAE^O$ defining a performance point of the display panel being to the right of the performance curve, a distance from the performance point of the display panel to the performance curve along a $WPCS^C_{45}$ axis being at least 0.005; and disposing a color-correction component on the OLED display panel, the color-correction component configured such that the display has a maximum white-point color shift as a view angle varies from 0 to 45 degrees of $WPCS_{45}$ and a white-point axial efficiency of WPAE, $WPCS_{45}$ and WPAE defining a performance point of the display being above or to the left of the performance curve.

Embodiment 2 is the method of Embodiment 1 where the providing step includes selecting the plurality of design parameters such that $WPCS^O_{45}$ is greater than $WPCS_{45}^{LA}$.

Embodiment 3 is the method of Embodiment 1 or 2, where the providing step includes designing the OLED display panel, the designing step including identifying the plurality of design parameters.

Embodiment 4 is the method of Embodiment 3, where the designing step further includes choosing values of the plurality of design parameters to deliberately create an imbalance in color mixing weights of the OLED display panel at one or more oblique viewing angles.

Embodiment 5 is the method of Embodiment 4 further including, prior to the choosing step, characterizing a color correction provided by the color-correction component, the choosing step including selecting the imbalance such that the color correction provided by the color-correction component at least partially corrects the imbalance in color mixing weights.

Embodiment 6 is the method of Embodiment 4, where the OLED display panel includes a plurality of pixels, each pixel including a plurality of subpixels, each subpixel including a plurality of OLED layers, the plurality of design parameters including an optical thickness of each layer in the plurality of OLED layers.

Embodiment 7 is a method of making an organic light emitting diode (OLED) display, the method including:

providing an OLED display panel such that each comparative display panel in a plurality of comparative display panels otherwise equivalent to the OLED display panel except for one or more values of a plurality of design parameters has a maximum white-point color shift as a view angle varies from 0 to 45 degrees of $WPCS^C_{45}$, a white-point axial efficiency of $WPAE^C$, and a blue axial efficiency of $BAE^C$, the providing step including selecting the plurality of design parameters such that the OLED display panel has a maximum white-point color shift as a view angle varies from 0 to 45 degrees of $WPCS^O_{45}$ and a white-point axial efficiency of $WPAE^O$, where for at least one comparative display panel, $WPCS^C_{45}$ is no more than $WPCS^O_{45}$−0.005 and $WPAE^C$ is no less than $WPAE^O$−1 Cd/A;

disposing a color-correction component on the OLED display panel, the color-correction component configured such that the display has a maximum white-point color shift from 0 to 45 degrees of $WPCS_{45}$ and a blue axial efficiency of BAE, $WPCS_{45}$ being less than $WPCS^C_{45}$+0.005, BAE being at least 10% greater than $BAE^C$.

Embodiment 8 is an organic light emitting diode (OLED) display including:

a pixelated OLED display panel having a maximum white-point color shift from 0 to 45 degrees of $WPCS^O_{45}$ and a white-point axial efficiency of $WPAE^O$, the pixelated OLED display panel including a plurality of pixels, each pixel including a plurality of subpixels, each subpixel including a plurality of OLED layers; and a color-correction component disposed on the pixelated OLED display panel, the color-correction component configured such that the display has a maximum white-point color shift from 0 to 45 degrees of $WPCS_{45}$ and a white-point axial efficiency of WPAE. A plurality of comparative display panels otherwise equivalent to the pixelated OLED display panel but having one or more different optical thicknesses of the OLED layers have a maximum white-point color shift from 0 to 45 degrees of $WPCS^C_{45}$ and a white-point axial efficiency of $WPAE^C$, the plurality of comparative display panels defining a first performance curve along a boundary of performance points in $WPCS^C_{45}$–$WPAE^C$ space. A plurality of comparative displays otherwise equivalent to the display but having one or more different optical thicknesses of the OLED layers defines a second performance curve along a boundary of performance points in $WPCS^C_{45}$–$WPAE^C$ space, the second performance curve being above or to the left of the first performance curve, $WPCS_{45}$ and WPAE defining a performance point of the display substantially along the second performance curve. The second performance curve and the plurality of comparative displays defines a third performance curve in $WPCS^C_{45}$–$WPAE^C$ space such that for each comparative display in the plurality of comparative displays having a performance point along the second performance curve, removing the color-correction component from the comparative display results in a comparative display panel having a performance point along the third performance curve, the third performance curve being to the right of the first performance curve, $WPCS^O_{45}$ and $WPAE^O$ defining a performance point of the display panel substantially along the third performance curve.

Embodiment 9 is the display of Embodiment 8, where $WPCS^C_{45}$ of a comparative display panel in the plurality of comparative display panels is no more than $WPCS^O_{45}$–0.005, $WPAE^C$ of the comparative display panel is no less than $WPAE^O$–1 Cd/A, and $WPCS_{45}$ is less than $WPCS^C_{45}$ of the comparative display panel.

Embodiment 10 is the display of Embodiment 9, where the plurality of subpixels includes a plurality of blue subpixels, each blue subpixel having a hole transport layer, a thickness of the hole transport layer of the blue subpixel being 1.02 to 1.1 times a thickness of a hole transport layer of a corresponding blue subpixel in the comparative display panel.

Embodiment 11 is the display of Embodiment 8, where the pixelated OLED display panel has a maximum blue-point color shift as a view angle varies from 0 to 45 degrees of $BPCS^O_{45}$ and a blue axial efficiency of $BAE^O$, the color-correction component being configured such that the display has a maximum blue-point color shift as a view angle varies from 0 to 45 degrees of $BPCS_{45}$ and a blue axial efficiency of BAE. A first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$. $BPCS^{C1}_{45}$ is within 0.0025 of $BPCS_{45}$ and BAE is at least 10% greater than $BAE^{C1}$.

Embodiment 12 is the display of Embodiment 8, where the pixelated OLED display panel has a maximum blue-point color shift as a view angle varies from 0 to 45 degrees of $BPCS^O_{45}$ and a blue axial efficiency of $BAE^O$, the color-correction component being configured such that the display has a maximum blue-point color shift as a view angle varies from 0 to 45 degrees of $BPCS_{45}$ and a blue axial efficiency of BAE. A first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$. $BAE^{C1}$ is within 5% of BAE and $BPCS^{C1}_{45}$ is at least 0.005 greater than $BPCS_{45}$.

Embodiment 13 is an organic light emitting diode (OLED) display including:

a pixelated OLED display panel having a maximum white-point color shift from 0 to 45 degrees of $WPCS^O_{45}$ and a white-point axial efficiency of $WPAE^O$, the pixelated OLED display panel including a plurality of pixels, each pixel including a plurality of subpixels, each subpixel including a plurality of OLED layers; and a color-correction component disposed on the pixelated OLED display panel, the color-correction component configured such that the display has a maximum white-point color shift from 0 to 45 degrees of $WPCS_{45}$ and a white-point axial efficiency of WPAE. A plurality of comparative display panels otherwise equivalent to the pixelated OLED display panel but having one or more different optical thicknesses of the OLED layers have a maximum white-point color shift from 0 to 45 degrees of $WPCS^C_{45}$ and a white-point axial efficiency of $WPAE^C$, the plurality of comparative display panels defining a performance curve along a boundary of performance points in $WPCS^C_{45}$–$WPAE^C$ space, $WPCS_{45}$ and WPAE defining a performance point of the display, a blue axial efficiency BAE of the display being at least 10% greater than a blue axial efficiency $BAE^C$ of a first comparative display panel in the plurality of comparative display panels having a performance point along the performance curve and having a white-point axial efficiency within 5% of WPAE.

Embodiment 14 is an organic light emitting diode (OLED) display including:

a pixelated OLED display panel having a maximum white-point color shift from 0 to 45 degrees of $WPCS^O_{45}$ and a white-point axial efficiency of $WPAE^O$, the pixelated OLED display panel including a plurality of pixels, each pixel including a plurality of subpixels, each subpixel including a plurality of OLED layers, where a comparative display panel otherwise equivalent to the pixelated OLED display panel but having one or more different optical thicknesses of the OLED layers has a maximum white-point color shift from 0 to 45 degrees of $WPCS^C_{45}$, a white-point axial efficiency of $WPAE^C$, and a blue axial efficiency of $BAE^C$, $WPCS^C_{45}$ being no more than $WPCS^O_{45}$–0.005; and a color-correction component disposed on the pixelated OLED display panel, the color-correction component configured such that the display has a maximum white-point color shift from 0 to 45 degrees of $WPCS_{45}$ and a blue axial efficiency of BAE, $WPCS_{45}$ being less than $WPCS^C_{45}$+0.005, BAE being at least 10% greater than $BAE^C$.

Embodiment 15 is an organic light emitting diode (OLED) display including:

a pixelated OLED display panel having a ratio of blue-to-red color mixing weights at 30 degrees of $\beta^O_{30}$, and a ratio of blue-to-red color mixing weights at 45 degrees of $\beta^O_{45}$, where $\beta^O_{45} > \beta^O_{30} \geq 1.05$ and $1.5 \geq \beta^O_{45} \geq 1.1$; and a color-correction component disposed on the pixelated OLED display panel, the color-correction component configured such that a ratio of blue-to-red color mixing weights at 45 degrees of the display is $\beta_{45}$ and a ratio of blue-to-red color mixing weights at 30 degrees of the display is $\beta_{30}$, where $\beta^O_{45} - 0.1 \geq \beta_{45} \geq 2.1 - \beta^O_{45}$ and $\beta^O_{30} - 0.05 \geq \beta_{30} \geq 2.05 - \beta^O_{30}$.

Embodiment 16 is the display of Embodiment 15, where $1.08 \geq \beta_{45} \geq 0.92$, or $1.06 \geq \beta_{45} \geq 0.94$, or $1.05 \geq \beta_{45} \geq 0.95$.

Embodiment 17 is the display of Embodiment 15, where $1.06 \geq \beta_{30} \geq 0.94$, or $1.05 \geq \beta_{30} \geq 0.95$, or $1.04 \geq \beta_{30} \geq 0.96$.

Embodiment 18 is the display of Embodiment 15, where the pixelated OLED display panel has a ratio of green-to-red color mixing weights at 45 degrees, $\gamma^O_{45}$, of at least 1.03 and a ratio of green-to-red color mixing weights at 45 degrees of the display, $\gamma_{45}$, is no more than $\gamma^O_{45} - 0.01$ and $1.02 \geq \gamma_{45} \geq 0.98$.

Embodiment 19 is an organic light emitting diode (OLED) display including:

a pixelated OLED display panel including a plurality of pixels, each pixel including a plurality of subpixels, each subpixel including a plurality of OLED layers; and a color-correction component disposed on the pixelated OLED display panel, the color-correction component configured such that the display has a maximum blue-point color shift as a view angle varies from 0 to 45 degrees of $BPCS_{45}$ and a blue axial efficiency of BAE. A first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$, where $BPCS^{C1}_{45}$ is within 0.0025 of $BPCS_{45}$ and BAE is at least 10% greater than $BAE^{C1}$; or $BAE^{C1}$ is within 5% of BAE and $BPCS^{C1}_{45}$ is at least 0.005 greater than $BPCS_{45}$.

Embodiment 20 is the display of Embodiment 19, where $BPCS^{C1}_{45}$ is within 0.001 of $BPCS_{45}$ and BAE is at least 15% greater than $BAE^{C1}$, or at least 20% greater than $BAE^{C1}$, or at least 25% greater than $BAE^{C1}$.

Embodiment 21 is the display of Embodiment 19, where $BAE^{C1}$ is within 2% of BAE and $BPCS^{C1}_{45}$ is at least 0.0075 greater than $BPCS_{45}$, or at least 0.01 greater than $BPCS_{45}$, or at least 0.015 greater than $BPCS_{45}$.

Embodiment 22 is the display of Embodiment 19, where $BPCS^{C1}_{45}$ is within 0.0025 of $BPCS_{45}$ and BAE is at least 10% greater than $BAE^{C1}$, and where a second comparative display panel otherwise equivalent to the pixelated OLED display panel but having one or more different optical thicknesses of the OLED layers has a maximum blue-point color shift as a view angle varies from 0 to 45 degrees of $BPCS^{C2}_{45}$ and a blue axial efficiency of $BAE^{C2}$, $BAE^{C2}$ being within 5% of BAE and $BPCS^{C2}_{45}$ being at least 0.005 greater than $BPCS_{45}$.

Embodiment 23 is the display of any one of Embodiments 8 to 22, where the color-correction component includes a wavelength and polarization dependent partial reflector.

Embodiment 24 is the display of Embodiment 23, where the partial reflector includes an optical stack, the optical stack including a plurality of optical repeat units, each optical repeat unit including first and second polymer layers, a refractive index difference between the first and second polymer layers along a first axis being $\Delta n_y$, a refractive index difference between the first and second polymer layers along an orthogonal second axis being $\Delta n_x$, $|\Delta n_x|$ being at least 0.1 and $|\Delta n_y|$ being no more than 0.04. For refractive indices along the second axis, the optical repeat units have a smallest optical thickness T1 proximate a first side of the optical stack and a largest optical thickness T2 proximate an opposite second side of the optical stack, (T2−T1)/(T2+T1) being in a range of 0.05 to 0.2, T2 being at least 350 nm and no more 1250 nm.

Embodiment 25 is the display of any one of Embodiments 8 to 22, where the color-correction component includes a color-correction film, the color-correction film including: a plurality of microlayers, each microlayer having a maximum difference among its three orthogonal refractive indices at 550 nm is less than or equal to 0.05, each microlayer having an average refractive index being the arithmetic average of the three orthogonal refractive indices at 550 nm. The plurality of microlayers is configured into layer pairs of alternating high and low index microlayers, and the average refractive index of each high index microlayer is between 0.15 and 0.75 more than the average refractive index of each low index microlayer. The layer pairs each have optical thicknesses at 550 nm between 150 nm and 550 nm, and at least half of the layer pairs have optical thicknesses at 550 nm between 275 nm and 400 nm. The color-correction film has few enough microlayers to transmit at least 80% of unpolarized visible light at normal incidence, photopically weighted. The color-correction film has enough microlayers to reflect at least 15% of at least one wavelength of unpolarized light at 60 degrees incidence.

Embodiment 26 is the display of any one of Embodiments 8 to 22, where the color-correction component includes a polymeric film, the polymeric film including a first polymeric layer having two major surfaces. The first polymeric layer includes:

a first polymer region including a first material having a refractive index of $n_1$;

a second region including a network of interconnected pores and channels within the first polymer region, the channels including a second material having a refractive index of $n_2$. The first material includes a first elastic polymeric material and optional particles. The second material includes a second polymeric material and optional particles; and/or air.

Embodiment 27 is the display of any one of Embodiments 8 to 22, where the color-correction component includes a polymeric film, the polymeric film including a first polymeric layer having two major surfaces. The first polymeric layer is void free and includes:

a first polymeric matrix having a refractive index $n_1$; and particles having a refractive index $n_2$ uniformly dispersed within the first polymeric matrix; the particles being present in an amount of less than 30 vol-%, based on the volume of the first polymeric layer, and having a particle size range of 400 nm to 3000 nm, $n_2$ being different than $n_1$.

Embodiment 28 is the display of any one of Embodiments 8 to 22, where the color-correction component includes first and second layers and a nanostructured interface therebetween.

EXAMPLES

The Examples are generally presented as illustrations of the advantages of matched OLED devices and color correction components. The testing results generally focus on performance metrics of brightness and color shift over a range of viewing angles. The fabricated test coupons which are useful for example optical measurements are not necessarily the same as final display devices for commercial use. The particular examples herein should not be seen as limiting.

Examples 1-12 and Comparative Examples 1-12

These Examples include two particular types of color correction components, labelled simply as "diffuse adhesive" and "nanostructure" types. The testing results for these examples focus on the blue spectral component (blue subpixels) which is useful in characterizing common OLED display devices. The base OLED for each Example is listed as the corresponding Comparative Example (CE) such that CE-1 corresponds to base OLED for Example 1, for example.

Materials:

| Designation | Description | Supplier |
|---|---|---|
| Indium Tin Oxide (ITO) | Anode material | Kurt J. Lesker Company, USA |
| Aluminum | Anode material | Sigma-Aldrich Corp., St. Louis MO |
| TCTA(Tris(4-carbazoyl-9-ylphenyl)amine) | Hole Transport layer (HTL), Capping Layer | Sigma-Aldrich Corp., St. Louis MO |
| 2TNATA (4,4',4''-Tris[2-naphthyl(phenyl)amino]triphenylamine) | Electron blocking layer | Sigma-Aldrich Corp., St. Louis MO |
| Firpic (Bis[2-(4,6-difluorophenyl)pyridinato-C2,N](picolinato)iridium(III)) | Emissive Dopant material | Sigma-Aldrich Corp., St. Louis MO |
| TPBi (2,2',2''-(1,3,5-Benzinetriyl)-tris(1-phenyl-1-H-benzimidazole)) | Electron Transport Layer and Host Material | Sigma-Aldrich Corp., St. Louis MO |
| LiF (Lithium Floride) | Electron Injection Layer | Sigma-Aldrich Corp., St. Louis MO |
| Magnesium | Cathode Material | Sigma-Aldrich Corp., St. Louis MO |
| Silver | Cathode Material | Sigma-Aldrich Corp., St. Louis MO |
| Al2O3 (Aluminum Oxide) | Inorganic encapsulation layer | Kurt J. Lesker Company, USA |
| E200 (Organic Smoothing layer) | Organic Smoothing layer | Electronic Materials Index Co Ltd, South Korea |
| EHA | 2-Ethylhexyl acrylate | BASF, Florham Park, NJ |
| HEA | 2-Hydroxyethyl acrylate | BASF, Florham Park, NJ |
| iBOA | Isobornyl acrylate | Osaka chemical company, JP |
| KBM-403 | 3-Glycidoxypropyl trimethoxysilane | Shin-Etsu silicones of America, INC, Akron, Ohio |
| D-1173 | 2-Hydroxy-2-methyl-1-phenyl-propan-1-one | BASF, Florham Park, NJ |
| IRGACURE 651 | Alpha,alpha-dimethoxy-alpha-phenylacetophenone | BASF, Florham Park, NJ |
| TOSPEARL 120A | Silicone beads (2.0 microns, monodispersed) | Momentive Performance Materials, Waterford, NY |

Test Methods:

A standard set of OLED measurement methods includes luminance-current-voltage (LIV) and electroluminescent spectral measurements. These measurements utilized a PR655 spectroradiometer (Photo Research, Inc. Chatsworth CA) and Keithley 2400 Sourcemeter (Keithley Instruments Inc. Cleveland OH). These optical measurements were taken as a function of angle by rotating the OLED device, with or without color correcting component, relative to the PR655 camera. Each OLED device was tested without a color correction component as a control; subsequently a color correcting component was laminated to the OLED and again evaluated for brightness and color properties.

Transmission, haze, and clarity measurements for the diffusive adhesive type color correcting component were made using a Hazegard (BYK-Chemie GmbH, Wesel Germany, according to ASTM D1003-13).

OLED Sample Preparation:

Blue top-emissive (TE) OLED test coupons were built using standard vacuum thermal evaporation for organic and metal layers at a base pressure of about $10^{-7}$ Torr, and vacuum sputtering for the oxide layers at a base pressure of about $10^{-3}$ Torr.

An anode was fabricated which consisted of a first layer of aluminum deposited at a 100 nm thickness on a polished glass substrate and a second layer of Indium Tin Oxide (ITO) deposited at a 15 nm thickness on top of the aluminum layer. A pixel defining layer was applied to define 4×4 mm pixels useful for forming the test coupons. The OLED layers were deposited in the following order: a first hole transport layer (HTL) similar to TCTA (100 nm), an electron blocking layer similar to 2TNATA (10 nm), an emissive layer composed of materials similar to TBPi and the emissive dopant material Firpic, the emissive layer containing about 10 wt. % of the emissive dopant, an electron transport layer (ETL) of TPBi (50 nm), an electron injection layer of LiF (1.5 nm), a cathode made of a mixture of silver and magnesium, the cathode containing about 10 wt. % silver (8 nm), and a capping layer of TCTA (65 nm). A series of encapsulation layers consisting of a first sputtered $Al_2O_3$ layer (50 nm), an organic smoothing layer (E200) deposited via evaporation (2.5 µm), and a second $Al_2O_3$ (50 nm) layer were deposited on top of the OLED capping layer.

Preparation of Diffusive Adhesive Type Color Correcting Component:

The preparation methods for diffuse adhesive type of color correcting component is described in U.S. Pat. No. 9,960,389 (Hao et al.). The base adhesive solution was prepared as follows. A monomer premix was prepared by adding EHA (55 parts), iBOA (25 parts), HEA (20 parts), and 0.02 part of D-1173. The mixture was partially polymerized under a nitrogen (inert) atmosphere by exposure to ultraviolet radiation generated by an ultraviolet light emitting diode (UVA-LED) to provide a coatable syrup having a viscosity of about 1000 centipoise (cps). Then HDDA (0.15 part), IRGACURE 651 (0.15 part), and KBM-403 (0.05 part) were added to the syrup to form a homogenous adhesive coating solution.

For these examples, the particular diffuse adhesive included 2 µm diameter silicone beads (4 wt % of TOSPEARL 120A, refractive index of 1.42 available from Momentive Performance Materials, Waterford, NY) loaded into the base acrylic adhesive matrix with refractive index of 1.48. The beads were first added to adhesive solution and then mechanically stirred using an overhead Jiffy LM Pint mixer (manufactured by Jiffy Mixer Co. Inc, Corona, CA) for 2 hours. After mechanical stirring, the admixture was placed on a mixing roller for an additional 24 hours. The final coated thickness for these samples was 63 μm. The diffuse adhesive color correcting component had a measured transmission, haze, and clarity of 92.5%, 81.9%, and 91.4%, respectively.

Preparation of Nanostructure Type Color Correcting Component:

The nanostructure type color-correction component was generally described in PCT Publication No. WO 2017/205174 (Freier et al.). For these examples, a particular nanostructured film was laminated to the OLED device using an optically clear adhesive (OCA 8146, available from 3M Company, ST. Paul MN). This particular nanostructured film utilized nanostructures between low and high index layers having a root-mean-square amplitude (also denoted Var) of 125 nm and having a substantially azimuthally symmetric power spectral density (PSD) concentrated in an annulus between wavenumbers 25 μm$^1$ and 37 μm$^{-1}$. After baseline measurements of the bare OLED device, the high index (e.g., n=1.85) nanostructured layer was laminated to the OLED stack for second measurements.

Example Descriptions:

For Examples 1-8, a series of blue TE OLEDs was fabricated, as described above, where the HTL layer was systemically varied from 100 nm to 115 nm. These devices were matched with a color correction component of the diffusive adhesive type to form Examples 1-8. Again, each of these examples were tested both with (Examples 1-8) and without (Comparative Examples 1-8) the diffuse adhesive color correction component.

For Examples 9-12, A series of blue TE OLEDs were fabricated, as described above, where the HTL thickness was systematically varied from 94 nm to 103 nm. These devices were matched with a color correction component of the nanostructure type to form Examples 9-12.

Test Results:

The results (blue axial efficiency, efficiency at a view angle of 60 degrees, and maximum blue-point color shift as a view angle varies from zero and 45 degrees) for Examples and Comparative Examples 1-8 using diffusive adhesive type color correction component are shown in Table A:

TABLE A

| Example | HTL Thickness [nm] | Axial Efficiency (BAE or BAE$^C$) [cd/A] | Efficiency at 60° [cd/A] | Max Color Shift (BPCS$_{45}$ or BPCS$^C_{45}$) between 0-45° (Δu'v') |
|---|---|---|---|---|
| Comparative Example-1 | 100 | 1.79 | 0.34 | 0.032 |
| Example 1 | | 1.71 | 0.34 | 0.015 |
| Comparative Example-2 | 103 | 2.00 | 0.41 | 0.043 |
| Example 2 | | 1.62 | 0.32 | 0.011 |
| Comparative Example-3 | 103 | 1.24 | 0.19 | 0.013 |
| Example 3 | | 1.09 | 0.62 | 0.038 |
| Comparative Example-4 | 106 | 1.44 | 0.22 | 0.019 |
| Example 4 | | 1.27 | 0.54 | 0.017 |
| Comparative Example-5 | 106 | 2.15 | 0.34 | 0.045 |
| Example 5 | | 1.88 | 0.97 | 0.015 |
| Comparative Example-6 | 109 | 2.31 | 0.37 | 0.053 |
| Example 6 | | 1.99 | 0.95 | 0.017 |
| Comparative Example-7 | 112 | 2.53 | 0.43 | 0.064 |
| Example 7 | | 2.2 | 0.98 | 0.023 |
| Comparative Example-8 | 115 | 2.75 | 0.65 | 0.067 |
| Example 8 | | 2.44 | 1.04 | 0.034 |

Comparative Example 6 (control) showed color shift of 0.053 (Max Color-Shift between 0-45° (Δu'v')) which was reduced to a color shift of 0.017 with addition of color correction component (Example 6). Also, by comparison, the device of Example 6 showed an efficiency of 1.99 [cd/A] as compared to bare device of Comparative Example 4 with an efficiency of 1.44 [cd/A]. This showed 38% higher efficiency, while the color shift was comparable. The color shift of Example 6 was 0.017 compared to Comparative Example 4 (control) where the color shift was 0.019.

Figure 34:
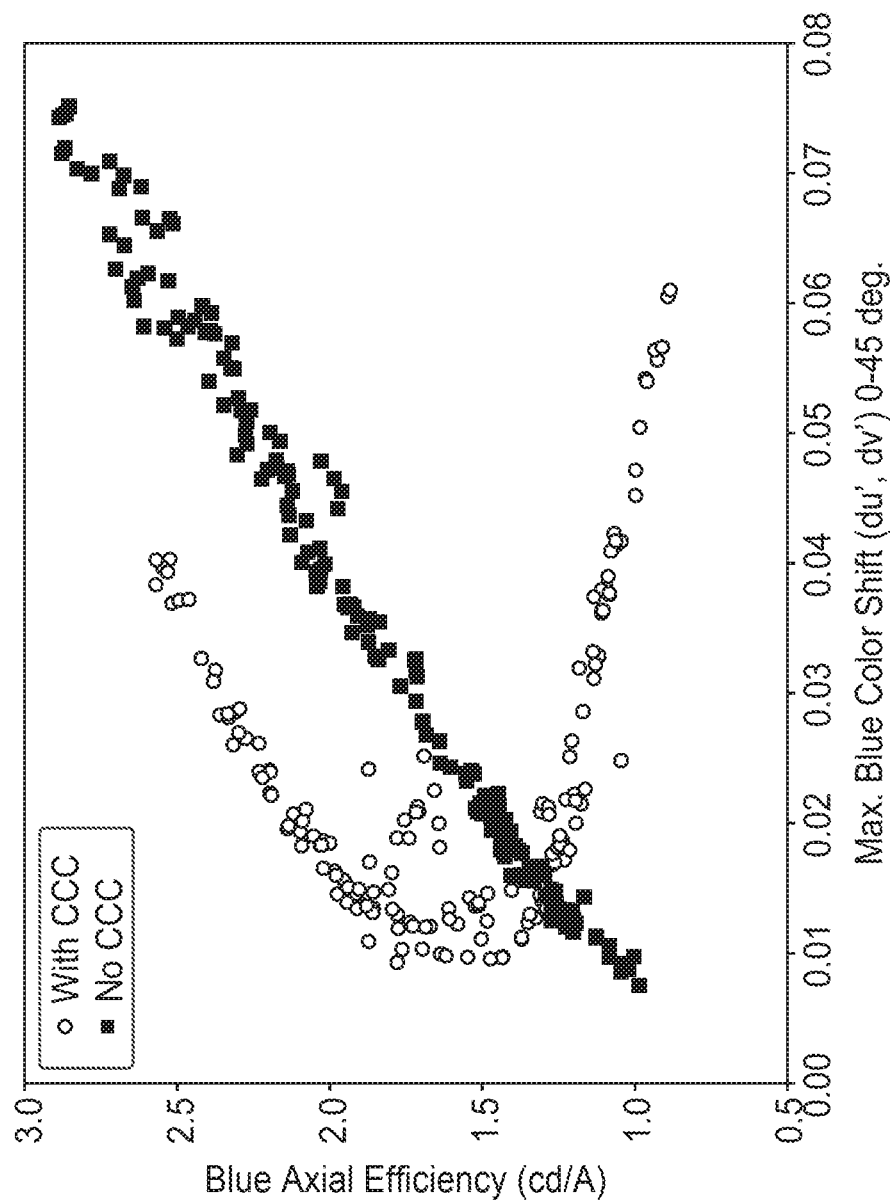
FIGS. 34-35 are plots of blue axial efficiency versus maximum blue-point color shift for displays with and without color correction components.

The blue axial efficiency and maximum blue-point color shift as a view angle varies from zero and 45 degrees for a variety of samples made according to Examples 1-8 and Comparative Examples 1-8 is shown in FIG. 34.

The results (blue axial efficiency and maximum blue-point color shift as a view angle varies from zero and 45 degrees) for Examples 9-12 and Comparative Examples 9-12 using nanostructure type color correction component are shown in Table B:

TABLE B

| Example | HTL Thickness (nm) | Axial Efficiency (BAE or BAE$^C$) [cd/A] | Max Color Shift (BPCS$_{45}$ or BPCS$^C_{45}$) between 0-45° (Δu'v') |
|---|---|---|---|
| Comparative Example-9 | 94 | 0.95 | 0.008 |
| Example 9 | | 0.94 | 0.01 |
| Comparative Example-10 | 97 | 1.17 | 0.013 |
| Example 10 | | 1.15 | 0.009 |
| Comparative Example-11 | 100 | 1.42 | 0.018 |
| Example 11 | | 1.37 | 0.013 |
| Comparative Example-12 | 103 | 1.6 | 0.024 |
| Example 12 | | 1.54 | 0.019 |

Comparative Example 10 (control) showed color shift of 0.013 (Max Color-Shift between 0-45° (Δu'v')) which was reduced to a color shift of 0.009 with addition of the color correction component (Example 10). Also, by comparison, the device of Example 11 showed an efficiency of 1.37 [cd/A] as compared to bare device of Comparative Example 10 with an efficiency of 1.17 [cd/A]. This showed 17% higher efficiency, while color shift was comparable. The color shift of Example 11 was 0.013 compared to Comparative Example 10 (control) where the color shift was 0.013.

Figure 35:
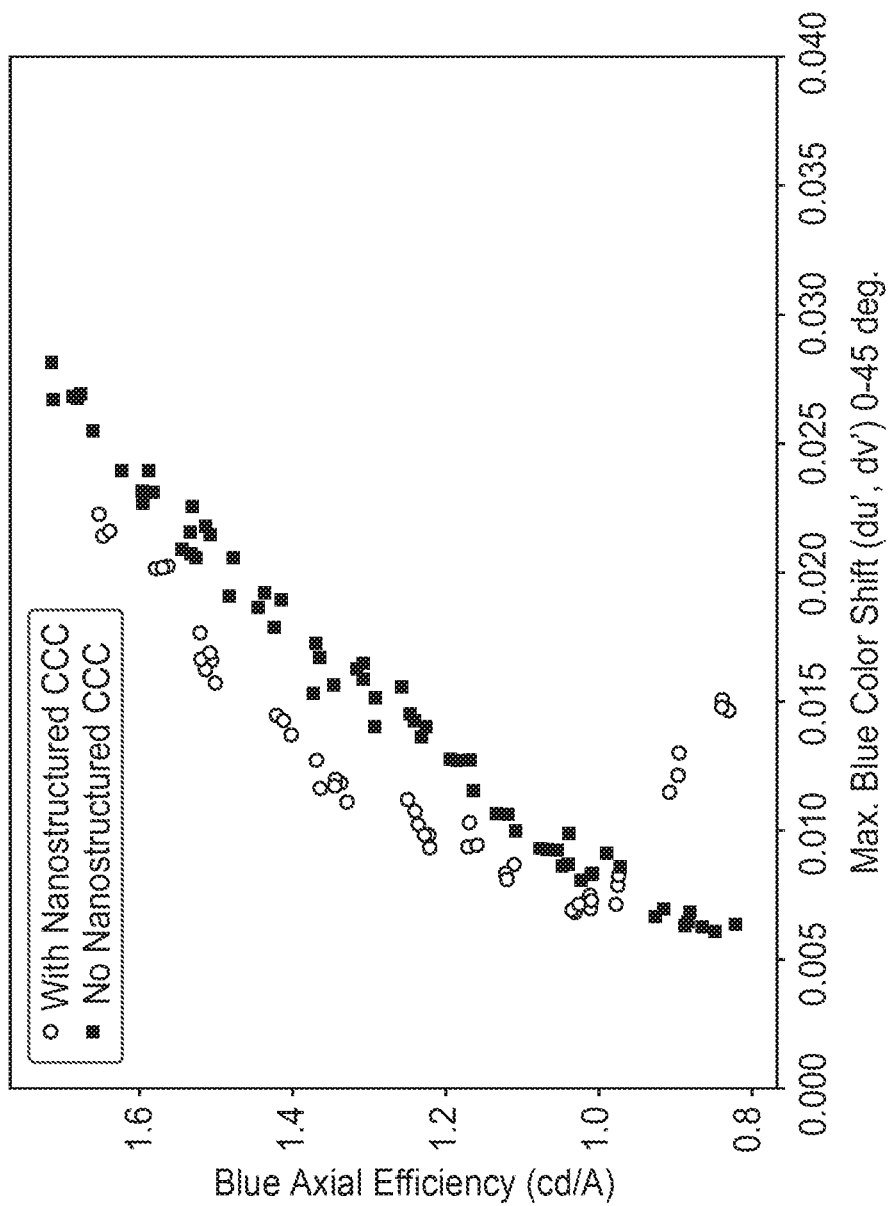

The blue axial efficiency and maximum blue-point color shift as a view angle varies from zero and 45 degrees for a variety of samples made according to Examples 9-12 and Comparative Examples 9-12 is shown in FIG. 35.

Examples 13-19 and Comparative Examples 13-19

OLED display panels including red, green and blue sub-pixels were modeled where each subpixel had the layer structure depicted in FIG. 6.

A color-correction component as generally described in PCT Publication No. WO 2017/205174 (Freier et al.) was modeled with the display panels using the optical modeling techniques described in PCT Publication No. WO 2017/205174 (Freier et al.). The color-correction component utilized nanostructures between low and high index layers having a root-mean-square amplitude (also denoted Var) of 125 nm and having an azimuthally symmetric power spectral density (PSD) concentrated in an annulus between wavenumbers 25 µm$^{-1}$ and 37 µm$^{-1}$. The high index (n=1.85) layer was disposed facing the display panel and the low index (n=1.5) layer was disposed facing away from the display panel. An optically clear adhesive (OCA) layer was disposed between the color-correction component and the TFE of the emissive stacks. The high index layer, the low index layer, and the OCA layer each had a thickness of at least a micrometer. The OCA layer was also included in comparative displays not including the color-correction component. The index of refraction of the OCA was similar to that of the low index layer and since neither the OCA nor the low index layer possessed significant absorption, the optical performance of displays including the color-correction component would be substantially unchanged by the addition of a second OCA layer on top of the low index layer. Accordingly, changes in performance between displays including the color-correction component and comparative display panels not including the color-correction component can be attributed to the insertion of the color-correction component into the OCA on top of the TFE.

The relative color mixing weight was determined as the color mixing weight at a specified view angle divided by the color mixing weight at a zero-view angle. The relative color mixing weight for red, green and blue primaries at a view angle $\theta_i$ are denoted $CMW_B(\theta_i)$, $CMW_G(\theta_i)$, $CMW_R(\theta_i)$, respectively. Ten view angles from 0 degrees to 45 degrees in 5-degree increments, inclusive, were considered. Desired ratios of blue-to-red color mixing weights, $\beta_i$, and green-to-red color mixing weights, $\gamma_i$, were determined and the root-mean-square (rms) difference between the desired ratios and the actual ratios were determined using the following equation:

$$\text{rms} = \sqrt{\frac{1}{9}\sum_{i=1}^{10}\left(\left(\frac{CMW_B(\theta_i)}{CMW_R(\theta_i)} - \beta_i\right)^2 + \left(\frac{CMW_G(\theta_i)}{CMW_R(\theta_i)} - \gamma_i\right)^2\right)}$$

For comparative display panels, the desired values were $\beta_i=1$ and $\gamma_i=1$. For the display panels of the present description, the desired values of $\beta_i$ and $\gamma_i$ were those given previously in Table 2.

Known or measured (via ellipsometry) complex refractive indices for materials known in the art for the various OLED layers were used in the optical modeling. For a given choice of materials for the layers, thicknesses of the layers were varied and thicknesses giving an rms less than 0.05 were retained as possible designs. The thickness of the hole transport layer for each of the red, green and blue emissive stacks were used as design parameters and common thicknesses for each emissive stack of the buffer layer and the capping were used as design parameters.

Figure 36:
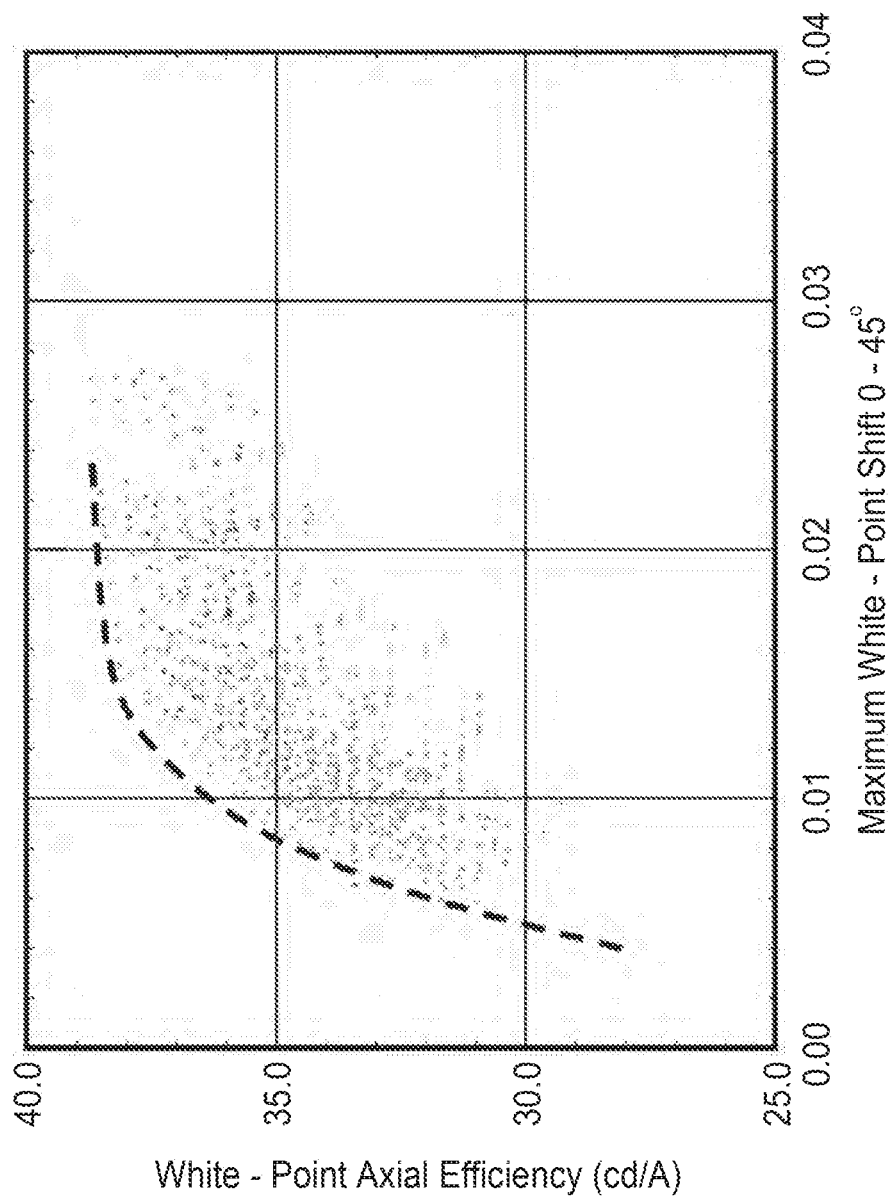
FIG. 36 is a plot in $WPCS^C_{45}$–$WPAE^C$ space of performance points of a set of comparative display panels.
Figure 37:
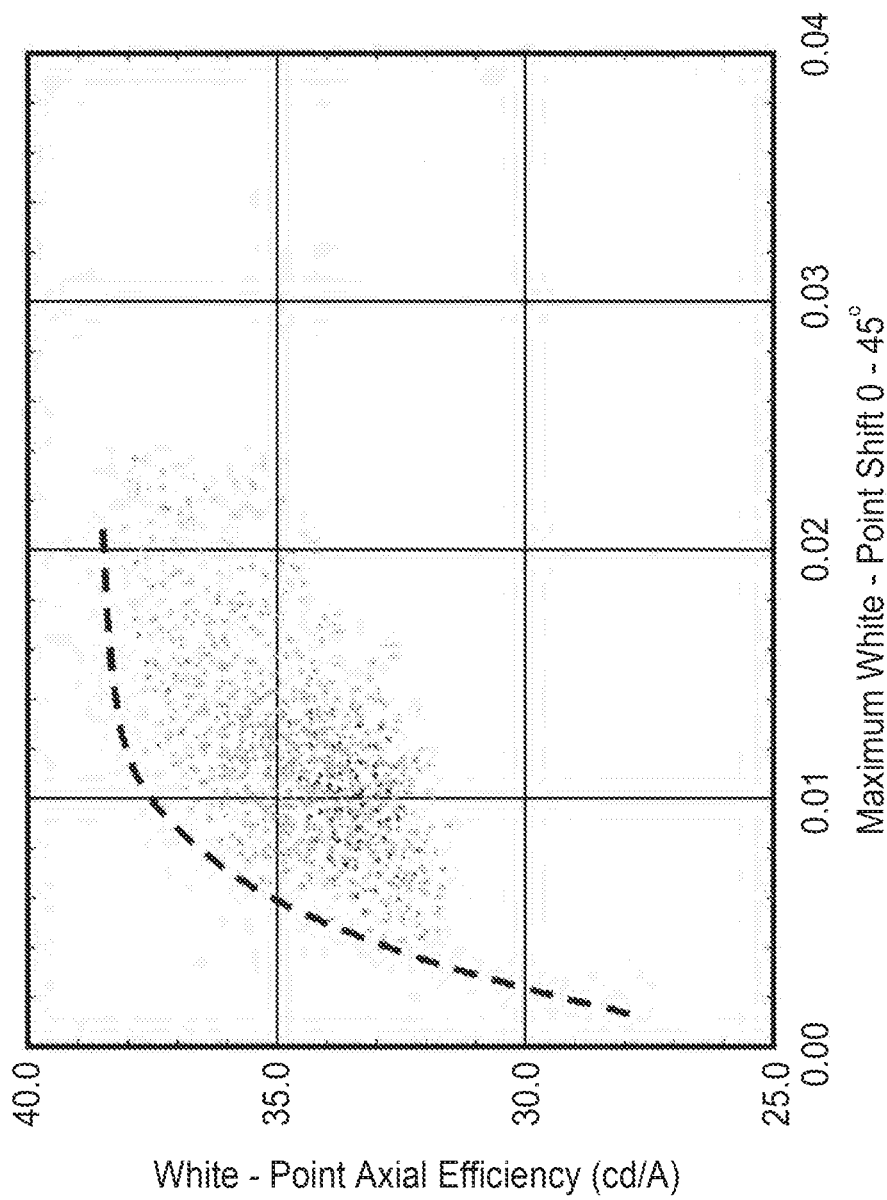
FIG. 37 is a plot in $WPCS_{45}$–$WPAE$ space of performance points of a set of OLED displays.
Figure 38:
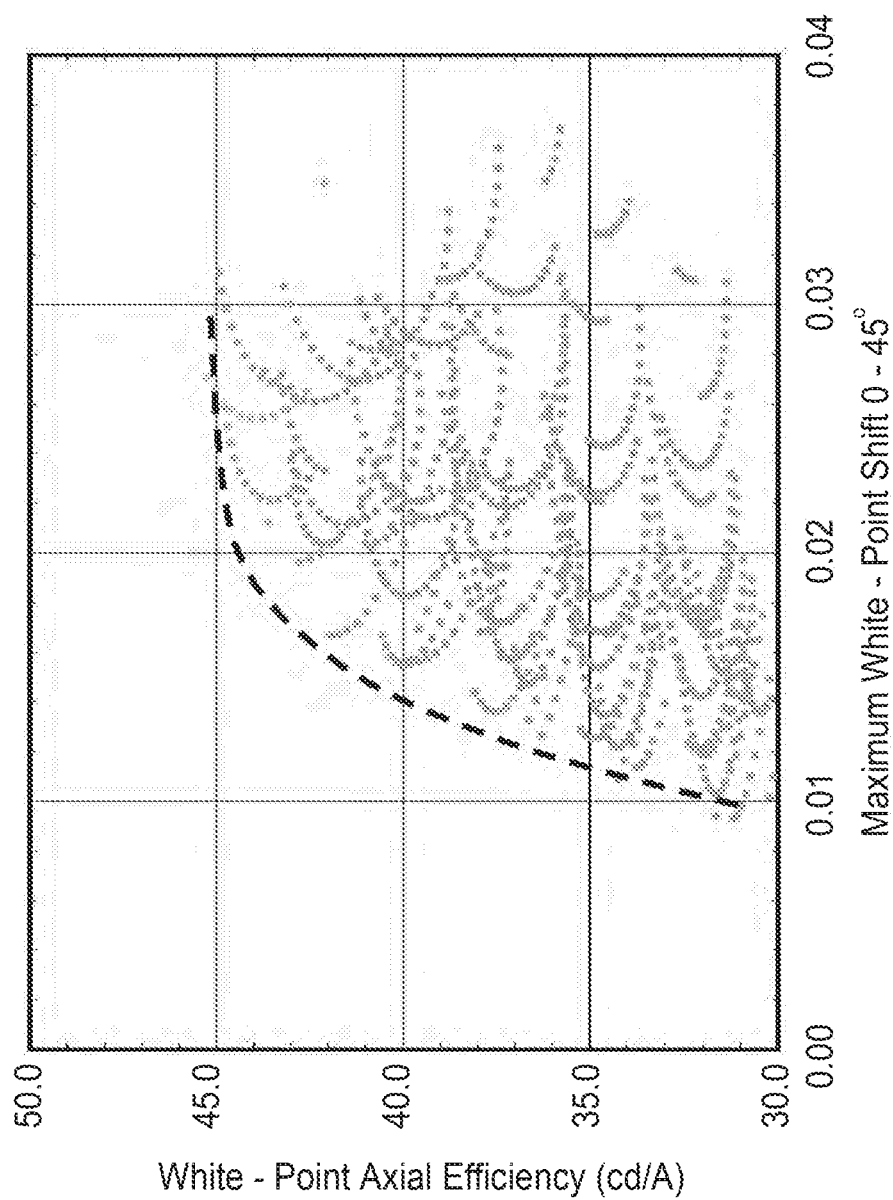
FIG. 38 is a plot in $WPCS^C_{45}$–$WPAE^C$ space of performance points of another set of comparative display panels.
Figure 39:
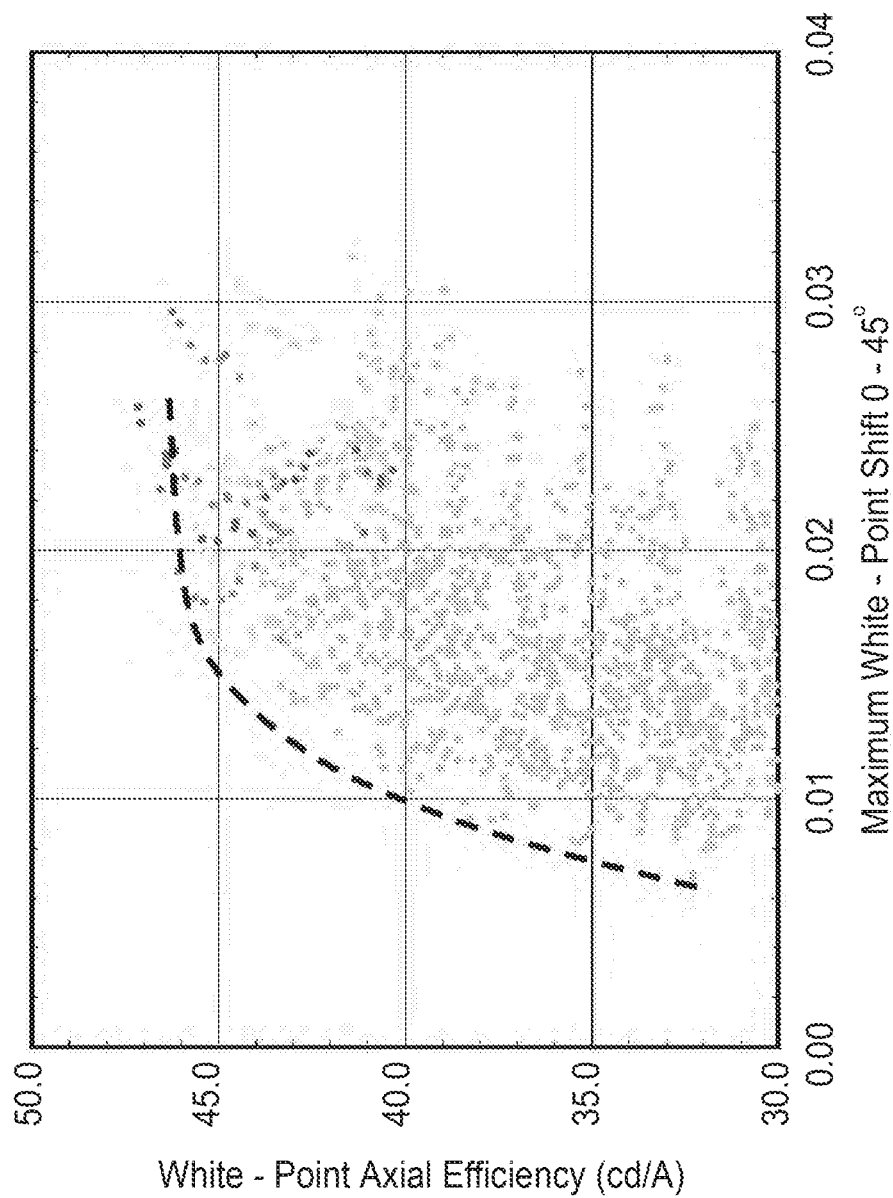
FIG. 39 is a plot in $WPCS_{45}$–$WPAE$ space of performance points of another set of OLED displays.

FIGS. 36-37 shows results for one set of OLED materials known in the art and FIGS. 38-39 shows results for another set of OLED materials known in the art. FIG. 36 shows results in WPAE$^C$–WPCS$^C_{45}$ space for comparative display panels having desired values were $\beta_i=1$ and $\gamma_i=1$. FIG. 37 shows results for displays including the color-correction component where the display panels had desired of $\beta_i$ and $\gamma_i$ given in Table 2. Performance curves along the upper left boundary of points are schematically illustrated in FIGS. 36 and 37. The performance curve of FIG. 37 is improved from that of FIG. 36 as it is shifted to lower white-point color shifts (and also higher blue axial efficiencies (not illustrated)). Similarly, FIG. 38 shows results in WPAE$^C$–WPCS$^C_{45}$ space for comparative display panels having desired values were $\beta_i=1$ and $\gamma_i=1$, and FIG. 39 shows results for displays including the color-correction component where the display panels had desired of $\beta_i$ and $\gamma_i$ given in Table 2. Performance curves along the upper left boundary of points are schematically illustrated in FIGS. 38 and 39. The performance curve of FIG. 39 is improved from that of FIG. 38 as it is shifted to lower white-point color shift and higher white-point axal efficiencies and also higher blue axial efficiencies (not illustrated).

Figure 40:
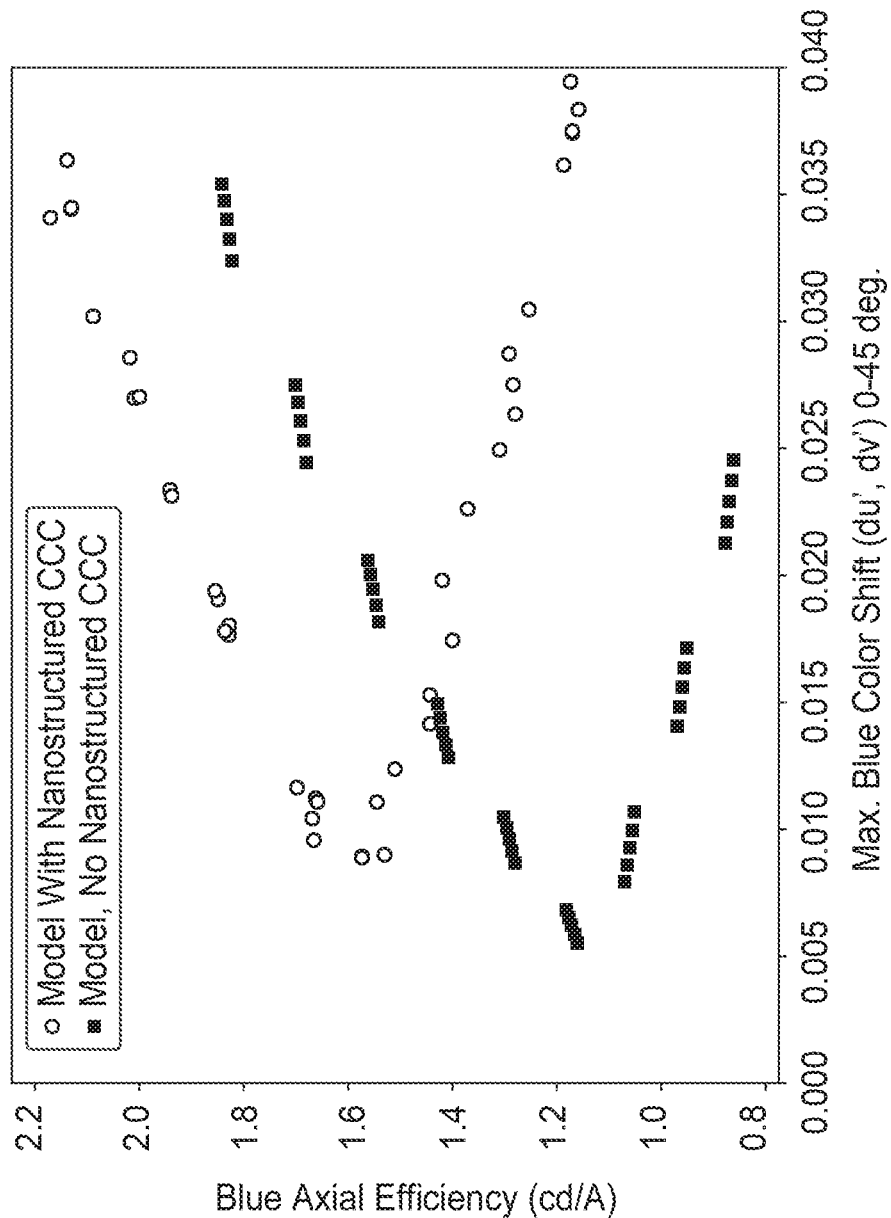
FIG. 40 is a plot of blue axial efficiency versus maximum blue-point color shift determined by modeling.
Figure 41:
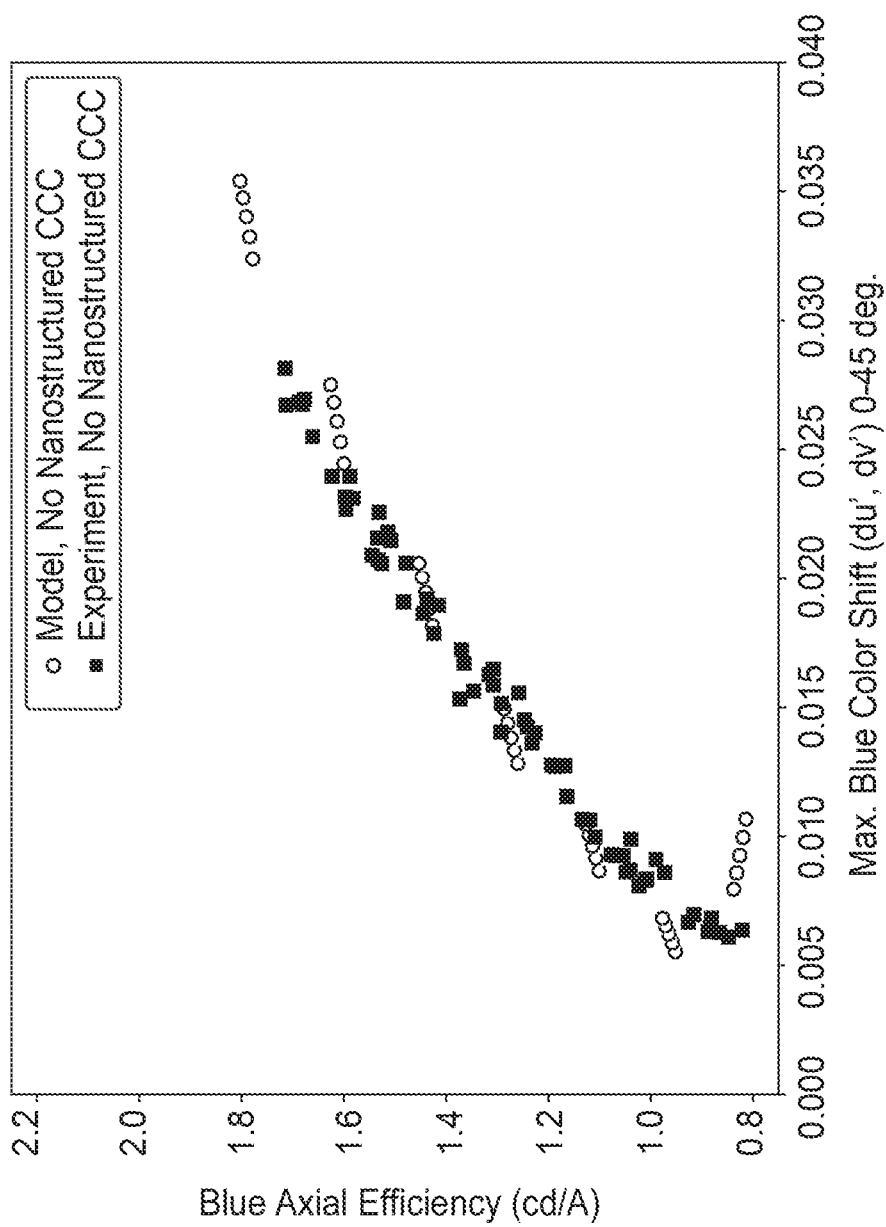
FIG. 41 is a plot of blue axial efficiency versus maximum blue-point color shift for display panels as determined by experiment and by modeling.

Table C provides additional results for comparative display panels of FIG. 36 (Comparative Examples 13 and 14) when the color-correction component is added and additional results for displays of FIG. 40 (Examples 13 and 14) when the color-correction component is removed.

TABLE C

| Example | WPCS$^C_{45}$ w/o Color-Correct. | WPAE$^C$ w/o Color-Correct. (cd/A) | BAE$^C$ w/o Color-Correct. (cd/A) | WPCS$_{45}$ w/ Color-Correct. | WPAE w/ Color-Correct. (cd/A) | BAE w/ Color-Correct. (cd/A) |
|---|---|---|---|---|---|---|
| CE-13 | 0.014 | 37.2 | 4.0 | 0.012 | 36.1 | 3.8 |
| CE-14 | 0.009 | 31.9 | 2.8 | 0.016 | 30.6 | 2.7 |
| 13 | 0.022 | 38.3 | 4.5 | 0.013 | 37.1 | 4.4 |
| 14 | 0.017 | 34.3 | 3.8 | 0.006 | 33.1 | 3.7 |

To determine the sensitivity of the performance of the display to manufacturing variations, 2% root-mean-square normal random thickness errors were added to 5 layer thicknesses (red, green, and blue HTL thickness, and buffer and capping layer thicknesses) for displays 1-2 with the color-correction component and comparative displays CE-13-CE-14 without the color-correction component. The spread in WPAE–WPCS$_{45}$ space about the nominal performance point was found to be significantly smaller for displays 1-2 than for comparative displays CE-13-CE-14. The size of the spread can be characterized by the yield which is defined as the percent of displays satisfying specified performance criteria. Since comparative display CE-13 and display Example 13 represent relatively high efficiency and relatively high color shift designs, the specified performance criteria for comparative display CE-13 and display Example 13 were taken to be WPCS$_{45}$ less than 0.02 and WPAE greater than 36 cd/A. The yield was found to be 88% for display Example 13 and 75% for comparative display CE-13. Since comparative display CE-14 and display Example 2 represent relatively low efficiency and relatively low color shift designs, the specified performance criteria for comparative display CE-14 and display Example 14 were taken to be WPCS$_{45}$ less than 0.01 and WPAE greater than 31 cd/A. The yield was found to be 90% for display Example 14 and 55% for comparative display CE-14.

Blue subpixels with and without a nanostructured color-correction component were modeled as described above and blue axial efficiency and maximum blue-point color shift as a view angle varies from zero and 45 degrees were determined from the modeling. The results for Examples 15-19 and Comparative Examples 15-19 using a nanostructured type color correction component are listed in Table D:

TABLE D

| Example | HTL Thickness [nm] | Axial Efficiency (BAE or BAE$^C$) [cd/A] | Max Color Shift (BPCS$_{45}$ or BPCS$^C_{45}$) between 0-45° ($\Delta$u'v') |
|---|---|---|---|
| Comparative Example-15 | 99 | 0.96 | 0.006 |
| Example 15 | | 0.96 | 0.038 |
| Comparative Example-16 | 101 | 1.11 | 0.010 |
| Example 16 | | 1.10 | 0.028 |
| Comparative Example-17 | 107 | 1.61 | 0.026 |
| Example 17 | | 1.58 | 0.011 |
| Comparative Example-1 | 109 | 1.79 | 0.034 |
| Example 18 | | 1.80 | 0.018 |
| Comparative Example-19 | 113 | 2.15 | 0.052 |
| Example 19 | | 2.16 | 0.034 |

Comparative Example 16 showed a color shift of 0.010 (Max Color-Shift between 0-45° ($\Delta$u'v')) with an efficiency of 1.11 [cd/A] while, by comparison, the device of Example 17 showed an efficiency of 1.58 cd/A with a color shift of 0.011. This showed a 42% higher efficiency, while color shift was comparable.

The calculated blue axial efficiencies versus maximum blue-point color shifts as a view angle varies from zero and 45 degrees is shown in FIG. 40. Calculated and measured (as described for Examples 9-12 and Comparative Examples 9-12) blue axial efficiencies versus maximum blue-point color shifts as a view angle varies from zero and 45 degrees for display panels without the color-correcting component are shown in FIG. 45. The modeled HTL thickness varied from 95 to 109 nm and the experimental data was for HTL thicknesses from 109 to 113 nm. The difference in HTL thickness ranges was selected to give close results for the calculated and measured values. This shift in HTL thickness is most likely due to slight discrepancies between modeled and experimental variables. The results indicate that the modeling accurately captures the trends in the blue axial efficiencies versus maximum blue-point color shifts as a view angle varies from zero and 45 degrees.

Terms such as "about" will be understood in the context in which they are used and described in the present description by one of ordinary skill in the art. If the use of "about" as applied to quantities expressing feature sizes, amounts, and physical properties is not otherwise clear to one of ordinary skill in the art in the context in which it is used and described in the present description, "about" will be understood to mean within 10 percent of the specified value. A quantity given as about a specified value can be precisely the specified value. For example, if it is not otherwise clear to one of ordinary skill in the art in the context in which it is used and described in the present description, a quantity having a value of about 1, means that the quantity has a value between 0.9 and 1.1, and that the value could be 1.

All references, patents, and patent applications referenced in the foregoing are hereby incorporated herein by reference in their entirety in a consistent manner. In the event of inconsistencies or contradictions between portions of the incorporated references and this application, the information in the preceding description shall control.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. An organic light emitting diode (OLED) display comprising:
   a pixelated OLED display panel having a maximum white-point color shift as a view angle varies from 0 to 45 degrees of WPCS$^0_{45}$ and a white-point axial efficiency of WPAE$^0$, the pixelated OLED display panel comprising a plurality of pixels, each pixel comprising a plurality of subpixels, each subpixel comprising a plurality of OLED layers; and
   a color-correction component disposed on the pixelated OLED display panel, the color-correction component configured such that the display has a maximum white-point color shift as a view angle varies from 0 to 45 degrees of WPCS$_{45}$ and a white-point axial efficiency of WPAE,
   wherein each comparative display panel in a plurality of comparative display panels otherwise equivalent to the pixelated OLED display panel but having one or more different optical thicknesses of the OLED layers has a maximum white-point color shift as a view angle varies from 0 to 45 degrees of WPCS$^C_{45}$ and a white-point axial efficiency of WPAE, the plurality of comparative display panels defining a first performance curve along a boundary of performance points in WPCS$^C_{45}$-WPAE$^C$ space,
   wherein a plurality of comparative displays otherwise equivalent to the display but having one or more different optical thicknesses of the OLED layers defines a second performance curve along a boundary of performance points in WPCS$^C_{45}$-WPAE$^C$ space, the second performance curve being above or to the left of the first performance curve, WPCS$_{45}$ and WPAE defining a performance point of the display substantially along the second performance curve,
   wherein the second performance curve and the plurality of comparative displays defines a third performance curve in WPCS$^C_{45}$-WPAE$^C$ space such that for each comparative display in the plurality of comparative displays having a performance point along the second performance curve, removing the color-correction component from the comparative display results in a comparative display panel having a performance point along the third performance curve, the third performance curve being to the right of the first performance curve, WPCS$^0_{45}$ and WPAE$^0$ defining a performance point of the display panel substantially along the third performance curve.

2. The display of claim 1, wherein WPCS$^C_{45}$ of a first comparative display panel in the plurality of comparative display panels is no more than WPCS$^0_{45}$-0.005, WPAE$^C$ of the first comparative display panel is no less than WPAE$^0$-1 Cd/A, and WPCS$_{45}$ is less than WPCS$^C_{45}$ of the first comparative display panel.

3. The display of claim 2, wherein the plurality of subpixels includes a plurality of blue subpixels, each blue subpixel having a hole transport layer, a thickness of the hole transport layer of the blue subpixel being 1.02 to 1.1 times a thickness of a hole transport layer of a corresponding blue subpixel in the first comparative display panel.

4. The display of claim 1, wherein a blue axial efficiency BAE of the display is at least 10% greater than a blue axial efficiency $BAE^C$ of a first comparative display panel in the plurality of comparative display panels having a performance point along the second performance curve and having a white-point axial efficiency within 5% of WPAE.

5. The display of claim 1, wherein the pixelated OLED display panel has a maximum blue-point color shift as a view angle varies from 0 to 45 degrees of $BPCS^O_{45}$ and a blue axial efficiency of $BAE^O$, the color-correction component being configured such that the display has a maximum blue-point color shift as a view angle varies from 0 to 45 degrees of $BPCS_{45}$ and a blue axial efficiency of BAE, a first comparative display panel in the plurality of comparative display panels having a maximum blue-point color shift as a view angle varies from 0 to 45 degrees of $BPCS^{C1}_{45}$ and a blue axial efficiency of $BAE^{C1}$, $BPCS^{C1}_{45}$ being within 0.0025 of $BPCS_{45}$ and BAE being at least 10% greater than $BAE^{C1}$.

6. The display of claim 1, wherein the pixelated OLED display panel has a maximum blue-point color shift as a view angle varies from 0 to 45 degrees of $BPCS^O_{45}$ and a blue axial efficiency of $BAE^O$, the color-correction component being configured such that the display has a maximum blue-point color shift as a view angle varies from 0 to 45 degrees of $BPCS_{45}$ and a blue axial efficiency of BAE, a first comparative display panel in the plurality of comparative display panels having a maximum blue-point color shift as a view angle varies from 0 to 45 degrees of $BPCS^{C1}_{45}$ and a blue axial efficiency of $BAE^{C1}$, $BAE^{C1}$ being within 5% of BAE and $BPCS^{C1}_{45}$ being at least 0.005 greater than $BPCS_{45}$.

7. The display of claim 1, wherein the pixelated OLED display panel has a ratio of blue-to-red color mixing weights at 30 degrees of $\beta^O_{30}$ and a ratio of blue-to-red color mixing weights at 45 degrees of $\beta^O_{45}$ such that $\beta^O_{45} > \beta^O_{30} \geq 1.05$ and $1.5 \geq \beta^O_{45} \geq 1.1$, and wherein the color-correction component is configured such that a ratio of blue-to-red color mixing weights at 45 degrees of the display is $\beta_{45}$ and a ratio of blue-to-red color mixing weights at 30 degrees of the display is $\beta_{30}$ such that $\beta^O_{45} - 0.1 \geq \beta_{45} \geq 2.1 - \beta^O_{45}$ and $\beta^O_{30} - 0.05 \geq \beta_{30} \geq 2.05 - \beta^O_{30}$.

8. The display of claim 7, wherein $1.06 \geq \beta_{45} \geq 0.94$ and $1.05 \geq \beta_{30} \geq 0.95$.

9. The display of claim 1, wherein the color-correction component comprises a wavelength and polarization dependent partial reflector comprising an optical stack, the optical stack comprising a plurality of optical repeat units, each optical repeat unit including first and second polymer layers, a refractive index difference between the first and second polymer layers along a first axis being Δny, a refractive index difference between the first and second polymer layers along an orthogonal second axis being Δnx, |Δnx| being at least 0.1 and |Δny| being no more than 0.04, wherein for refractive indices along the second axis, the optical repeat units have a smallest optical thickness T1 proximate a first side of the optical stack and a largest optical thickness T2 proximate an opposite second side of the optical stack, (T2−T1)/(T2+T1) being in a range of 0.05 to 0.2, T2 being at least 350 nm and no more 1250 nm.

10. The display of claim 1, wherein the color-correction component comprises a color-correction film, the color-correction film comprising:
a plurality of microlayers, each microlayer having a maximum difference among its three orthogonal refractive indices at 550 nm is less than or equal to 0.05, each microlayer having an average refractive index being the arithmetic average of the three orthogonal refractive indices at 550 nm;
wherein the plurality of microlayers is configured into layer pairs of alternating high and low index microlayers, and wherein the average refractive index of each high index microlayer is between 0.15 and 0.75 more than the average refractive index of each low index microlayer;
wherein the layer pairs each have optical thicknesses at 550 nm between 150 nm and 550 nm, and at least half of the layer pairs have optical thicknesses at 550 nm between 275 nm and 400 nm;
wherein the color-correction film has few enough microlayers to transmit at least 80% of unpolarized visible light at normal incidence, photopically weighted; and
wherein the color-correction film has enough microlayers to reflect at least 15% of at least one wavelength of unpolarized light at 60 degrees incidence.

11. The display of claim 1, wherein the color-correction component comprises a polymeric film, the polymeric film comprising a first polymeric layer having two major surfaces, wherein the first polymeric layer comprises:
a first polymer region comprising a first material having a refractive index of $n_1$;
a second region comprising a network of interconnected pores and channels within the first polymer region, the channels comprising a second material having a refractive index of $n_2$,
wherein the first material comprises a first elastic polymeric material and optional particles;
wherein the second material comprises a second polymeric material and optional particles;
and/or air.

12. The display of claim 1, wherein the color-correction component comprises a polymeric film, the polymeric film comprising a first polymeric layer having two major surfaces, wherein the first polymeric layer is void free and comprises:
a first polymeric matrix having a refractive index $n_1$; and
particles having a refractive index $n_2$ uniformly dispersed within the first polymeric matrix; the particles being present in an amount of less than 30 vol-%, based on the volume of the first polymeric layer, and having a particle size range of 400 nm to 3000 nm, $n_2$ being different than $n_1$.

13. The display of claim 1, wherein the color-correction component comprises first and second layers and a nanostructured interface therebetween.

14. An organic light emitting diode (OLED) display comprising:
a pixelated OLED display panel comprising a plurality of pixels, each pixel comprising a plurality of subpixels, each subpixel comprising a plurality of OLED layers; and
a color-correction component disposed on the pixelated OLED display panel, the color-correction component configured such that the display has a maximum blue-point color shift as a view angle varies from 0 to 45 degrees of $BPCS_{45}$ and a blue axial efficiency of BAE, wherein a first comparative display panel otherwise equivalent to the pixelated OLED display panel but having one or more different optical thicknesses of the OLED layers has a maximum blue-point color shift as a view angle varies from 0 to 45 degrees of $BPCS^{C1}_{45}$ and a blue axial efficiency of $BAE^{C1}$, wherein $BPCS^{C1}_{45}$ is within 0.0025 of $BPCS_{45}$ and BAE is at least 10% greater than $BAE^{C1}$; or $BAE^{C1}$ is within 5% of BAE and $BPCS^{C1}_{45}$ is at least 0.005 greater than $BPCS_{45}$.

15. The display of claim 14, wherein $BPCS^{C1}_{45}$ is within 0.001 of $BPCS_{45}$ and BAE is at least 15% greater than $BAE^{C1}$.

16. The display of claim 14, wherein $BAE^{C1}$ is within 2% of BAE and $BPCS^{C1}_{45}$ is at least 0.0075 greater than $BPCS_{45}$.

17. A method of making an organic light emitting diode (OLED) display, the method comprising:

providing an OLED display panel comprising a plurality of pixels, each pixel comprising a plurality of subpixels, each subpixel comprising a plurality of OLED layers, such that each comparative display panel in a plurality of comparative display panels otherwise equivalent to the OLED display panel except for having one or more different optical thicknesses of the OLED layers has a maximum white-point color shift as a view angle varies from 0 to 45 degrees of $WPCS^{C}_{45}$ and a white-point axial efficiency of WPAE, the plurality of comparative display panels defining a performance curve along a boundary of performance points in $WPCS^{C}_{45}$-$WPAE^{C}$ space, the performance curve extending from a first endpoint having a lowest acceptable efficiency to a second endpoint having a largest acceptable white-point color shift $WPCS_{45}^{LA}$, the providing step comprising selecting the optical thicknesses such that the OLED display panel has a maximum white-point color shift as a view angle varies from 0 to 45 degrees of $WPCS^{O}_{45}$ and a white-point axial efficiency of $WPAE^{O}$, $WPCS^{O}_{45}$ and $WPAE^{O}$ defining a performance point of the display panel being to the right of the performance curve, a distance from the performance point of the display panel to the performance curve along a $WPCS^{C}_{45}$ axis being at least 0.005; and disposing a color-correction component on the OLED display panel, the color-correction component configured such that the display has a maximum white-point color shift as a view angle varies from 0 to 45 degrees of $WPCS_{45}$ and a white-point axial efficiency of WPAE, $WPCS_{45}$ and WPAE defining a performance point of the display being above or to the left of the performance curve.

18. The method of claim 17, wherein the providing step comprises selecting the optical thicknesses such that $WPCS^{O}_{45}$ is greater than $WPCS_{45}^{LA}$.

19. The method of claim 17, wherein the providing step comprises choosing values of the optical thicknesses to deliberately create an imbalance in color mixing weights of the OLED display panel at one or more oblique viewing angles.

20. The method of claim 17, wherein the display has a blue axial efficiency of BAE and each comparative display panel in the plurality of comparative display panels has a blue axial efficiency of $BAE^{C}$, wherein for at least one comparative display panel in the plurality of comparative display panels, $WPCS^{C}_{45}$ is no more than $WPCS^{O}_{45}$−0.005 and $WPAE^{C}$ is no less than $WPAE^{O}$−1 Cd/A, $WPCS_{45}$ being less than $WPCS^{C}_{45}$+0.005, BAE being at least 10% greater than $BAE^{C}$.

* * * * *

UNITED STATES PATENT AND TRADEMARK OFFICE
CERTIFICATE OF CORRECTION

PATENT NO. : 12,007,593 B2
APPLICATION NO. : 17/044367
DATED : June 11, 2024
INVENTOR(S) : Nicholas Carter Erickson Page 1 of 1

It is certified that error appears in the above-identified patent and that said Letters Patent is hereby corrected as shown below:

In the Claims

Column 76
Line 36, In Claim 1, delete "axial efficiency of WPAE" and insert -- axial efficiency of $WPAE^c$ --, therefor.

Column 77
Line 67, In Claim 9, delete "no more 1250 nm" and insert -- no more than 1250 nm --, therefor.

Column 79
Line 27, In Claim 17, delete "axial efficiency of WPAE" and insert -- axial efficiency of $WPAE^c$ --, therefor.

Signed and Sealed this
Eleventh Day of March, 2025

Coke Morgan Stewart
*Acting Director of the United States Patent and Trademark Office*